(12) United States Patent
Fishbein et al.

(10) Patent No.: US 11,654,132 B2
(45) Date of Patent: May 23, 2023

(54) METHODS FOR TREATING COVID-19

(71) Applicant: MEDSTAR HEALTH INC., Columbia, MD (US)

(72) Inventors: Thomas M. Fishbein, Columbia, MD (US); Khalid M. Khan, Potomac, MD (US); Alexander H. Kroemer, Washington, DC (US)

(73) Assignee: MEDSTAR HEALTH, INC., Columbia, MD (US)

( * ) Notice: Subject to any disclaimer, the term of this patent is extended or adjusted under 35 U.S.C. 154(b) by 0 days.

(21) Appl. No.: 17/853,355

(22) Filed: Jun. 29, 2022

(65) Prior Publication Data
US 2022/0395488 A1     Dec. 15, 2022

Related U.S. Application Data

(63) Continuation-in-part of application No. PCT/US2021/030063, filed on Apr. 30, 2021.
(Continued)

(51) Int. Cl.
| | | |
|---|---|---|
| *A61K 31/4025* | (2006.01) | |
| *A61P 31/14* | (2006.01) | |
| *A61K 38/17* | (2006.01) | |
| *A61K 38/20* | (2006.01) | |
| *A61K 38/48* | (2006.01) | |

(52) U.S. Cl.
CPC ........ *A61K 31/4025* (2013.01); *A61K 38/177* (2013.01); *A61K 38/1709* (2013.01); *A61K 38/1793* (2013.01); *A61K 38/20* (2013.01); *A61K 38/204* (2013.01);
(Continued)

(58) Field of Classification Search
CPC ........................... A61K 31/4025; A61P 31/14
See application file for complete search history.

(56) References Cited

U.S. PATENT DOCUMENTS

| | | | |
|---|---|---|---|
| 7,417,029 B2 | 8/2008 | Wannamaker et al. | |
| 7,807,659 B2 * | 10/2010 | Diu-Hercend | A61P 7/06 |
| | | | 514/91 |

(Continued)

FOREIGN PATENT DOCUMENTS

| | | |
|---|---|---|
| WO | 01/90063 A2 | 11/2001 |
| WO | 2013/029006 A1 | 2/2013 |

(Continued)

OTHER PUBLICATIONS

Brienne A. McKenzie, et al., Caspase-1 inhibition prevents glial inflammasome activation and pyroptosis in models of multiple sclerosis, PNAS (2018) vol. 115, No. 26, E6065-E6074 with Correction published Jun. 17, 2019.

(Continued)

*Primary Examiner* — Shengjun Wang
(74) *Attorney, Agent, or Firm* — Duane Morris LLP; Thomas J. Kowalski; Deborah L. Lu

(57) ABSTRACT

The invention relates to methods for treating COVID-19 by targeting the inflammasome/caspase1/pyroptosis axis as a key inflammatory pathway. In particular, the invention relates to treating a patient infected with SARS-CoV-2 with an effective amount of one or more compounds that directly or indirectly inhibit one or more pathways of the inflammasome/caspase1/pyroptosis axis.

29 Claims, 13 Drawing Sheets

Specification includes a Sequence Listing.

Related U.S. Application Data

(60) Provisional application No. 63/161,635, filed on Mar. 16, 2021, provisional application No. 63/156,479, filed on Mar. 4, 2021, provisional application No. 63/018,923, filed on May 1, 2020.

(52) U.S. Cl.
CPC ...... *A61K 38/2006* (2013.01); *A61K 38/4873* (2013.01); *A61P 31/14* (2018.01)

(56) References Cited

U.S. PATENT DOCUMENTS

| | | |
|---|---|---|
| 8,329,662 B2 | 12/2012 | Wannamaker et al. |
| 8,828,950 B2 | 9/2014 | Equils et al. |
| 9,156,880 B2 | 10/2015 | Wannamaker et al. |
| 9,487,555 B2 | 11/2016 | Wannamaker et al. |
| 9,994,613 B2 | 6/2018 | Wannamaker et al. |
| 2006/0128696 A1 | 6/2006 | Vezzani et al. |
| 2015/0343011 A1 | 12/2015 | Greene et al. |
| 2019/0328709 A1 | 10/2019 | Leblanc |
| 2020/0048306 A1 | 2/2020 | Wannamaker et al. |

FOREIGN PATENT DOCUMENTS

| | | | |
|---|---|---|---|
| WO | 2015/175381 | A1 | 11/2015 |
| WO | 2017/079566 | A1 | 5/2017 |
| WO | 2021/211659 | A2 | 10/2021 |
| WO | WO-2021211659 | A2 * | 10/2021 |

OTHER PUBLICATIONS

Meir Bialer, et al., Progress report on new antiepileptic drugs: A summary of the Eleventh Eilat Conference (EILAT XI) Epilepsy Research (2013) 103. 2-30.
Conatus Pharmaceuticals, Exhibit 99.1, Inflammasome Program, May 2019, p. 1-27.
Spyridon G. Deftereos, et al., The Greek study in the Effects of Colchicine in COVID-19 complications prevention (GRECCO-19 study): rationale and study design, Hellenic Journal of Cardiology (Mar. 27, 2020) https://doi.org/10.1016/j.hjc.2020.03.002, p. 1-15.
Gilad Doitsh, et al., Pyroptosis drives CD4 T-cell depletion in HIV-1 infection. Nature. (Jan. 23. 2014) 505(7484): 509-514.
Sheng Guo, et al., The NLRP3 Inflammasome and IL-1β Accelerate Immunologically Mediated Pathology in Experimental Viral Fulminant Hepatitis. PLoS Pathog (Sep. 14, 2015) 11(9): e1005155, p. 1-21.
Yuting Jiang, et al., Complement Receptor C5aR1 Inhibition Reduces Pyroptosis in hDPP4-Transgenic Mice Infected with MERS-CoV, Viruses (2019) vol. 11, No. 39, p. 1-13.
Sannula Kesavardhana, et al., Caspases in Cell Death, Inflammation, and Gasdermin-Induced Pyroptosis, Annu. Rev. Immunol. (2020) 38:567-595.
Alexander Kroemer, et al., Adaptive Immune Deficiency in a Lethal Case of COVID-19 in a Liver Transplant Patient—Potential Role for Pyroptosis, Hepatology (Apr. 16, 2020) p. 1-23.
Alexander Kroemer, et al., Inflammasome activation and pyroptosis in lymphopenic liver patients with COVID-19, Journal of Hepatology (2020) vol. 73, p. 1258-1262.
J. Kudelova, et al., Pharmacological Caspase Inhibitors: Research Towards Therapeutic Perspectives, Review Article, JPP No. 04/2015 Article 01, Accepted Apr. 27, 2015. Retrieved: http://jpp.krakow.pl/journal/archive/08_15/articles/01_article.html.
V. Parisi, et al., Precision medicine in COVID-19: IL-1β a potential target, Journal Pre-proof—JACC: Basic to Translational Science (Accepted Apr. 9, 2020) Ref. 451, p. 1-5.
Kelly Pennington et al., Currently Available and Emerging Therapies for COVID-19. CHEST (Mar. 30, 2020) Retrieved: <https://www.chestnet.org/topic-collections/covid-19/covid-in- focus/currently-available-and-emerging-therapies-for-covid-19> p. 1-5.
Chong-Shan Shi, et al., SARS-Coronavirus Open Reading Frame-8b triggers intracellular stress pathways and activates NLRP3 inflammasomes. Cell Death Discovery (2019) 5:101, p. 1-12.
Woods Wannamaker, et al. (S)-1-((S)-2-{[1-(4-Amino-3-chlorophenyl)-methanoyl]-amino)- 3,3-dimethyl-butanoyl)-pyrrolidine-2-carboxylic acid ((2R,3S)-2-ethoxy-5-oxo-tetrahydro-furan-3-yl)-amide (VX-765), an Orally Available Selective Interleukin (IL)-Converting Enzyme/Caspase-1 Inhibitor, Exhibits Potent Anti-Inflammatory Activities by Inhibiting the Release of IL-1 Beta and IL-18, The Journal of Pharmacology and Experimental Therapeutics (2007) vol. 321, No. 2, 509-516.
Ming Yang, Cell Pyroptosis, a Potential Pathogenic Mechanism of 2019-nCoV Infection, Electronic copy available at: https://ssrn.com/abstract=3527420.
Yuan Yue, et al., SARS-Coronavirus Open Reading Frame-3a drives multimodal necrotic cell death, Cell Death and Disease (2018) 9:904.
Ayesha Zahid, et al., Pharmacological inhibitors of the NLRP3 Inflammasome, Frontiers in Immunology (Oct. 2019) vol. 10, Article 2538, p. 1-10.
Zachary B. Zalinger, et al., Role of the inflammasome-related cytokines Il-1 and Il-18 during infection with murine coronavirus, J. Neurovirol. (2017) 23:845-854.
P. Conti, et al.. Induction of pro-inflammatory cytokines (IL-1 and IL-6) and lung inflammation by Coronavirus-19 (COVI-19 or SARS-CoV-2): antiinflammatory strategies, Journal of biological regulators and homeostatic agents (Mar. 14, 2020) vol. 34, Issue 2.
International Search Report dated Sep. 16, 2021, in International Application No. PCT/US2021/030063.
Jeffrey H. Stack, et al., IL-Converting Enzyme/Caspase-1 Inhibitor VX-765 Blocks the Hypersensitive Response to an Inflammatory Stimulus in Monocytes from Familial Cold Autoinflammatory Syndrome Patients, The Journal of Immunology (2005) 175:2630-2634.

* cited by examiner

Innate Immune Phenotype

Monocyte activation

Increased B-cell tetherin expression

Subject Diary – Overview of Study Events

*Days*

| | 1 | 2 | 3 | 4 | 5 | 6 | 7 |
|---|---|---|---|---|---|---|---|
| Week 1 | 1 ☎ | 2 | 3 | 4 ☎ | 5 | 6 | 7 👤📄 |
| Week 2 | 8 | 9 | 10 ☎ | 11 | 12 | 13 | 14 👤📄 |
| Week 3 | 15 | 16 | 17 | 18 | 19 | 20 | 21 👤📄 |
| Week 4 | 22 | 23 | 24 | 25 | 26 | 27 | 28 👤📄 |
| Week 5 | 29 | 30 | 31 | 32 | 33 | 34 | 35 |
| Week 6 | 36 | 37 | 38 | 39 | 40 | 41 | 42 ☎ |
| Week 7 | 43 | 44 | 45 | 46 | 47 | 48 | 49 |
| Week 8 | 50 | 51 | 52 | 53 | 54 | 55 | 56 |
| Week 9 | 57 | 58 | 59 | 60 ☎ | 61 | 62 | 63 |

*Legend*

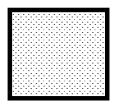 Days 1-28: On every day take study drug three times; take your temperature two times; log your general impressions and symptoms once; and engage with Telemetry Care Team

 Days 1, 4, 10, 42, 60: Receive phone calls from Study Team

 Days 7, 14, 21, 28: Visit Study Center in person

 Days 7, 14, 21, 28: Give Study Team last 7 days of Diary pages

FIG. 5A

Subject Diary – Sample Daily Log – Page 1

Date: _____  Subject Number: _____

 Common COVID-19 Symptoms  Time you are filling this out today: _____

What was the SEVERITY of these symptoms at their worst in the last 24 hours? Place an X

|  | None | Mild | Moderate | Severe |
|---|---|---|---|---|
| Stuffy or runny nose |  |  |  |  |
| Sore throat |  |  |  |  |
| Shortness of breath at rest |  |  |  |  |
| Shortness of breath with exertion |  |  |  |  |
| Cough |  |  |  |  |
| Low energy or tiredness |  |  |  |  |
| Muscle or body aches |  |  |  |  |
| Headache |  |  |  |  |
| Chills or shivering |  |  |  |  |
| Feeling hot or feverish |  |  |  |  |
| Nausea |  |  |  |  |

In the last 24 hours, how often did you have these ISSUES? Place an X

|  | 0 times | 1-2 times | 3-4 times | 5 or more times |
|---|---|---|---|---|
| Vomit (throw up) |  |  |  |  |
| Diarrhea (loose or watery stools) |  |  |  |  |

In the last 24 hours, how would you rate your SENSES? Place an X

|  | SAME as usual | LESS than usual | I have NO sense |
|---|---|---|---|
| Sense of smell |  |  |  |
| Sense of taste |  |  |  |

Over the last 24 hours, if there were any other symptoms beyond the ones listed above that you experienced, please describe them here:

FIG. 5B

Subject Diary – Sample Daily Log – Page 2

Date: _____   Subject Number: _____

Medication
Place an X to note that you have taken 3 tablets of the STUDY DRUG and note the time you took them

| Morning | Mid-Day | Evening |
|---|---|---|
|  |  |  |
| am | _m | pm |

Note any OTHER medications, vitamins, or supplements you took, other than those you told us at enrollment that you take on a regular basis; use the back of this page if you need more space

| Name | Dose | Time |
|---|---|---|
|  |  |  |
|  |  |  |
|  |  |  |
|  |  |  |

Temperature
Note your temperature from the thermometer and note the time you took the measurement

| Morning | Evening |
|---|---|
| °F | °F |
| am | pm |

Global Impression

Place an X

Time you are filling this out today: _____

|  | None | Mild | Moderate | Severe |
|---|---|---|---|---|
| In the past 24 hours, what was the severity of your OVERALL COVID-19-related symptoms at their worst? |  |  |  |  |

Place an X

|  | Yes | No |
|---|---|---|
| In the past 24 hours, have you returned to your usual HEALTH (before your COVID-19 illness)? |  |  |
| In the past 24 hours, have you returned to your usual ACTIVITIES (before your COVID-19 illness)? |  |  |

FIG. 5C

Schedule of Events Table:
↑ = In-Person; ☎ = Telephone; ▦ = Subject Self-Tracking

| Time Point (Days) | Screen / enroll | D1[9] | D4 | D7 | D10 | D14 | D21 | D28 | D42 | D60 | ET[10] |
|---|---|---|---|---|---|---|---|---|---|---|---|
| STUDY TEAM | | | | | | | | | | | |
| Inclusion / Exclusion | ↑ | | | | | | | | | | |
| Consent | ↑ | | | | | | | | | | |
| Screening Tests[1] | ↑ | | | | | | | | | | |
| Demographics | ↑ | | | | | | | | | | |
| CXR or CT | ↑ | | | | | | | | | | |
| Physical Exam | ↑ | | | ↑ | | | | ↑ | | | ↑ |
| Vitals[2] | ↑ | | | ↑ | | | ↑ | ↑ | | | ↑ |
| EKG | ↑ | | | | | | | ↑ | | | ↑ |
| CoV-2 NP[3] | | | | ↑ | | ↑ | | ↑ | | | ↑ |
| Standard labs[4] | ↑ | | | ↑ | | | ↑ | ↑ | | | ↑ |
| Blood draws[5] | ↑ | | | ↑ | | | | ↑ | | | ↑ |
| Immunology tests[6] | | | | | | | ↑ | ↑ | | | ↑ |
| CoV-2 blood[7] | | | | | | | | ↑ | | | |
| AE assessment | ↑ | ☎ | ☎ | ☎ | ☎ | ↑ | ↑ | ↑ | ☎ | ☎ | ↑ |
| Symptoms assessment | ↑ | ☎ | ☎ | ☎ | ☎ | ↑ | ↑ | ↑ | ☎ | ☎ | ↑ |
| WHO 9-Point Scale[8] | ↑ | ☎ | ☎ | ☎ | ☎ | ↑ | ↑ | ↑ | ☎ | ☎ | ↑ |
| TELEMETRY CARE TEAM | | | | | | | | | | | |
| Symptoms check-in | | ☎ Once per day through day 28 or ET | | | | | | | | | |
| SpO2 resting | | ☎ Once per day via oximeter through day 28 or ET | | | | | | | | | |
| SUBJECTS | | | | | | | | | | | |
| IP/placebo intake | | ▦ Three times per day through day 28 or ET | | | | | | | | | |
| Temperature | | ▦ Two times per day via thermometer through day 28 or ET; day 42 and day 60 | | | | | | | | | |
| Symptom tracking | | ▦ One time per day through day 28 or ET; day 42 and day 60 | | | | | | | | | |

FIG. 6

SEQUENCE LISTING

<160> NUMBER OF SEQ ID NOS: 1

<210> SEQ ID NO 1
<211> LENGTH: 4
<212> TYPE: PRT
<213> ORGANISM: Artificial Sequence
<220> FEATURE:
<223> OTHER INFORMATION: Description of Artificial Sequence: Synthetic peptide

<400> SEQUENCE: 1

Arg Val Lys Arg
1

METHODS FOR TREATING COVID-19

RELATED APPLICATIONS AND INCORPORATION BY REFERENCE

This application is a continuation-in-part of International Application No. PCT/US2021/030063 filed Apr. 30, 2021 and which published as International Publication No. WO 2021/222687 on Nov. 4, 2021, and which claims benefit of and priority to US provisional patent application Ser. Nos. 63/018,923 filed 1 May 2020, 63/156,479 filed 4 Mar. 2021 and 63/161,635 filed 16 Mar. 2021.

The foregoing applications, and all documents cited therein or during their prosecution ("appln cited documents") and all documents cited or referenced in the appln cited documents, and all documents cited or referenced herein ("herein cited documents"), and all documents cited or referenced in herein cited documents, together with any manufacturer's instructions, descriptions, product specifications, and product sheets for any products mentioned herein or in any document incorporated by reference herein, are hereby incorporated herein by reference, and may be employed in the practice of the invention. More specifically, all referenced documents are incorporated by reference to the same extent as if each individual document was specifically and individually indicated to be incorporated by reference.

SEQUENCE STATEMENT

The instant application contains a Sequence Listing which has been submitted electronically and is hereby incorporated by reference in its entirety. Said ASCII copy was created Jun. 30, 2021, is named F7259-00036_SL.txt and is 525 bytes in size.

FIELD OF THE INVENTION

The invention relates to methods for treating COVID-19 by targeting the inflammasome/caspase1/pyroptosis axis as a key inflammatory pathway.

BACKGROUND OF THE INVENTION

Beginning in December 2019, a novel coronavirus first detected in Wuhan, China, and designated SARS-CoV-2, has caused an international outbreak of respiratory illness termed Covid-19. Since the initial detection of the virus, millions of cases of Covid-19 have been confirmed worldwide, with the first reported cases in the US occurring on Jan. 19, 2020 (Holshue et al. N Engl J Med. 2020; 382(10): 929-936). The full spectrum of Covid-19 ranges from mild, self-limiting respiratory tract illness to severe progressive pneumonia, multiorgan failure, and death (Chen et al. Lancet. 2020; 395(10223): 507-513). Initial reports, first from China and then from Italy, stressed high mortality rates, ranging from 2.3% overall to as high as 15% in those aged 80 years and older (Grasselli G, A. Pesenti A, and M. Cecconi M. Critical Care Utilization for the COVID-19 Outbreak in Lombardy, Italy: Early Experience and Forecast During an Emergency Response. JAMA. 2020). However, this is likely an overestimate since the prevalence of asymptomatic carriers is as yet unknown. What is increasingly clear, though, is that individuals at highest risk are those over 65 years with concomitant chronic conditions with an inflammatory profile such as diabetes, pre-diabetes, elevated BMI, liver disease, and chronic renal impairment.

After the emergence of severe acute respiratory syndrome (SARS) in 2003, screening of approved drugs identified lopinavir, a human immunodeficiency virus (HIV) type 1 aspartate protease inhibitor, as having in vitro inhibitory activity against SARS-CoV, the virus that causes SARS in humans (Chen et al. J Clin Virol. 2004; 31(1): 69-75; Chu et al. Thorax. 2004; 59(3): 252-256; Wu et al. Proc Natl Acad Sci USA. 2004; 101(27): 10012-10017). Ritonavir is combined with lopinavir to increase its plasma half-life through the inhibition of cytochrome P450. An open-label study published in 2004 suggested, by comparison with a historical control group that received only ribavirin, that the addition of lopinavir—ritonavir (400 mg and 100 mg, respectively) to ribavirin reduced the risk of adverse clinical outcomes (acute respiratory distress syndrome or death) as well as viral load among patients with SARS (Chu et al. Thorax. 2004; 59(3): 252-256). However, the lack of randomization and the concomitant use of glucocorticoids and ribavirin in that study made the effect of lopinavir-ritonavir difficult to assess.

Recently, the combined effect of lopinavir-ritonavir in the treatment of SARS-CoV-2 was tested in a randomized study involving 200 patients in China. Unfortunately, there was no improvement in clinical symptoms, mortality, or viral loads in the lopinavir-ritanovir group compared to standard of care alone (Chu et al. Thorax. 2004; 59(3): 252-256). Hydroxychloroquine, an anti-malarial agent, combined with azithromycin, an anti-bacterial agent, were recently used in 22 patients with SARS-CoVid-2 infection in France. Viral loads appeared to diminish faster in the treated patients than in the 2 control patients, but no conclusions can be drawn from such small numbers and anyway no mention was made of its impact on clinical symptoms.

The role of the inflammasome/caspase1/pyroptosis axis as a key inflammatory pathway in the context of coronavirus infections and beyond is well known in the art. (files labelled CoV-01-CoV-06).

Yue et al. (Cell Death and Disease (2018) 9:904) found that Receptor Interacting Protein 3 (Rip3)-mediated oligomerization of SARS 3a (the largest of the SARS-CoV accessory protein open reading frames) causes necrotic cell death, lysosomal damage, and caspase-1 activation—all likely contributing to the clinical manifestations of SARS-CoV infection. Yue et al. also found that SARS 3a activates caspase-1 either directly or via an enhanced potassium efflux, which triggers NOD-, LRR- and pyrin domain-containing protein 3 (NLRP3) inflammasome assembly.

Shi et al. (Cell Death Discovery (2019) 5:101) identified several mechanisms by which a SARS-CoV open reading frame (ORF) activates intracellular stress pathways and targets the innate immune response by activating NLRP3 inflammasomes.

Zalinger et al. (J. Neurovirol. (2017) 23:845-854) used murine coronavirus, mouse hepatitis virus (MHV), infection of the central nervous system and liver to assess of the role of the inflammasome and its related cytokines on pathogenesis and host defense during viral infection. Their data suggest that inflammasome signaling is largely protective during murine coronavirus infection, in large part due to the pro-inflammatory effects of IL-18.

Jiang et al. (Viruses 2019, 11, 39; doi:10.3390/v11010039) found that MERS-CoV infection induced pyroptosis and over-activation of complement in human macrophages. Jiang et al.'s data indicate that MERS-CoV infection induces overactivation of complement, which may contribute to pyroptosis and inflammation. Pyroptosis and inflammation were suppressed by inhibiting C5aR1.

Kesavardhana et al. (Annu. Rev. Immunol. 2020. 38:567-95) reviewed mechanisms governing caspase activation and programmed cell death with special emphasis on the recent progress in caspase cross talk and caspase-driven gasdermin D (GSDMD)-induced pyroptosis.

Guo et al. (PLoS Pathog 2015 11(9): e1005155. doi: 10.1371/journal.ppat.1005155) demonstrate that the reactive oxygen species (ROS)/nucleotide-binding domain-like receptor protein 3 (NLRP3)/interleukin-1β (IL-1β) axis institutes an essential signaling pathway, which is over activated and directly causes the severe liver disease during viral infection, which sheds light on development of efficient treatments for human viral fulminant hepatitis and other severe inflammatory diseases.

The relevance of the inflammasome/caspase1/pyroptosis axis specifically in COVID-19 is also known in the art.

Parisi and Leosco (Precision medicine in COVID-19: IL-1β a potential target, JACC: Basic to Translational Science (2020)) speculated about i) the role of NLRP3 in the clinical variability of COVID-19; ii) the potential therapeutic effect in COVID-19 of IL-1β inhibition (canakinumab, anakinra), and iii) the role of visceral adipose tissue in the inflammatory response to SARS-CoV-2 infection.

Conti et al. (Journal of biological regulators and homeostatic agents Volume 32 Issue 2 2020) speculated about anti-inflammatory strategies, specifically the induction of pro-inflammatory cytokines (IL-1 and IL-6) and lung inflammation by Coronavirus-19 (COVID-19 or SARS-CoV-2).

Yang (Cell Pyroptosis, a Potential Pathogenic Mechanism of 2019-nCoV Infection (Jan. 29, 2020). Available at SSRN: https://ssrn.com/abstract=3527420 or http://dx.doi.org/10.2139/ssrn.3527420) discussed the relationship between 2019-nCoV infection and cell pyroptosis. Yang's hypothesis of the relationship between 2019-nCoV and cell pyroptosis is presented in FIG. 1.

Deftereos et al. (Hellenic Journal of Cardiology, 2020, https://doi.org/10.1016/j.hjc.2020.03.002) asked whether colchicine, administered in a relatively low dose, could potentially have an effect on the patients' clinical course by limiting the myocardial necrosis and pneumonia development in the context of COVID-19. If present, this effect would be attributed to its potential to inhibit inflammasome and (less probably) to the process of SARS-CoV-2 endocytosis in myocardial and endothelial respiratory cells.

There is a need for effective therapeutic agents to treat coronavirus infections, in particular SARS-CoV-2.

Citation or identification of any document in this application is not an admission that such document is available as prior art to the present invention.

SUMMARY OF THE INVENTION

The invention relates to methods for treating COVID-19 by targeting the inflammasome/caspase1/pyroptosis axis as a key inflammatory pathway. In particular, the invention relates to treating a patient infected with SARS-CoV-2 or a variant thereof with an effective amount of one or more compounds that inhibit one or more pathways of the inflammasome/caspase1/pyroptosis axis. Compounds that inhibit one or more pathways of the inflammasome/caspase1/pyroptosis axis include compounds that directly or indirectly inhibit the one or more pathways as direct and indirect inhibitors of pathways that are upstream or downstream of the inflammasome/caspase1/pyroptosis axis.

The present invention relates to methods for treating a patient infected with SARS-CoV-2 or a variant thereof and having pyroptotic activity which may comprise (a) determining if the patient is infected with SARS-CoV-2 or a variant thereof, (b) optionally determining if the patient has pyroptotic activity, and (c) administering an effective amount of a compound that inhibits one or more pathways of the inflammasome/caspase1/pyroptosis axis to the patient infected with SARS-CoV-2 or a variant thereof.

In another embodiment, the invention relates to screening a marker indicative of pyroptotic activity, wherein the marker has increased activity if pyroptotic activity is present as compared to the expression of the marker in the absence of pyroptotic activity. In an advantageous embodiment, the marker may be NOD-, LRR- and pyrin domain-containing protein 3 (NLRP3), IL-1 receptor antagonist (IL-1RA), interleukin-1β (IL-1β), interleukin-18 (IL-18), gasdermin D (GSDMD), and/or caspase 1.

In an advantageous embodiment, the compound that inhibits one or more pathways of the inflammasome/caspase1/pyroptosis axis is a caspase 1 inhibitor.

In a particularly advantageous embodiment, an effective amount of the compound that inhibits one or more pathways of the inflammasome/caspase1/pyroptosis axis may be about 10 mg/kg to about 100 mg/kg or about 300 mg to about 900 mg per dose or about 300 mg to about 3600 mg per day. Advantageously, the effective amount may be about 600 mg three times a day to about 900 mg three times a day. Advantageously, the administering is oral.

The methods of the invention may further comprise administering an effective amount of a caspase 1, GSDMD, IL-1R, IL-1β, IL-18, or NLRP3 inhibitor.

Accordingly, it is an object of the invention not to encompass within the invention any previously known product, process of making the product, or method of using the product such that Applicants reserve the right and hereby disclose a disclaimer of any previously known product, process, or method. It is further noted that the invention does not intend to encompass within the scope of the invention any product, process, or making of the product or method of using the product, which does not meet the written description and enablement requirements of the USPTO (35 U. S.C. § 112, first paragraph) or the EPO (Article 83 of the EPC), such that Applicants reserve the right and hereby disclose a disclaimer of any previously described product, process of making the product, or method of using the product. It may be advantageous in the practice of the invention to be in compliance with Art. 53(c) EPC and Rule 28(b) and (c) EPC. All rights to explicitly disclaim any embodiments that are the subject of any granted patent(s) of applicant in the lineage of this application or in any other lineage or in any prior filed application of any third party is explicitly reserved. Nothing herein is to be construed as a promise.

It is noted that in this disclosure and particularly in the claims and/or paragraphs, terms such as "comprises", "comprised", "comprising" and the like can have the meaning attributed to it in U.S. patent law; e.g., they can mean "includes", "included", "including", and the like; and that terms such as "consisting essentially of" and "consists essentially of" have the meaning ascribed to them in U.S. patent law, e.g., they allow for elements not explicitly recited, but exclude elements that are found in the prior art or that affect a basic or novel characteristic of the invention.

These and other embodiments are disclosed or are obvious from and encompassed by, the following Detailed Description.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The following detailed description, given by way of example, but not intended to limit the invention solely to the specific embodiments described, may best be understood in conjunction with the accompanying drawings.

FIGS. 5A-5C: Subject Diary.

FIG. 6: Schedule of Events. [1]Screening tests: HIV, Hepatitis B, Hepatitis C, and pregnancy (serum pregnancy test for women of child-bearing potential per MedStar definition at enrollment and at day 14). [2]Vital signs: oral temperature, heart rate, systolic blood pressure. [3]Quantitative nasopharyngeal SARS-CoV-2 RNA testing (RT-PCR): nasopharyngeal or throat swabs are used; any FDA-approved or commercial testing method is acceptable. [4]Standard labs: serum chemistry, coagulation tests and hematology. [5]Blood draws: serum and peripheral blood mononuclear cells for later immunological analysis. [6]Immunology tests: COVID-19 relevant immunology labs. [7]Quantitative blood SARS-CoV-2 antibody testing: Blood samples are used; any FDA-approved or commercial testing method is acceptable. [8]WHO 9-point scale: see description of secondary end points for details. [9]Day 1 (i.e., the first day of drug intake) is most likely also the screen/enroll day; subjects receive a phone call from Study Team a few hours after first dose is taken to check up on how they are doing. [10]ET: Subjects who prematurely discontinue study drug for any reason are asked to have an Early Termination (ET) visit the day the last study drug dose was taken.

DETAILED DESCRIPTION OF THE INVENTION

The role of the inflammasome/caspase1/pyroptosis axis as a key inflammatory pathway in the context of coronavirus infections and beyond is well known in the art. Furthermore, the relevance of the inflammasome/caspase1/pyroptosis axis specifically in COVID-19 is also known in the art. Therefore, clinical data that provides a *nexus* between the inflammasome/caspase1/pyroptosis axis and COVID-19 provides insight for treating COVID-19 by targeting pathways in the inflammasome/caspase1/pyroptosis axis.

The liver disease and transplant communities provide a window into populations that are especially important to study in light of coronavirus disease 2019 (COVID-19) as these patients typically have many co-morbidities, including diabetes, obesity and related cardiac issues, cancer, and most notably end-stage organ failure. What these co-morbidities have in common is underlying chronic inflammation involving activation of the inflammasome (Guo H, Callaway J B, Ting J P. Inflammasomes: mechanism of action, role in disease, and therapeutics. Nat Med 2015; 21:677-687). What these patients have in common is lethal experiences with COVID-19 (Onder G, Rezza G, Brusaferro S. Case-Fatality Rate and Characteristics of Patients Dying in Relation to COVID-19 in Italy. JAMA 2020). Putting these two factors together caused Applicants to speculate that the inflammasome, and more specifically pyroptosis, are what may drive tragic outcomes for patients with co-morbidities in the face of COVID-19. Applicants observed this phenomenon in a liver transplant patient with several co-morbidities, who rapidly succumbed to the disease, and whose clinical course and immunological phenotype are described in Example 1. Applicants' finding has been corroborated with at least ten other patients.

Applicants' findings shed new light on why and how SARS-CoV-2 infections cause such rapid lethality. T cell lymphopenia and lack of COVID specific IgM indicates that the adaptive immune system never properly kicked in. Caspase-1 overexpression in lymphocytes suggests pyroptosis as one of the possible mechanisms of T-cell depletion and functional abnormalities of other lymphocytes (Doitsh et al. Nature 2014; 505:509-514).

Applicants propose that the inflammatory response is secondary to the danger signals from pyroptotic cell death of immune system cells, resulting in a heightened inflammation compared to the one induced by apoptotic tissue cells. The end result is likely a self-damaging shut down of the immune system that further fuels the inflammation created by the viral infection. Applicants provide data backed connection between caspase-1 and COVID-19, a connection with significant therapeutic implications as rather than inhibition of the inflammatory response, preventing the pyroptotic lymphocyte death fueling the inflammation becomes more critical.

Figure 1:
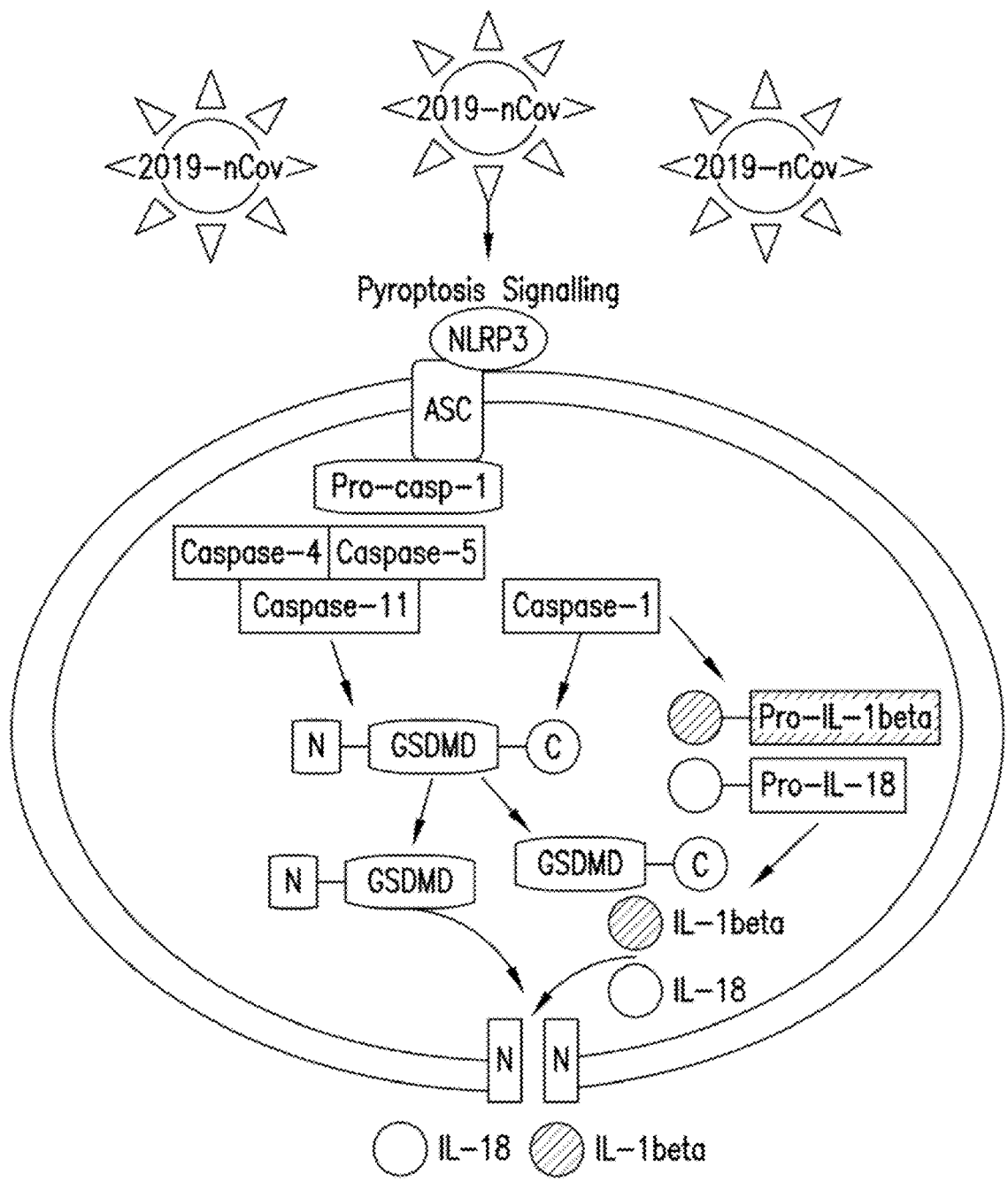
FIG. 1: A hypothesis of the relationship between 2019-nCoV and cell pyroptosis set forth in Yang (Cell Pyroptosis, a Potential Pathogenic Mechanism of 2019-nCoV Infection (Jan. 29, 2020). Available at SSRN: https://ssrn.com/abstract=3527420 or http://dx.doi.org/10.2139/ssrn.3527420).

Based upon knowledge of the inflammasome/caspase1/pyroptosis axis as a key inflammatory pathway in the context of coronavirus infections and the hypotheses regarding COVID-19, clinical data showing inflammasome activation, and more specifically increased levels of lactate dehydrogenase (LDH) Rayamajhi et al. Methods Mol Biol 2013; 1040:85-90 and overexpression of caspase-1 and pyroptosis, confirms the hypothesis set forth in FIG. 1.

By targeting key components of the inflammasome/caspase1/pyroptosis axis to minimize or prevent pyroptosis, Applicants believe the onset and/or severity of lymphophenia, hyperinflammation of other immune cells include monocytes and subsequently COVID-19 is delayed and/or mitigated and possibly prevented.

Rodrigues et al. (J. Exp. Med. 2020 Vol. 218 No. 3 https://rupress.org/jem/article/218/3/e20201707/211560/Inflammasomes-are-activated-in-response-to-SARS) found that the NLRP3 inflammasome is activated in response to SARS-CoV-2 infection and is active in COVID-19 patients by studying moderate and severe COVID-19 patients, they found active NLRP3 inflammasome in PBMCs and tissues of postmortem patients upon autopsy. Inflammasome-derived products such as Casp1p20 and IL-18 in the sera correlated with the markers of COVID-19 severity, including IL-6 and LDH. Moreover, higher levels of IL-18 and Casp1p20 are associated with disease severity and poor clinical outcome. Their results suggest that inflammasomes participate in the pathophysiology of the disease, indicating that these platforms might be a marker of disease severity and a potential therapeutic target for COVID-19.

Todo et al. (Inflammation Research (2021) 70:7-10 https://doi.org/10.1007/s00011-020-01413-2) also identified the presence of NLRP3 inflammasome aggregates in the lungs of fatal COVID-19 pneumonia thus providing the potential molecular link between viral infection and cytokine release syndrome.

Sars-CoV-2-induced caspase1 activation and pyroptosis is confirmed in monocytes, which may be as important as in lymphocytes (see, e.g., https://www.nature.com/articles/s41420-021-00428-w.pdf). There is not only upregulation of caspase1 in SARS-CoV-2 infected monocytes but also effective inhibition of resulting pyroptosis via a caspase1 inhibitor.

Potential inhibitors of NLRP3 inflammasome and their targets are set forth in the below table (see Zahid et al. (2019) Front. Immunol. 10:2538 doi: 10.3389/fimmu.2019.02538), all of which are contemplated as pharmaceutical compounds for treating COVID-19 in the present invention.

| Agent | Target(s) | Potential mechanism |
|---|---|---|
| Glyburide | NLRP3 (indirectly) | Inhibits ATP-sensitive $K^+$ channels; downstream of P2X7 resulting in inhibition of ASC aggregation |
| 16673-34-0 | NLRP3 (indirectly) | Induces NLRP3 conformational changes secondary to its activation or binding to ASC |
| JC124 | NLRP3? | Blocks the expression of NLRP3, ASC, caspase-1, pro-IL-1β, TNFα and iNOS |
| FC11A-2 | NLRP3 (indirectly) | Interferes with proximity induced autocleavage of pro-caspase-1, suppresses IL-1β/18 release |
| Parthenolide | NLRP1, NLRP3 inflammasome, Caspase-1, NF-κB, IKKβ kinase activity | Alkylates cysteine residues in caspase-1 and in ATPase domain of NLRP3, inhibits NLRP3 ATPase activity |
| VX-740 | Caspase-1 | Covalent modification of the catalytic cysteine residue in the active site of caspase-1 resulting in caspase-1 blocking and resultant cleavage of pro-IL-1β/18 |
| VX-765 | Caspase-1 | Covalent modification of the catalytic cysteine residue in the active site of caspase-1 resulting in caspase-1 blocking and resultant cleavage of pro-IL-1β/18 |
| Bay 11-7082 | NLRP3, IKK, E2/3 enzymes, PTPs | Alkylates the cysteines in the ATPase domain of NLRP3, inhibits NLRP3 ATPase activity |
| BHB | NLRP3 (Indirectly) | Inhibits $K^+$ efflux resulting in reduced oligomerization of ASC and IL-1β/18 release |
| MCC950 | NLRP3 | Blocks the ATPase domain of NLRP3 resulting in inhibition of canonical and non-canonical NLRP3 inflammasome activation |
| MNS | NLRP3 | Inhibits NLRP3 ATPase activity by cysteine modification, blocks NLRP3 inflammasome activation |
| CY-09 | NLRP3 | Inhibits NLRP3 ATPase activity, blocks NLRP3 inflammasome activation |
| Tranilast | NLRP3 | Binds to NLRP3 NACHT domain to block NLRP3-NLRP3 and NLRP3-ASC interaction |
| OLT1177 | NLRP3 | Inhibits NLRP3 ATPase activity, blocks NLRP3 inflammasome activation |
| Oridonin | NLRP3 | Binds to cysteine 279 of NLRP3 to abolish NLRP3-NEK7 interaction, blocks NLRP3 inflammasome activation |

The present invention relates to determining if a patient is infected with SARS-CoV-2 and whether there is pyroptotic activity in the cells of the patient. For determining infection, a molecular or viral test, usually RT-PCR, is preferred over a serological or antibody test. For determining pyroptotic activity, markers such as NLRP3, IL-1δ, gasdermin D (GSDMD) and/or caspase 1 are screened at either the nucleic acid or protein level wherein elevated levels of any of the markers are indicative of pyroptosis.

If a patient tests positive for COVID-19, then the patient is treated with an effective amount of one or more compounds that inhibit one or more pathways of the inflammasome/caspase 1/pyroptosis axis.

Caspase-1 has been identified to be a key enzyme in the inflammasome/caspase1/pyroptosis axis because caspase-1 both activates gasdermin and activates IL-1β and IL-18. Caspase-1 is also known as the interleukin-converting enzyme (ICE).

Prospective clinical applications of caspase inhibitors are set forth in the below table (see Kudelova et al., JPP No 4/2015 article 01 http://jpp.krakow.pl/journal/archive/08_15/articles/01_article.html)

| DRUGS company | STRUCTURE AND SUBSTRATE SPECIFITY | PRECLINICAL DATA | CLINICAL TRIALS | CLINICAL TRIALS RUNNING/TERMINATED |
|---|---|---|---|---|
| Pralnacasan VX-740 Vertex Pharmaceuticals | Prodrug of orally active reversible peptidomimetic casp-1 inhibitor | Collagenase-induced OA (27) Type II collagen-induced arthritis in mice Dextran sulfate sodium-induced colitis in mice (101) | Rheumatoid arthritis and osteoarthritis (significant amelioration of RA, but not OA) | Terminated in Phase IIb in RA due to liver toxicity in animals (102) |
| Belnacasan VX-765 Vertex Pharmaceuticals | Prodrug of orally active reversible peptidomimetic casp-1 inhibitor | Mouse models of acute seizures and chronic epilepsy (134) Dermatitis model Arthritis model (103) Prevents CD4 T-cell pyroptotic death in a dose-dependent manner in HIV-infected lymphoid tissues (136) | Completed Phase II in psoriasis Completed Phase II in resistant partial epilepsy Evaluated the efficacy and safety Phase IIb in resistant partial epilepsy | Any results released Terminated Phase IIb due to lack of efficacy |
| Nivocasan GS-9450 Gilead Sciences | Orally active irreversible peptidomimetic casp-1, -8, -9 inhibitor | Fibrosis/apoptosis animal models Bleomycin induced pulmonary fibrosis in mice (132) | Completed Phase II in NASH Completed Phase IIa in chronic HCV Evaluated the efficacy and safety Phase II in chronic HCV for 6 months | Reductions in ALT levels in NASH patients (6) Terminated Phase IIb due to significant laboratory abnormalities and adverse events in a number of clinical study participants |
| Emricasan IDN-6556 Conatus Pharmaceuticals | Orally active broad spectrum irreversible peptidomimetic caspase inhibitor | α-F as model of apoptotic hepatitis in mice Bile duct ligated model of liver failure, injury, fibrosis in mice (133) Post transplantation-liver, islets (7) Models of NASH, NAFLD (133, 135) | Completed Phase II in treatment HCV Completed Phase II of safety and efficacy in patients undergoing liver transplantation | Efficacy in post liver transplant for chronic HCV (108, 109) Pharmacokinetics and pharmacodynamics Phase II in ACLF (111) Efficacy and safety Phase II in NAFLD and raised transaminases Terminated Phase II in severe AH and contraindications to steroid therapy due to inadequate dose of Emricasan Safety Phase I/II in islet transplantation in type I diabetic participants (112) Pharmacokinetics and pharmacodynamics Phase I in subjects with severe renal impairment and matched healthy volunteers Pharmacokinetics and pharmacodynamics Phase I in subjects with hepatic impairment and matched healthy volunteers |

The present invention particularly relates to a caspase 1/interleukin-1β converting enzyme (ICE) inhibitor in its prodrug form (VX-765), also known as RVT-201, or in its active form (see, e.g., WO01/90063, U.S. Pat. Nos. 7,417, 029, 8,329,662, 9,156,880, 9,487,555, 9,994,613, and US20200048306, the disclosures of which are incorporated by reference) in treating COVID-19. In addition to COVID-19, the compound and pharmaceutical compositions thereof are useful as agents to treat interleukin-1-(IL-1), apoptosis-, other forms of cell death such as pyroptotic cell death and necrotic cell death, interferon-6 (IL-6), interferon-17 (IL-17), interferon-18-(IL-18), interferon-γ (IFNγ) or tumor necrosis factor-α (TNFα) mediated disease, including inflammatory diseases, autoimmune diseases, destructive bone disorders, proliferative disorders, infectious diseases, and degenerative diseases. This invention also relates to methods for inhibiting caspase 1/ICE activity and decreasing IL-18 production and IFN-γ production and methods for treating interleukin-1, apoptosis-, and interferon-γ-mediated diseases using the compositions of this invention. The compound is represented by formula I (VX-765):

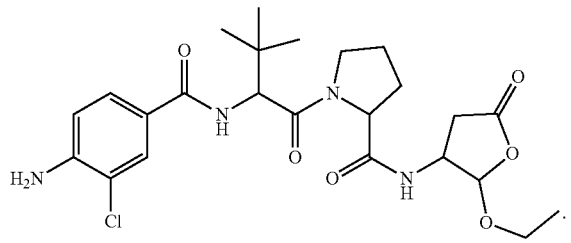

I

Compound I (VX-765) may be used alone or in combination with other therapeutic or prophylactic agents, such as antibiotics, antivirals, immunomodulators, or other anti-inflammatory agents, for the treatment or prevention of diseases mediated by NLRP3, IL-1, pyroptosis, apoptosis, IL-6, IL-18, IFNγ, or TNF-α. This invention also relates to pharmaceutically acceptable derivatives and prodrugs of the compound.

Compound I (VX-765) itself is a prodrug that undergoes bioconversion to an active caspase 1/ICE inhibitor II:

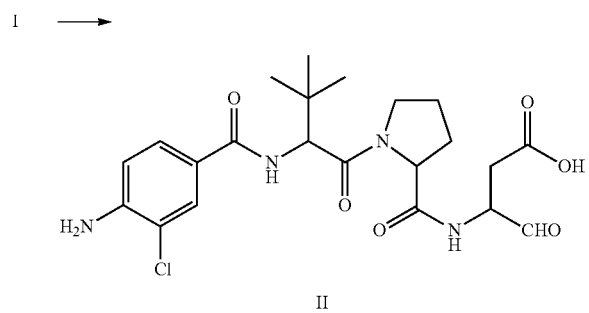

II

Compound I (VX-765) has better in vivo activity upon oral and/or intravenous administration than the parent or active form of the drug. The active form, aspartic aldehyde II, exhibits less than optimal in vivo activity, primarily because of poor bioavailability, and is therefore not well-suited for direct therapeutic use.

VX-765 is advantageously formulated as a solution or a tablet (see, e.g., Wannamaker et al., WET 321:509-516, 2007; Stack et al., J. Immunol 205; 175:2630-2634 and Bialer et al., Epilepsy Research (2013) 103, 2-30). The dosage of VX-765 may be about 10 to 100 mg/kg, such as about 10 mg/kg, about 12.5 mg/kg, about 25 mg/kg, about 50 mg/kg, about 75 mg/kg or about 100 mg/kg. If formulated as a liquid, VX-765 is dissolved in about 20% to about 25% Kolliphor® or any other suitable polyethoxylated castor oil. A tablet of VX-765 may be about 300 mg per tablet with daily dosage of about 900 mg to about 3600 mg. The above dosages may be extrapolated to other pharmaceutical compositions of the present invention.

In another embodiment, VX-740 (pralnacasan) is also contemplated for the present invention. Pralnacasan is an orally bioavailable pro-drug of a potent, non-peptide inhibitor of caspase 1/ICE having the structure:

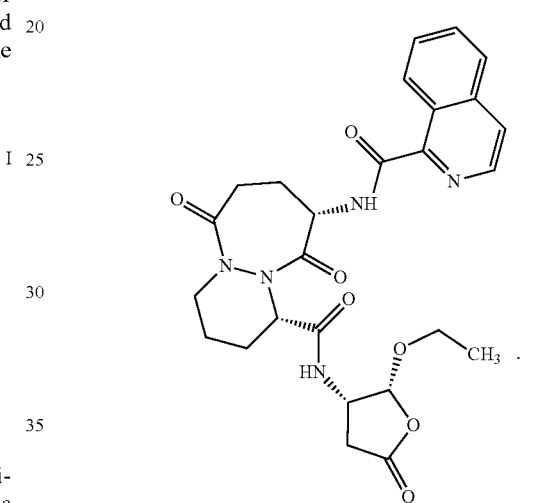

Other caspase 1/ICE inhibitors are contemplated for the present invention, such as Conatus' lead caspase 1 inhibitor CTS-2090.

Additional caspase 1/ICE inhibitors contemplated for the present invention are presented below and set forth in WO 2017/079566:

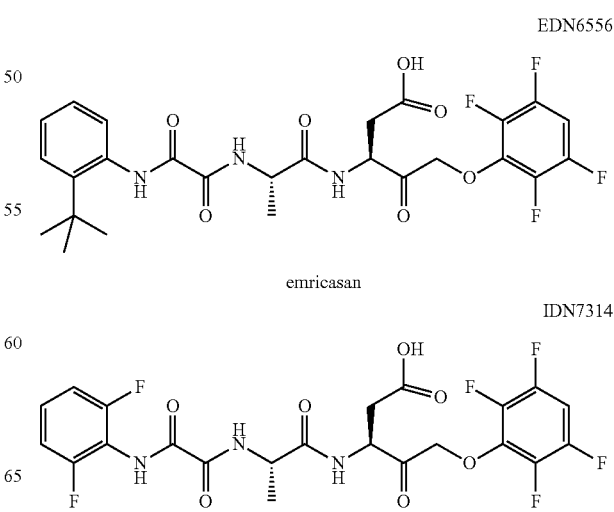

emricasan

IDN7314

IDN6734

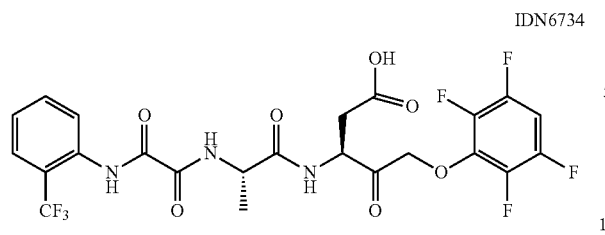

CTS-8931

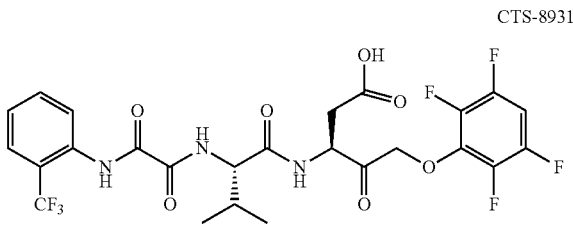

CTS5814

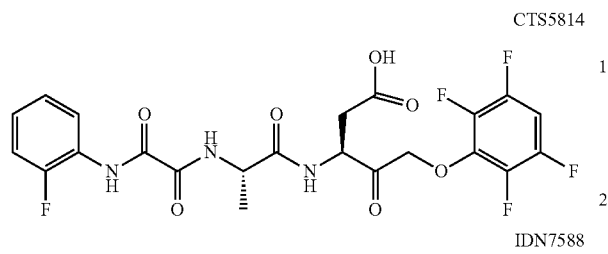

QVD-OPh

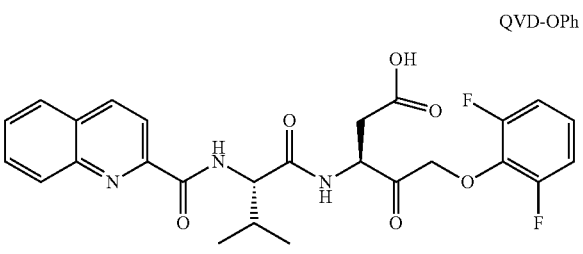

IDN7588

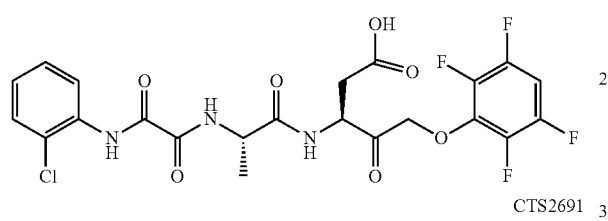

VX$_{105}$

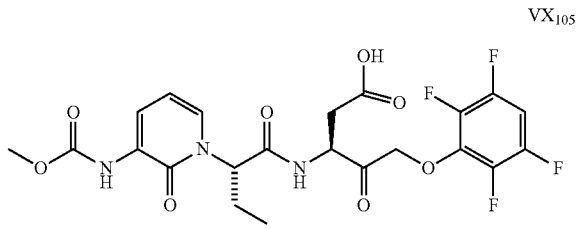

CTS2691

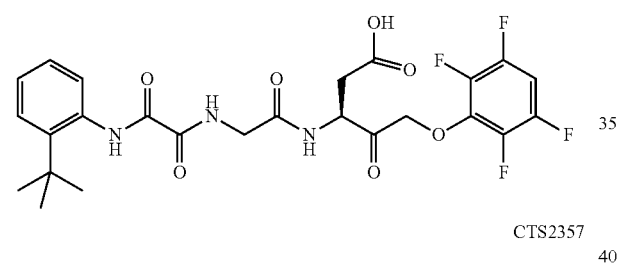

IDN8126

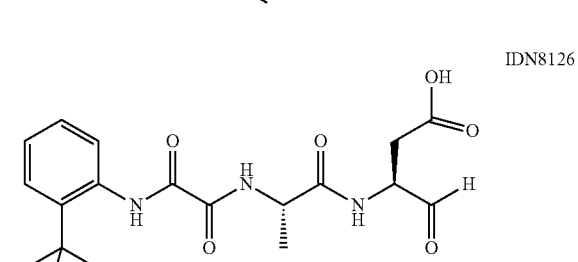

CTS2357

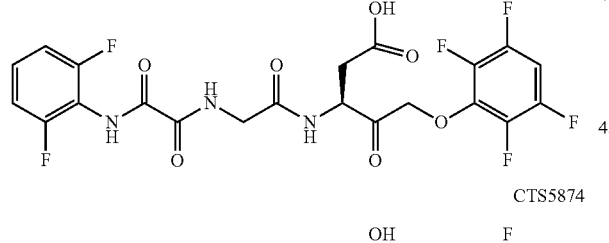

IDN9103

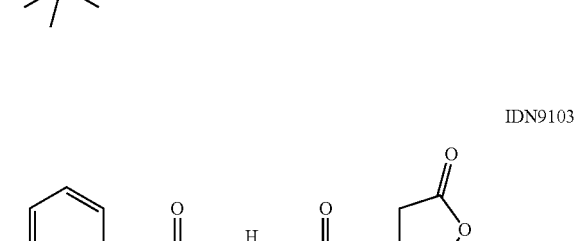

CTS5874

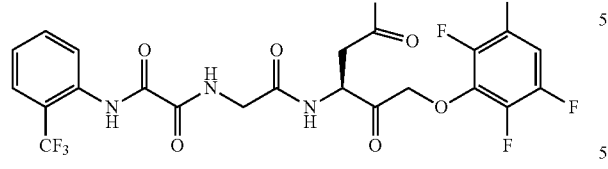

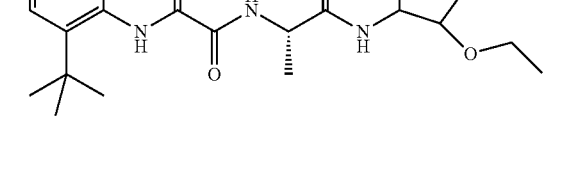

CTS7186

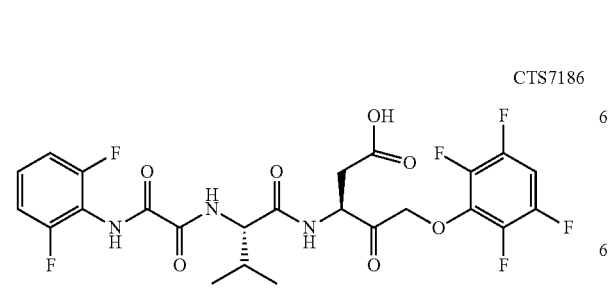

In another embodiment, an IL-1β blocking agent may be administered by itself or in combination with a caspase 1/ICE inhibitor. Examples of IL-1β blocking agents include, but are not limited to, Canakinumab (Ilaris®), Anakinra (Kineret®) and Rilonacept (Arcalyst®).

In yet another embodiment, the pharmaceutical composition of the present invention may be administered in combination with another therapeutic agent, advantageously one used for COVID-19. Examples of such candidate drug treatments in Phase III-IV trials are presented in the below table.

| Drug candidate | Description | Existing disease approval | Trial sponsor(s) | Location(s) | Expected results |
| --- | --- | --- | --- | --- | --- |
| Remdesivir | antiviral; adenosine nucleotide analog inhibiting RNA synthesis in coronaviruses | investigational[77] | Gilead, WHO, INSERM | China, Japan initially; expanded internationally in Global Solidarity and Discovery Trials | April (Chinese, Japanese trials) to mid-2020 |
| Hydroxychloroquine or chloroquine | antiparasitic and antirheumatic; generic made by many manufacturers | malaria, rheumatoid arthritis, lupus (International)[83][84] | CEPI, WHO, INSERM | Multiple sites in China; Global Solidarity and Discovery Trials, Europe, international | April 2020 (Chinese trials); mid-2020 |
| Favipiravir | antiviral against influenza | influenza (China)[86] | Fujifilm | China | April 2020 |
| Lopinavir/ritonavir without or with Rebif | antiviral, immune suppression | investigational combination; lopinavir/ritonavir approved[88] | CEPI, WHO, UK Government, Univ. of Oxford, INSERM | Global Solidarity and Discovery Trials, multiple countries | mid-2020 |
| Sarilumab | human monoclonal antibody against interleukin-6 receptor | rheumatoid arthritis (USA, Europe)[89] | Regeneron-Sanofi | Multiple countries | Spring 2020 |
| ASC-09 + ritonavir | antiviral | combination not approved; ritonavir approved for HIV[88] | Ascletis Pharma | Multiple sites in China | Spring 2020 |
| Tocilizumab | human monoclonal antibody against interleukin-6 receptor | immunosuppression, rheumatoid arthritis (USA, Europe)[92] | Genentech-Hoffmann-La Roche | Multiple countries | mid-2020 |
| Dapagliflozin | sodium-glucose cotransporter 2 inhibitor | hypoglycemia agent[94] | Saint Luke's Mid America Heart Institute, AstraZeneca | Multiple countries | December 2020 |
| CD24Fc | antiviral immunomodulator against inflammatory response | new drug candidate | OncoImmune, Inc. | Multiple sites in the United States | 2021 |

Other Drugs used for COVID (see, e.g., Yu Peng, Hongxun Tao, Senthil Kumaran Satyanarayanan, Kunlin Jin, Huanxing Su. A Comprehensive Summary of the Knowledge on COVID-19 Treatment Aging Dis. 2021 February; 12(1): 155-191. Published online 2021 Feb. 1. doi: 10.14336/AD.2020.1124. PMCID: PMC7801274 and Shagufta, Irshad Ahmad. The race to treat COVID-19: Potential therapeutic agents for the prevention and treatment of SARS-CoV-2. Eur J Med Chem. 2021 Mar. 5; 213: 113157. Published online 2021 Jan. 12. doi: 10.1016/j.ejmech.2021.113157. PMCID: PMC7802596). Apart from the direct action of the SARS-Cov 2 virus cytokines have a direct role in the immunopathogenesis of COVID-19 by inducing hyper inflammation and lung injury that defines this disease and the severe phenotype. Monocytes and macrophages have an important role in respiratory failure during COVID-19; these cells migrate to the lungs, producing pro-inflammatory cytokines, and inducing epithelial damage. COVID-19 patients present an impaired immune response due to exhausted phenotype and lower effector T cells, CD8+T lymphocytes, and NK cells, culminating in antiviral immunity loss. While vaccines are now available a proportion of individuals continue to develop a severe phenotype, either from vaccine failure or not being vaccinated. The following are a guide to potential and actual therapies that may mitigate the effects of the virus directly or by reducing the inflammatory consequences.

Vitamin supplementation enhances immune response: Vitamin A, D, E and C, selenium and zinc. The above supplements have a variety of effects including immune modulation, particularly vitamin D, improving recovery from viral infections, vitamins A and E and zinc and an antioxidant effect selenium and vitamin C. They may have a role in immune "exhaustion".

Polyclonal (pAbs) and monoclonal (mAbs) antibody-based immunotherapy. Monoclonal Abs are primarily manufactured however pAbs are from pooled human blood products also known as convalescent plasma (CP) or immune plasma. Antibodies prevent the virus from entering the host cells, blocking receptor ACE2 and directly on the virus (neutralizing antibodies [nAbs] recognize epitopic regions of SARS-CoV-2). On the virus, they prevent its infectivity by activating several pathways, such as the complement system, cell cytotoxicity, and phagocytic clearance. The therapeutic use of mAbs extends to the use of many that block or otherwise modulate part of the antibody cascade. These include anti-JAK, anti-GM-CSF, anti-GM-CSF receptor, anti-M-CSF receptor, anti-CD14, anti-IFN?, anti-VEGF, anti-BKT, anti-CCR5, anti-IL-6, anti-IL-6 receptor, anti-TNFa, anti-IL1ß, anti-IL1ß receptor, and complement C5 inhibitor. Some antibody drugs are being used to disrupt critical complication that increase morbiditiy and include the hyper-thrombotic state found in critically ill patients by using anti-P-selectin, anti-CTGF, and factor XIIa antagonist mAbs. to restore the exhausted T lymphocytes' and NK cells' immunity, anti-PD1 mAbs. Another therapeutic strategy using antibodies is intravenous immunoglobulin (IVIg) that contains polyclonal IgG isolated from healthy donors, which can be further enhanced by using IgG antibodies collected from recovered COVID-19 patients in the same geographical region as the patient.

Immune cell-based therapy: NK and T cells including CART, stem cells from any source and related products. A viable approach is the use of allogeneic human leukocyte antigen-matched umbilical cord-derived Tregs (UBC-Treg) which can be widely expanded and used on a larger scale.

Cytokine use in relation T-cells includes IL-7 to increase CD4+ and CD8+T lymphocyte counts without inducing the production of pro-inflammatory mediators.

Antivirals: lopinavir/ritonavir, arbidol, ribavirin, remdesivir, favipiravir, sofosbuvir and type I IFN. Ribavirin has been used in association with lopinavir/ritonavir to treat SARS-CoV-1 and other antivirals such as sofosbuvir can strongly bind to coronavirus. Remdesivir (RDV) originally developed to treat Ebola virus infection, RDV is active against RNA viruses from different families, including Coronaviridae (e.g., SARS-CoV-1 and MERS-CoV). IFN-α2b has been used in many regimens including stand alone protocols.

Parenteral or enteral malaria chemoprevetion: chloroquine and hydroxychloroquine with or without macrolide antibiotics. Part of the WHO model list of essential medicines, immunomodulatory they also show broad-spectrum antiviral effects. Hydroxychloroquine-azithromycin combinations have been used.

Parenteral, or enteral antihelminthics: ivermectin, niclosamide, nitazoxanide. Ivermectin, the best known and most widely used antiparasitic drug in human and veterinary medicine has been tried against SARS-CoV-2. Niclosamide, an old anthelmintic used to treat tapeworm infections, and an antiprotozoal agent, nitazoxanide is another broad-spectrum antiviral agent considered for treatment of COVID-19.

Parenteral, or enteral anticoagulants: heparin, warfarin, clopidogrel, rivaroxaban, ticagrelor, fondapariniux, argatroban. A high mortality risk in severe COVID-19 patients related to coagulopathy. In addition, heparin has an anti-inflammatory effect that can bind to inflammatory cytokines, chemokines, and proinflammatory proteins, inhibiting neutrophil chemotaxis and leukocyte migration Parenteral, or enteral broad spectrum corticosteroids: dexamethasone, methylprednisolone, prednisolone, prednisone and hydrocortisone. These are broad anti-T-cell therapies. There is good evidence for use of dexamethasone early.

Other Drugs used as antivirals or as anti-inflammatory agents. These include colchicine, sotretinoin, apremilast, and zanubrutinib.

Emricasan (a pan-caspase) inhibitor is also contemplated as a therapeutic agent for COVID-19 (see, e.g., https://www.medrxiv.org/content/10.1101/2020.11.02.20223636v1.full and https://www.globenewswire.com/news-release/2020/10/27/2115049/0/en/Histogen-and-Amerimmune-Enter-into-a-Collaborative-Development-and-Commercialization-Agreement-for-Emricasan-in-the-Treatment-of-COVID-19.html).

Other potential therapeutic agents for COVID-19 treatment are summarized by Shagufta (European Journal of Medicinal Chemistry 213 (2021) 113157 https://doi org/10.1016/j.ejmech.2021.113157), which include antiogensin-converting enzyme-2 (ACE-2) inhibitors such as chloroquine and hydroxychloroquine, N-(2-aminoethyl)-1 aziridine-ethanamine, GW280264X, TAPI-0 and TAPI-2, MLN-4760, HTC and HMHTCC, telmisartan, and recombinant human antiotensin-converting enzyme 2; SARS-CoV-2 3CL protease inhibitors such as lopinavir and ritonavir, N3, Compound 21 and 22, α-ketoamides, and N-substituted isatin compounds; spike glycoprotein inhibitors such as S1 subunit: RBD inhibitors such as SSAA09E2, K22 and rilapladib, S2 inhibitors such as TGG, luteolin and quercetin, ADS-J1 and arbidol; cathepsin L proteinase inhibitors such as CID 23631927 and CID 16725315, SSAA09E1, MDL28170, and K11777; transmembrane serine protease 2 inhibitors such as camostat; furin cleavage site inhibitors such as decanoyl-RVKR-chloromethylketone; and RNA-dependent RNA polymerase inhibitors such as remdesir and favipiravir.

van den Berg and to Velde ((2020) Severe COVID-19: NLRP3 Inflammasome Dysregulated. Front. Immunol. 11:1580. doi: 10.3389/fimmu.2020.01580) propose a two pronged treatment: to reduce virus entry and help to eradicate the virus by boosting the immune system and in an inflammation-driven damaging phase the endogeneous adjuvant reaction of the immune system should be suppressed. Potential targets include an NLRP3 inflammasome inhibitor, HMGB1, reducing the number of neutrophils, and blocking downstream mediators of NLRP3, such as caspase-1 and cytokines IL-1β and IL-18 and their receptors.

de Rivero Vaccari et al. ((2020) The Inflammasome in Times of COVID-19. Front. Immunol. 11:583373. doi: 10.3389/fimmu.2020.583373) provide therapies targeting the inflammasome that could be used in the care of COVID-19 patients that are presented below:

| Therapy | Mechanism of action |
|---|---|
| Dexamethasone | Decreases airway inflammation by inhibiting NLRP inflammasome activation and levels of IL-1β and IL-18 |
| Enoxaparin | Low molecular weight heparin shown to inhibit inflammasome activation in a mouse model of brain injury-induced ALI. |
| IFN-β | Type I IFNs decreased NLRP3 inflammasome activation through STAT1 |
| MCC950 | Inhibits inflammasome activation by preventing NLRP3 oligomerization |
| IC100 | Inhibits inflammasome activation by preventing ASC-speck formation |
| M5049 | Inhibits TLR7 and TLR8, which have been described in inflammasome activation |
| Anakinra | IL-1 receptor blocker |
| Tocilizumab | Therapeutic monoclonal antibody that blocks IL-6 signaling |

Yap et al. (J Immunol 2020; 205:307-312; Prepublished online 3 June http://www.jimmunol.org/content/205/2/307 doi: 10.4049/jimmunol.2000513 2020) discuss available pharmaceutical agents that target a critical component of inflammasome activation, signaling leading to cellular pyroptosis, and the downstream cytokines as a promising target for the treatment of severe coronavirus disease 2019-associated diseases.

Lopez-Reyes et al. ((2020) Front. Immunol. 11:570251. doi: 10.3389/fimmu.2020.570251) review the molecular mechanisms by which obesity-associated systemic inflammation could cause a more severe clinical presentation of COVID-19 and hypothesize the SARS-CoV-2 infection could potentiate or accelerate the pre-existing systemic inflammatory state of individuals with obesity, via the NLRP3 inflammasome activation and the release of pro-inflammatory cytokines from cells trough Gasdermin-pores commonly found in cell death by pyroptosis.

Quagliariello et al. (European Review for Medical and Pharmacological Sciences 2020; 24: 9169-9171) argue that targeting NLRP3 inflammasome could be a strategy to prevent cardiovascular outcomes [fulminant myocarditis, heart failure, venous thoromboembolism (VTE)] and acute respiratory distress syndrome (ARDS) in patients with SARSCoV-2 infection. They discuss the rational for NLRP3 targeting in clinical trials as an effective therapeutic strategy aimed to improve prognosis of COVID-19, analyzing the potential of two therapeutic options (tranilast and OLT1177) currently available in clinical practice.

Lopes et al. (medRxiv preprint doi: https://doi.org/10.1101/2020.08.06.20169573) evaluate the addition of colchicine to standard treatments for COVID-19.

Combined use of different treatments in COVID-19 are presented in Table 2 of Peng et al., Aging and Disease Volume 12, Number 1, February 2021 and reproduced below.

| Treatment | Drug | Drug target | Dosage | Source |
|---|---|---|---|---|
| Arbidol + Bromhexine | Arbidol | Membrane fusion inhibitor | PO | NCT04273763 (CN) |
| | Bromhexine | Expectorant | PO | |
| Arbidol + IFN-β1α | Arbidol | Membrane fusion inhibitor | PO, 200 mg, tid, 14 d | NCT04254874 (CN) |
| | IFN-β1α | Immunomodulator | INH, 14 d | |
| Chloroquine + Ivermectin | Chloroquine | Membrane fusion inhibitor and immunomodulator | PO | NCT04382846 (EG) |
| | Ivermectin | Importin (IMP) α/β receptor | PO | |
| Chloroquine + Ivermectin + Vitamin D | Chloroquine | Membrane fusion inhibitor and immunomodulator | PO, 500 mg, 4 d, 30 d | NCT04399746 (MX) |
| | Ivermectin | IMP α/β receptor | PO, 6 mg, qd, Day 1, 7 and 8 | |
| | Vitamin D | Vitamins | PO, 400 UI bid | |
| Chloroquine + Losartan | Chloroquine | Membrane fusion inhibitor and immunomodulator | PO, 450 mg, bid | NCT04428268 (MX) |
| | Losartan | Angiotensin II receptor (type AT1) antagonis | PO, 25 mg, bid | |
| Chloroquine + Zinc | Chloroquine | Membrane fusion inhibitor and immunomodulator | PO | NCT04447534 (EG) |
| | Zinc | | PO | |
| Hydroxychloroquine + Azithromycin | Hydroxychloroquine | —/Receptor binding and membrane fusion inhibitor | PO, 400 mg, bid, 7 d | NCT04321278 (IL) NCT04322123 (BR) |
| | Azithromycin | Tetrcycline | PO, 500 mg, qd | NCT04329832 (US) |
| Hydroxychloroquine + Azithromycin +/− tocilizumab | Hydroxychloroquine | Membrane fusion inhibitor and immunomodulator | PO, 800 mg, qd | NCT04347031 (RU) |
| | Azithromycin | Tetrcycline | PO, 250 mg, bid | |
| | Tocilizumab | Anti-IL-6R antibody | IV | |
| Hydroxychloroquine + Azithromycin + Convalescent plasma | Hydroxychloroquine | Membrane fusion inhibitor and immunomodulator | PO, 400 mg, bid, 5 d | NCT04441424 (IQ) |
| | Azithromycin | Tetrcycline | PO, 500 mg, qd, 5 d | |
| | Convalescent plasma | Immunomodulator | IV, 400 mL, 5 d | |
| Hydroxychloroquine + Azithromycin + Oseltamivir | Hydroxychloroquine | Membrane fusion inhibitor and immunomodulator | PO, 200 mg, tid, 5 d | NCT04338698 (BR) NCT04338698 (PK) |
| | Azithromycin | Tetrcycline | PO, 500 mg, Day 1; 250 mg, Day 2-5 | |
| | Oseltamivir | Nucleoside analog | PO, 75 mg, bid, 5 d | |
| Hydroxychloroquine + Azithromycin + Sarilumab | Hydroxychloroquine | Membrane fusion inhibitor and immunomodulator | PO, 200 mg, tid | NCT04341870 (FR) |
| | Azithromycin | Tetrcycline | PO, 500 mg, Day 1; 250 mg, Day 2-5 | |
| | Sarilumab | Anti-1L-6R antibody | IV, 400 mg, Day 1 | |
| Hydroxychloroquine + Azithromycin + zinc | Hydroxychloroquine | Membrane fusion inhibitor and immunomodulator | PO, 600 mg, Day 1, 200 mg, Day 2-9 | NCT04528927 (TN) |
| | Azithromycin | Tetrcycline | PO, 500 mg, Day 1; 250 mg, Day 2-5 | |
| | Zinc | | PO, 220 mg, 10 d | |
| Hydroxychloroquine + Baricitinib | Hydroxychloroquine | Membrane fusion inhibitor and immunomodulator | PO, 200 mg, tid, 14 d | NCT04373044 (US) |
| | Baricitinib | JAK inhibitor | PO, 2 mg, qd, 14 d | |
| Hydroxychloroquine + Bromhexine | Hydroxychloroquine | Membrane fusion inhibitor and immunomodulator | PO, 200 mg, tid | NCT04273763 (CN) NCT04340349 (MX) |
| | Bromhexine | Expectorant | PO, 8 mg, tid | |
| Hydroxychloroquine + Camostat mesylate | Hydroxychloroquine | Membrane fusion inhibitor and immunomodulator | PO, 400 mg, bid, 10 d | NCT04355052 (IL) |
| | Camostat mesylate | TMPRSS2 inhibitor | PO, 200 mg, qd, 10 d | |
| Hydroxychloroquine + Clindamycin | Hydroxychloroquine | Membrane fusion inhibitor and immunomodulator | PO, 200 mg, tid, 7 d | NCT04349410 (US) |
| | Clindamycin | Lincomycin antibiotics | IV, 4800 mg | |
| Hydroxychloroquine + Clindamycin + Primaquine | Hydroxychloroquine | Membrane fusion inhibitor and immunomodulator | PO, 200 mg, tid, 7 d | NCT04349410 (US) |
| | Clindamycin | Lincomycin antibiotics | IV, 4800 mg, 7 d | |
| | Primaquine | Membrane fusion inhibitor and immunomodulator | PO, 200 mg, qd, 7 d | |
| Hydroxychloroquine + Daclatasvir + Sofosbuvir | Hydroxychloroquine | Membrane fusion inhibitor and immunomodulator | PO, 400 mg, bid, 14 d | NCT04443725 (EG) |
| | Daclatasvir | Nucleoside analog | PO, 90 mg, qd, 14 d | |
| | Sofosbuvir | Nucleoside analog | PO, 400 mg, qd, 14 d | |
| Hydroxychloroquine + Doxy cy dine | Hydroxychloroquine | Membrane fusion inhibitor and immunomodulator | PO, 200 mg, tid, 10 d | NCT04349410 (US) |
| | Doxycycline | Tetrcycline | IV, 100 mg, bid, 10 d | |
| Hydroxychloroquine + Favipiravir | Hydroxychloroquine | Membrane fusion inhibitor and immunomodulator | PO, 200 mg, bid, 7 d | NCT04359615 (IR) NCT04376814 (IR) |
| | Favipiravir | Nucleoside analog | PO, 1600 mg, Day 1, 600 mg, tid, 7 d | |
| Hydroxychloroquine + IFN-α2β | Hydroxychloroquine | Membrane fusion inhibitor and immunomodulator | PO | NCT04273763 (CN) |
| | IFN-α2β | Immunomodulator | INH | |
| Hydroxychloroquine + Imatinib | Hydroxychloroquine | Membrane fusion inhibitor and immunomodulator | PO, 200 mg, bid | NCT04346147 (ES) |
| | Imatinib | TMPRSS2 inhibitor | PO, 400 mg, qd | |

-continued

| Treatment | Drug | Drug target | Dosage | Source |
|---|---|---|---|---|
| Hydroxychloroquine + Indomethacin + Azithromycin | Hydroxychloroquine | Membrane fusion inhibitor and immunomodulator | PO, 200 mg, bid, 7 d | NCT04344457 (US) |
| | Indomethacin | Nonsteroidal anti-inflammatory drug | PO, 50 mg, tid, 14 d | |
| | Zithromax | Tetrcycline | PO, 500 mg, qd, 3 d | |
| Hydroxychloroquine + Lopinavir + Ritonavir + IFN-β1α | Hydroxychloroquine | Membrane fusion inhibitor and immunomodulator | PO | NCT04350684 (IR) NCT04343768 (IR) NCT04350671 (IR) |
| | Lopinavir | Nucleoside analog | PO | |
| | Ritonavir | Nucleoside analog | PO | |
| | IFN-β1α | Immunomodulator | IV | |
| Hydroxychloroquine + Lopinavir + Ritonavir | Hydroxychloroquine | Membrane fusion inhibitor and immunomodulator | PO, 200 mg, bid | NCT04390152 (CO) NCT04346147 (ES) |
| | Lopinavir | Nucleoside analog | PO, 200 mg, qd | |
| | Ritonavir | Nucleoside analog | PO, 50 mg, qd | |
| Hydroxychloroquine + Lopinavir + Ritonavir + IFN-β1β | Hydroxychloroquine | Membrane fusion inhibitor and immunomodulator | PO | NCT04343768 (IR) |
| | Lopinavir | Nucleoside analog | PO | |
| | Ritonavir | Nucleoside analog | PO | |
| | IFN-β1β | Immunomodulator | PO | |
| Hydroxychloroquine + Oseltamivir | Hydroxychloroquine | Membrane fusion inhibitor and immunomodulator | PO, 200 mg, bid, 5 d | NCT04338698 (PK) NCT04303299 (TH) |
| | Oseltamivir | Nucleoside analog | PO, 75 mg, bid, 5 d | |
| Hydroxychloroquine + Sirolimus f | Hydroxychloroquine | Membrane fusion inhibitor and immunomodulator | PO, 600 mg, 10 d | NCT04374903 (JO) |
| | Sirolimus | Immunosuppressant | PO, 250 mg, 10 d | |
| Hydroxychloroquine + Tofacitinib | Hydroxychloroquine | Membrane fusion inhibitor and immunomodulator | PO, 200 mg, tid, 14 d | NCT04390061 (US) |
| | Tofacitinib | JAK inhibitor | PO, 10 mg, bid, 14 d | |
| Azithromydn + Amoxicillin | Azithromycin | Tetrcycline | PO, 500 mg, Day 1; 250 mg, Day 2-5, 2 d | NCT04363060 (FR) |
| | Amoxicillin/Clavulanate | Antibacterial drugs | PO, 250 mg, tid, 2 d | |
| Azithromycin + Atovaquone | Azithromycin | Tetrcycline | PO, 500 mg, Day 1; 250 mg, Day 2-5 | NCT04339426 (US) |
| | Atovaquone | | PO, 750 mg, bid, 10 d | |
| Azithromycin + Clavulanate | Azithromycin Clavulanate | Tetrcycline | PO, 250 mg, tid, 7 d | NCT04363060 (FR) |
| Azithromycin + Doxycycline | Azithromycin | Tetrcycline | PO, 500 mg, Day 1; 250 mg, Day 2-5 | NCT04528927 (TN) |
| | Doxycycline | Tetrcycline | PO, 200 mg, qd, 10 d | |
| Azithromycin + Ivermectin + Nitazoxanide | Azithromycin | Tetrcycline | PO | NCT04382846 (EG) |
| | Ivermectin | IMP α/β receptor | PO | |
| | Nitazoxanide | Immunomodulator | PO | |
| Azithromycin + Mefloquine +/− Tocilizumab | Azithromycin | Tetrcycline | PO, 250 mg, tid, 7 d | NCT04347031 (RU) |
| | Mefloquine | Membrane fusion inhibitor and immunomodulator | PO, 500 mg, bid, 7 d | |
| | Tocilizumab | Anti-IL-6R antibody | IV | |
| Azithromycin + Nitazoxanide | Azithromycin | Tetrcycline | PO | NCT04382846 (EG) |
| | Nitazoxanide | Immunomodulator | PO | |
| Azithromycin + Oseltamivir | Azithromycin | Tetrcycline | PO, 500 mg, Day 1; 250 mg, Day 2-5 | NCT04338698 (PK) |
| | Oseltamivir | Nucleoside analog | PO, 75 mg, bid | |
| Azythromycin + Ivermectin + Dutasteride | Azythromycin | Tetrcycline | PO, 500 mg, qd | NCT04446429 (BR) |
| | Ivermectin | IMP α/β receptor | PO, 200 mcg/kg, qd | |
| | Dutasteride | TMPRSS2 inhibitor | PO, 0.5 mg | |
| Azithromycin + Ivermectin + Proxalutamide | Azithromycin | Tetrcycline | PO, 500 mg, qd | NCT04446429 (BR) |
| | Ivermectin | IMP α/β receptor | PO, 200 mcg/kg, qd | |
| | Proxalutamide | TMPRSS2 inhibitor | PO, 200 mg | |
| Ivermectin + Doxycycline | Ivermectin | IMP α/β receptor | PO, 200 mcg/kg, qd, 5 d | NCT04407130 (BD) NCT04523831 (BD) NCT04403555 (EG) |
| | Doxycycline | Tetrcycline | PO, 200 mg, 5 d | |
| Ivermectin + Dutasteride + | Ivermectin | IMP α/β receptor | PO, 200 mcg/kg, qd | NCT04446429 (BR) |
| | Dutasteride | TMPRSS2 inhibitor | PO, 0.5 mg | |
| Ivermectin + Losartan | Ivermectin | IMP α/β receptor | PO, 12 mg, qd, 15 d | NCT04447235 (BR) |
| | Losartan | Angiotensin II receptor (type AT1) antagonis | PO, 50 mg, qd, 15 d | |
| Ivermectin + Nitazoxanide | Ivermectin | IMP α/β receptor | PO | NCT04382846 (EG) |
| | Nitazoxanide | Immunomodulator | PO | |
| Ivermectin + Nitazoxanide + Ribavirin | Ivermectin | IMP α/β receptor | PO, 7 d | NCT04392427 (EG) |
| | Nitazoxanide | Immunomodulator | PO, 7 d | |
| | Ribavirin | Nucleoside analog | PO, 7 d | |
| Ledipasvir + Sofosbuvir | Ledipasvir | Nucleoside analog | PO, 90 mg, qd, 14 d | NCT04498936 (EG) |
| | Sofosbuvir | Nucleoside analog | PO, 400 mg, qd, 14 d | |
| Daclatasvir + Sofusbuvir | Daclatasvir | Nucleoside analog | PO, 120 mg, Day 1; 60 mg, Day 2-9 | NCT04468087 (BR) NCT04460443 (EG) |
| | Sofusbuvir | Nucleoside analog | PO, 800 mg, Day 1; 400 mg, Day 2-9 | |

-continued

| Treatment | Drug | Drug target | Dosage | Source |
|---|---|---|---|---|
| Danoprevir + Ritonavir | Danoprevir | Nucleoside analog | PO, 100 mg, bid, 10 d | NCT04345276 (CN) |
| | Ritonavir | Nucleoside analog | PO, 100 mg, bid | NCT04291729 (CN) |
| Darunavir + Cobicistat | Darunavir | Viral RNA-dependent RNA polymerase inhibitor/CYP3A protein inhitor | PO, 800 mg, qd, 5 d | NCT04252274 (CN) NCT04425382 (QA) |
| | Cobicistat | Protease inhibitor | PO, 150 mg, qd, 5 d | |
| Darunavir + Ritonavir + Favipiravir + Hydroxychloroquine | Darunavir | Nucleoside analog | PO, 400 mg, tid | NCT04303299 (TH) |
| | Ritonavir | Nucleoside analog | PO, 200 mg, qd | |
| | Favipiravir | Nucleoside analog | PO, 2400 mg, qd | |
| | Hydroxychloroquine | Membrane fusion inhibitor and immunomodulator | PO, 800 mg, qd | |
| Darunavir + Ritonavir + Oseltamivir + Hydroxychloroquine | Darunavir | Nucleoside analog | PO, 400 mg, tid | NCT04303299 (TH) |
| | Ritonavir | Nucleoside analog | PO, 200 mg, qd | |
| | Oseltamivir | Nucleoside analog | PO, 300 mg, qd | |
| | Hydroxychloroquine | Membrane fusion inhibitor and immunomodulator | 8 PO, 00 mg, qd | |
| Darunavir + Ritonavir + Oseltamivir | Darunavir | Nucleoside analog | PO, 400 mg, tid | NCT04303299 (TH) |
| | Ritonavir | Nucleoside analog | PO, 200 mg, qd | |
| | Oseltamivir | Nucleoside analog | PO, 300 mg, qd | |
| Emtricitabine + Tenofovir | Emtricitabine | Protease inhibitor | PO, 300 mg, qd, 8 d | NCT04519125 (CO) |
| | Tenofovir | Nucleoside analog | PO, 200 mg, qd | |
| Emtricitabine + Tenofovir Alafenamide | Emtricitabine | Protease inhibitor | PO, 200 mg, qd | NCT04405271 (AR) |
| | Tenofovir alafenamide | Nucleoside analog | PO, 25 mg, qd | |
| Favipiravir + Maraviroc | Favipiravir | Nucleoside analog | PO, 200 mg, qd, 10 d | NCT04475991 (MX) |
| | Maraviroc | Chemokine receptor antagonist | PO, 300 mg, qd, 10 d | |
| Favipiravir + Tocilizumab | Favipiravir | Nucleoside analog | PO, 1600 mg, Day 1,600 mg, tid, 6 d | NCT04310228 (CN) |
| | Tocilizumab | Anti-IL-6R antibody | IV, 4-8 mg/kg, 7 d | |
| Oseltamivir + ASC09F | Oseltamivir | RdRP inhibitor | PO, 75 mg, qd, 14 d | NCT04261270 (CN) |
| | ASC09F | CYP3A4 inhibitor | PO, 400 mg, bid, 14 d | |
| Oseltamivir + Mesenchymal stem cells | Oseltamivir | Nucleoside analog | PO, 4 w | NCT04371601 (CN) |
| | Mesenchymal stem cells | MSC therapy | IV, 1 × 10$^6$ cell/kg/w, 4 w | |
| Oseltamivir + Ritonavir | Oseltamivir | Viral RNA-dependent RNA/ Booster of other protease polymerase inhibitor | PO, 75 mg, qd, 7 d | NCT04315896 (MX) NCT04318444 (US) NCT04328285 (FR) |
| | Ritonavir | Nucleoside analog | PO, 300 mg, bid, 7 d | |
| Lopinavir + Ritonavir | Lopinavir | Anti-retroviral of the protease inhibitor/booster of other protease inhibitors | PO, 400 mg, bid, 5 d | Guidelines (version 7) for treatment of COVID-19 |
| | Ritonavir | Nucleoside analog | PO, 100 mg, bid, 5 d | NCT04328285 (FR) NCT04328012 (US) |
| Lopinavir + Ritonavir + Arbidol | Lopinavir | Anti-retroviral of the protease inhibitor/booster of other protease inhibitors | PO, 400 mg, bid, 5-21 d | NCT04350671 (IR) NCT04403100 (BR) NCT04376814 (IR) |
| | Ritonavir | Nucleoside analog | PO, 100 mg, bid, 5-21 d | |
| | Arbidol | Membrane fusion inhibitor and immunomodulator/Anti- retro viral of the protease inhibitor/booster of other protease | PO, 200 mg, tid, 5-21 d | |
| Lopinavir + Ritonavir + Atorvastatin | Lopinavir | Anti-retroviral of the protease inhibitor/booster of other protease inhibitors | PO, 200 mg, qd, 10 d | NCT04466241 (FR) |
| | Ritonavir | Nucleoside analog | PO, 50 mg, qd, 10 d | |
| | Atorvastatin | Statin medication | PO, 20 mg, qd, 10 d | |
| Lopinavir + Ritonavir + Favipiravir | Lopinavir | Anti-retroviral of the protease inhibitor/booster of other protease inhibitors | PO, 400 mg, bid, 7 d | NCT04499677 (GB) NCT04303299 (TH) |
| | Ritonavir | Nucleoside analog | PO, 100 mg, bid, 7 d | |
| | Favipiravir | Nucleoside analog | PO, 1800 mg, bid, Day 1; 400 mg, 4 times, 7 d | |
| Lopinavir + Ritonavir + IFN-β1α | Lopinavir | Anti-retroviral of the protease inhibitor/booster of other protease inhibitors | PO, 200 mg, qd | NCT04315948 (FR) NCT04276688 (CN) |
| | Ritonavir | Nucleoside analog | PO, 50 mg, qd | |
| | IFN-β1α | Immunomodulator | INH, 44 μg/0.5 mL | |
| Lopinavir + Ritonavir + Oseltamivir | Lopinavir | Anti-retroviral of the protease inhibitor/booster of other protease inhibitors | PO, 800 mg, qd | NCT04303299 (TH) |
| | Ritonavir | Nucleoside analog | PO, 200 mg, qd | |
| | Oseltamivir | Nucleoside analog | PO, 300 mg, qd | |
| Lopinavir + Ritonavir + Telmisartan | Lopinavir | Anti-retroviral of the protease inhibitor/booster of other protease inhibitors | PO, 200 mg, qd, 10 d | NCT04466241 (FR) |
| | Ritonavir | Nucleoside analog | PO, 50 mg, qd, 10 d | |
| | Telmisartan | Angiotensin II receptor (type AT1) antagonis | PO, 40 mg, qd, 10 d | |

| Treatment | Drug | Drug target | Dosage | Source |
|---|---|---|---|---|
| Lopinavir + Ritonavir + Ribavirin + IFN-β1α | Lopinavir | Anti-retroviral of the protease inhibitor/booster of other protease inhibitors | PO, 400 mg, bid, 14 d | NCT04276688 (CN) NCT04343768 (IR) |
| | Ritonavir | Nucleoside analog | PO, 100 mg, bid, 14 d | |
| | Ribavirin | Nucleoside analog | PO, 400 mg, bid, 14 d | |
| | IFN-β1α | Immunomodulator | SC, 0.25 mg | |
| Remdesivir + Apremilast | Remdesivir | Nucleoside analog | PO, 200 mg, qd, Day 1; 100 mg, qd, Day 2-9 | NCT04488081 (US) |
| | Apremilast | Antiemetic | PO, 30 mg, bid, 9 d | |
| Remdesivir + Cenicriviroc | Remdesivir | Nucleoside analog | PO, 200 mg, qd, Day 1; 100 mg, qd, Day 2-9 | NCT04488081 (US) |
| | Cenicriviroc | CCR5 inhibitor | PO, 150 mg, bid, 28 d | |
| Remdesivir + Baricitinib | Remdesivir | Nucleoside analog | PO, 200 mg, qd, Day 1; 100 mg, qd, Day 2-9 | NCT04401579 (US) |
| | Baricitinib | JAK inhibitor | PO, 4 mg, qd, 14 d | |
| Remdesivir + Icatibant | Remdesivir | Nucleoside analog | PO, 200 mg, qd, Day 1; 100 mg, qd, Day 2-9 | NCT04488081 (US) |
| | Icatibant | Peptide-based hormone | SC, 30 mg, 9 d | |
| Remdesivir + IFN-β1α | Remdesivir | Nucleoside analog | PO, 200 mg, qd, Day 1; 100 mg, qd, Day 2-9 | NCT04492475 (US) |
| | IFN-β1α | Immunomodulator | SC, 44 µg/0.5 mL | |
| Remdesivir + Merimepodib | Remdesivir | Nucleoside analog | PO, 200 mg, qd, Day 1; 100 mg, qd, Day 2-9 | NCT04410354 (US) |
| | Merimepodib | Inosine monophosphate dehydrogenase (IMPDH) inhibitor | IV, 400 mg, tid, 10 d | |
| Remdesivir + NA-831 | Remdesivir | Nucleoside analog | PO, 1 mg/kg | NCT04480333 (US) |
| | NA-831 | Endogenous small molecule | INH, 0.2 mg/kg | |
| Remdesivir + Razuprotafib | Remdesivir | Nucleoside analog | PO, 200 mg, qd, Day 1; 100 mg, qd, Day 2-9 | NCT04488081 (US) |
| | Razuprotafib | VE-PTP inhibitor | SC, 10 mg, tid, 7 d | |
| Remdesivir + Tocilizumab | Remdesivir | Nucleoside analog | PO, 10 d | NCT04409262 (US) |
| | Tocilizumab | Anti-IL-6R antibody | IV, 10 d | |
| Ribavirin + Sofosbuvir | Ribavirin | Nucleoside analog | PO | NCT04460443 (EG) |
| | Sofosbuvir | Nucleoside analog | PO | |
| Ritonavir + ASC09 | Ritonavir | Nucleoside analog | PO, 100 mg, bid, 14 d | NCT04261907 (CN) |
| | ASC09 | Protease inhibitors | PO, 300 mg, bid, 14 d | |
| Ritonavir + Ganovo + IFN-Nebulization | Ritonavir | Nucleoside analog | PO, 100 mg, bid, 14 d | NCT04291729 (CN) |
| | Danoprevir | Nucleoside analog | PO, 100 mg, bid, 14 d | |
| | IFN-Nebulization | Immunomodulator | INH, 50 µg, bid, 14 d | |
| IFN-α1β + Thymosin α1 | IFN-α1β | Immunomodulator | ISIN, 2-3 drops, 4 times | NCT04320238 (CN) |
| | Thymosin α1 | Immunomodulator | SC, 1 time per week | |
| IFN-β1β + clofazimine | IFN-β1β | Immunomodulator | SC or IV, 16 million UI, 3 d | NCT04465695 (CN) |
| | Clofazimine | Nucleoside analog | PO, 100 mg, bid | |
| Adalimumab + Tocilizumab | Adalimumab | Humanized monoclonal antibody against the TNF-alpha | Adalimumab: SC, 40 mg, every 2 weeks; Tocilizumab: IV, 8 mg/kg, 6 times in 4 weeks | ChiCTR2000030580 |
| | Tocilizumab | Anti-IL-6R antibody | IV | |
| | C486 | — | SC or IV | |
| REGN10933 + REGN10987 | REGN10933 | Anti-Spike (S) SARS-CoV-2 antibody | SC or IV | NCT04426695 (US) NCT04519437 (US) NCT04452318 (US) |
| Tocilizumab + Dexamethasone | Tocilizumab | Anti-IL-6R antibody | IV, 8 mg/kg, Day 1 and 3 | NCT04476979 (GF) |
| | Dexamethasone | Corticosteroids | IV, 10 mg for 5 d, 2.5 mg for 4 d | |
| Tocilizumab + Methylprednisolone | Tocilizumab | Anti-IL-6R antibody | IV, 8 mg/kg, Day 1 and 3 | NCT04377503 (ES) |
| | Methylprednisolone | Corticosteroids | IV, 1.5 mg/kg/d, 21 d | |
| Tocilizumab + Pembrolizumab | Tocilizumab | Anti-IL-6R antibody | IV, 8 mg/kg | NCT04335305 (ES) |
| | Pembrolizumab | PD-1 antibody | IV, 200 mg | |
| Toremifene + Melatonin | Toremifene | Hormone | PO, 60 mg, qd | NCT04531748 (US) |
| | Melatonin | Hormone | PO, 40 mg, morning; 60 mg, evening | |
| Anakinra + Ruxolitinib | Anakinra | 1L antagonists | IV, 300 mg/d, 5 d | NCT04366232 (FR) |
| | Ruxolitinib | JAK inhibitor | PO, 5 mg, bid, 14-28 d | |
| Anakinra + Siltuximab | Anakinra | 1L antagonists | SC, 100 mg, qd | NCT04330638 (BE) |
| | Siltuximab | Anti-IL-6R antibody | IV, 11 mg/kg | |
| Anakinra + Tocilizumab | Anakinra | 1L antagonists | SC, 100 mg, qd | NCT04330638 (BE) |
| | Tocilizumab | Anti-IL-6R antibody | IV, 8 mg/kg | |
| Colchicine + Edoxaban | Colchicine | NLRP Inflammasome inhibitor | PO, 0.5 mg, qd | NCT04516941 (CH) |
| | Edoxahan | Thrombolytic medication | PO, 60 mg, qd | |
| Colchicine + Methylprednisolone | Colchicine | NLRP Inflammasome inhibitor | PO, 0.5 mg, qd, 14 d | NCT04492358 (ES) |
| | Methylprednisolone | Corticosteroids | PO, 60 mg, qd, 3 d | |
| Colchicine + Rosuvastatin | Colchicine | NLRP Inflammasome inhibitor | PO, 0.6 mg, qd, 3 d | NCT04472611 (US) |
| | Rosuvastatin | HMG-CoA reductase inhibitors | PO, 40 mg, qd, 3 d | |

-continued

| Treatment | Drug | Drug target | Dosage | Source |
|---|---|---|---|---|
| Dexamethasone + Placenta-Derived MMSC | Dexamethasone Placenta-Derived MMSCs | Corticosteroids MSC therapy | IV IV, 1 × 10^6 cell/kg, Day 1, 4 and 7 | NCT04461925 (UA) |
| Diltiazem + Niclosamide | Diltiazem Niclosamide | Calcium-channel blocker — | PO, 500 mg × 4 times, 10 d PO, 60 mg, tid, 10 d | NCT04372082 (FR) |
| Dipyridamole + Aspirin | Dipyridamole Aspirin | Thrombolytic medication Thrombolytic medication | PO, 200 mg, qd, 14 d PO, 25 mg, qd, 14 d | NCT04410328 (US) |
| Enoxaparin + Methylprednisolone | Enoxaparin Methylprednisolone | Thrombolytic medication Corticosteroids | SC, 4000-6000 UI IV, 0.5 mg/kg | NCT04528888 (IT) |
| Heparin + Methylprednisolone | Heparin Methylprednisolone | Thrombolytic medication Corticosteroids | IV, 18 UI/kg/h IV, 0.5 mg/kg | NCT04485429 (BR) NCT04528888 (IT) |
| Heparin + Umbilical Cord Mesenchymal Stem Cells | Heparin Umbilical Cord Mesenchymal Stem Cells | Thrombolytic medication MSC therapy | IV IV, 100 × 10^6 cell | NCT04355728 (US) |
| Levamisole + Isoprinosine | Levamisole Isoprinosine | — — | PO, 50 mg, tid, 14 d PO, 1 g, 4 times | NCT04383717 (EG) NCT04360122 (EG) |
| Metenkefalin + Tridecactide | Metenkefalin Tridecactide | Opioid delta receptor agonists Th1 cell modulators | IV, 5 mg IV, 1 mg | NCT04374032 (YU) |
| Nitazoxanide + atazanavir + ritonavir | Nitazoxanide Atazanavir Ritonavir | Immunomodulator Nucleoside analog Nucleoside analog | PO, 1000 mg, bid PO, 300 mg, qd PO, 100 mg, qd | NCT04459286 (NG) |
| Paracetamol + ChAdOx1 nCoV-19 | Paracetamol ChAdOx1 nCoV-19 | Non-steroidal anti-inflammatory drugs Vaccine | PO, IV, 5 × 10^10 vp | NCT04324606 (GB) |
| Paracetamol + MenACWY | Paracetamol MenACWY | Non-steroidal anti-inflammatory drugs Vaccine | IV IV | NCT04324606 (GB) |
| Ruxolitinib + Simvastatin | Ruxolitinib Simvastatin | JAK inhibitor Statin medication | PO, 5 mg, bid, 14 d PO, 40 mg, qd, 14 d | NCT04348695 (ES) |
| SnPP Protoporphyrin + Sunlight exposure | SnPP Protoporphyrin Sunlight exposure | Photodynamic therapy | IV, 5, 7 and 9 mg, 14 d 1 h, 14 d | NCT04371822 (EG) |
| Sulfonatoporphyrin(TPPS) + Sunlight exposure | Sulfonatoporphyrin(TPPS) Sunlight exposure | Photodynamic therapy | IV, 5 mg, 14 d 1 h, 14 d | NCT04371822 (EG) |
| Tacrolimus + Methylprednisolone | Tacrolimus Methylprednisolone | Immunosuppressant Corticosteroids | PO, 8-10 ng/mL blood level PO, 120 mg, 3 d | NCT04341038 (ES) |
| Tirofiban + Clopidogrel + Acetylsalicylic acid + Fondaparinux | Tirofiban Clopidogrel Acetylsalicylic add Fondaparinux | Thrombolytic medication Thrombolytic medication Thrombolytic medication Thrombolytic medication | IV, 0.15 µg/kg/min PO, initial dose of 300 mg, then 75 mg/d IV, initial dose of 75 mg, then 30 mg/d IV, 2.5 mg | NCT04368377 |

PO: Oral administration;
IV: Intravenous administration;
INH: Inhalation;
IM: intramuscular administration;
SC: Subcutaneous administration;
ISIN: Intrasinal administration;
ID: intradermal injection;
SL: Sublingual administration;
TOPp: patch applied on the skin;
ET: Endotracheal instillation Pharmaceutical compositions of this invention may comprise a compound of VX-765 or any other caspase 1/ICE inhibitor or a pharmaceutically acceptable salt thereof and a pharmaceutically acceptable carrier. Such compositions may optionally comprise an additional therapeutic agent. Such agents include, but are not limited to, an anti-inflammatory agent, a matrix metalloprotease inhibitor, a lipoxygenase inhibitor, a cytokine antagonist, an immunosuppressant, an anti-cancer agent, an anti-viral agent, a cytokine, a growth factor, an immunomodulator, a prostaglandin, or an anti-vascular hyperproliferation compound.

The term "pharmaceutically acceptable carrier" refers to a non-toxic carrier that may be administered to a patient, together with a compound of this invention, and which does not destroy the pharmacological activity thereof.

Pharmaceutically acceptable carriers that may be used in the pharmaceutical compositions of this invention include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, wool fat and self-emulsifying drug delivery systems (SEDDS) such as .alpha.-tocopherol, polyethyleneglycol 1000 succinate, or other similar polymeric delivery matrices.

In pharmaceutical composition comprising only a caspase 1/ICE inhibitor as the active component, methods for administering these compositions may additionally comprise the step of administering to the subject an additional agent. Such agents include, but are not limited to, an anti-inflammatory agent, a matrix metalloprotease inhibitor, a lipoxygenase inhibitor, a cytokine antagonist, an immunosuppressant, an anti-cancer agent, an anti-viral agent, a cytokine, a growth factor, an immunomodulator, a prostaglandin, or an anti-vascular hyperproliferation compound.

The term "pharmaceutically effective amount" refers to an amount effective in treating or ameliorating an IL-1-, apoptosis-, other forms of cell death such as pyroptotic cell death and necrotic cell death-, IL-6, IL-17-, IL-18-, IFN-γ- or TNF-α-mediated disease in a patient. The term "prophylactically effective amount" refers to an amount effective in preventing or substantially lessening IL-1-, apoptosis-, other forms of cell death such as pyroptotic cell death and necrotic cell death-, IL-6, IL-17-, IL-18-, IFN-γ- or TNF-α-mediated disease in a patient.

The compounds of this invention may be employed in a conventional manner for controlling IL-18 and IFN-γ levels in vivo and for treating diseases or reducing the advancement or severity of effects which are mediated by IL-1, apoptosis, other forms of cell death such as pyroptotic cell death and necrotic cell death, IL-6, IL-17, IL-18, IFN-γ or TNF-α-. Such methods of treatment, their dosage levels and requirements may be selected by those of ordinary skill in the art from available methods and techniques.

For example, a compound of this invention may be combined with a pharmaceutically acceptable adjuvant for administration to a patient suffering from an IL-1-, apoptosis-, other forms of cell death such as pyroptotic cell death and necrotic cell death, IL-6, IL-17-, IL-18-, IFN-γ- or TNF-α-mediated disease in a pharmaceutically acceptable manner and in an amount effective to lessen the severity of that disease.

Alternatively, the compounds of this invention may be used in compositions and methods for treating or protecting individuals against IL-1, apoptosis-, other forms of cell death such as pyroptotic cell death and necrotic cell death, IL-6, IL-17-, IL-18-, IFN-γ- or TNF-α-mediated diseases over extended periods of time. The compounds may be employed in such compositions either alone or together with other compounds of this invention in a manner consistent with the conventional utilization of enzyme inhibitors in pharmaceutical compositions. For example, a compound of this invention may be combined with pharmaceutically acceptable adjuvants conventionally employed in vaccines and administered in prophylactically effective amounts to protect individuals over an extended period of time against IL-1-, apoptosis-, other forms of cell death such as pyroptotic cell death and necrotic cell death, IL-6, IL-17-, IL-18-, IFN-γ- or TNF-α-mediated disease.

The caspase 1/ICE inhibitor(s) may also be co-administered with other caspase 1 inhibitors to increase the effect of therapy or prophylaxis against various IL-1-, apoptosis-, other forms of cell death such as pyroptotic cell death and necrotic cell death, IL-6, IL-17-, IL-18-, IFN-γ- or TNF-α-mediated diseases.

In addition, the compounds of this invention may be used in combination with either conventional anti-inflammatory agents or with matrix metalloprotease inhibitors, lipoxygenase inhibitors and antagonists of cytokines other than IL-1β.

The compounds of this invention can also be administered in combination with immunomodulators (e.g., bropirimine, anti-human alpha-interferon antibody, IL-2, GM-CSF, anti-GMCSF monoclonal antibodies (such as, for example Gimsilumab from Roivant), methionine enkephalin, interferon-alpha, diethyldithiocarbamate, tumor necrosis factor, naltrexone, and EPO), with prostaglandins, or with antiviral agents (e.g., 3TC, remdesivir, polysulfated polysaccharides, ganiclovir, ribavirin, acyclovir, alpha interferon, trimethotrexate, and fancyclovir) or prodrugs of these or related compounds to prevent or combat IL-1-mediated disease symptoms such as inflammation.

When the compounds of this invention are administered in combination therapies with other agents, they may be administered sequentially or concurrently to the patient. Alternatively, pharmaceutical or prophylactic compositions according to this invention comprise a combination of a caspase 1/ICE inhibitor and another therapeutic or prophylactic agent.

The pharmaceutical compositions of this invention may be administered orally, parenterally, by inhalation spray, topically, rectally, nasally, buccally, vaginally, or via an implanted reservoir. In an advantageous embodiment, the administration is oral administration. The pharmaceutical compositions of this invention may contain any conventional non-toxic pharmaceutically-acceptable carriers, adjuvants or vehicles. In some cases, the pH of the formulation may be adjusted with pharmaceutically acceptable acids, bases or buffers to enhance the stability of the formulated compound or its delivery form. The term parenteral as used herein includes subcutaneous, intracutaneous, intravenous, intramuscular, intra-articular, intrasynovial, intrasternal, intrathecal, intralesional, and intracranial injection or infusion techniques.

The pharmaceutical compositions may be in the form of a sterile injectable preparation, for example, as a sterile injectable aqueous or oleaginous suspension. This suspension may be formulated according to techniques known in the art using suitable dispersing or wetting agents (such as, for example, Tween 80) and suspending agents. The sterile injectable preparation may also be a sterile injectable solution or suspension in a non-toxic parenterally-acceptable diluent or solvent, for example, as a solution in 1,3-butanediol. Among the acceptable vehicles and solvents that may be employed are mannitol, water, Ringer's solution and isotonic sodium chloride solution. In addition, sterile, fixed oils are conventionally employed as a solvent or suspending medium. For this purpose, any bland fixed oil may be employed including synthetic mono- or diglycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, such as those described in Pharmacopeia Helvetica, or a similar alcohol.

The pharmaceutical compositions of this invention may be orally administered in any orally acceptable dosage form including, but not limited to, capsules, tablets, and aqueous suspensions and solutions. In the case of tablets for oral use, carriers which are commonly used include lactose and corn starch. Lubricating agents, such as magnesium stearate, are also typically added. For oral administration in a capsule form, useful diluents include lactose and dried corn starch. When aqueous suspensions and solutions and propylene glycol are administered orally, the active ingredient is combined with emulsifying and suspending agents. If desired, certain sweetening and/or flavoring and/or coloring agents may be added.

The pharmaceutical compositions of this invention may also be administered in the form of suppositories for rectal administration. These compositions can be prepared by mixing a compound of this invention with a suitable non-irritating excipient which is solid at room temperature but liquid at the rectal temperature and therefore melt in the rectum to release the active components. Such materials include, but are not limited to, cocoa butter, beeswax and polyethylene glycols.

Topical administration of the pharmaceutical compositions of this invention is especially useful when the desired treatment involves areas or organs readily accessible by topical application. For application topically to the skin, the pharmaceutical composition should be formulated with a suitable ointment containing the active components suspended or dissolved in a carrier. Carriers for topical administration of the compounds of this invention include, but are not limited to, mineral oil, liquid petroleum, white petroleum, propylene glycol, polyoxyethylene polyoxypropylene compound, emulsifying wax, and water. Alternatively, the pharmaceutical composition can be formulated with a suitable lotion or cream containing the active compound suspended or dissolved in a carrier. Suitable carriers include, but are not limited to, mineral oil, sorbitan monostearate, polysorbate 60, cetyl esters wax, cetearyl alcohol, 2-octyldodecanol, benzyl alcohol and water. The pharmaceutical compositions of this invention may also be topically applied to the lower intestinal tract by rectal suppository formulation or in a suitable enema formulation. Topically-administered transdermal patches are also included in this invention.

The pharmaceutical compositions of this invention may be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other solubilizing or dispersing agents known in the art.

Dosage levels of between about 0.01 and about 100 mg/kg body weight per day, preferably between 0.5 and about 75 mg/kg body weight per day and most preferably between about 1 and 50 mg/kg body weight per day of the active ingredient compound are useful in a monotherapy for the prevention and treatment of IL-1-, apoptosis-, other forms of cell death such as pyroptotic cell death and necrotic cell death, IL-6, IL-17-, IL-18-, IFN-γ- or TNF-α-mediated diseases, including uveitis, inflammatory diseases, autoimmune diseases, destructive bone disorders, proliferative disorders, infectious diseases, degenerative diseases, necrotic diseases, inflammatory peritonitis, osteoarthritis, acute pancreatitis, chronic pancreatitis, asthma, adult respiratory distress syndrome, glomerulonephritis, rheumatoid arthritis, systemic lupus erythematosus, scleroderma, chronic thyroiditis, Graves' disease, autoimmune gastritis, insulin-dependent diabetes mellitus (Type I), autoimmune hemolytic anemia, autoimmune neutropenia, thrombocytopenia, chronic active hepatitis, myasthenia gravis, inflammatory bowel disease, Crohn's disease, psoriasis, atopic dermatitis, graft vs. host disease, osteoporosis, multiple myeloma-related bone disorder, leukemias and related disorders, myelodysplastic syndrome, acute myelogenous leukemia, chronic myelogenous leukemia, metastatic melanoma, Kaposi's sarcoma, multiple myeloma, sepsis, septic shock, Shigellosis, Alzheimer's disease, Parkinson's disease, cerebral ischemia, myocardial ischemia, myocardial infarction, congestive heart failure, Huntington's disease, atherosclerosis, spinal muscular atrophy, multiple sclerosis, AIDS-related encephalitis, HIV-related encephalitis, aging, alopecia, neurological damage due to stroke, ulcerative colitis, infectious hepatitis, juvenile diabetes, lichen planus, acute dermatomyositis, eczema, primary cirrhosis, uveitis, Behcet's disease, atopic skin disease, pure red cell aplasia, aplastic anemia, amyotrophic lateral sclerosis, nephrotic syndrome and systemic diseases or diseases with effects localized in the liver or other organs having an inflammatory or apoptotic component caused by excess dietary alcohol intake or viruses, such as HBV, HCV, HGV, yellow fever virus, dengue fever virus, and Japanese encephalitis virus.

Typically, the pharmaceutical compositions of this invention is administered from about 1 to 5 times per day or alternatively, as a continuous infusion. Such administration can be used as a chronic or acute therapy. The amount of active ingredient that may be combined with the carrier materials to produce a single dosage form varies depending upon the host treated and the particular mode of administration. A typical preparation contain from about 5% to about 95% active compound (w/w). Preferably, such preparations contain from about 20% to about 80% active compound.

When the compositions of this invention comprise a combination of a caspase 1/ICE inhibitor and one or more additional therapeutic or prophylactic agents, both the compound and the additional agent should be present at dosage levels of between about 10% to 80% of the dosage normally administered in a monotherapy regime.

Upon improvement of a patient's condition, a maintenance dose of a compound, composition or combination of this invention may be administered, if necessary. Subsequently, the dosage or frequency of administration, or both, may be reduced, as a function of the symptoms, to a level at which the improved condition is retained. When the symptoms have been alleviated to the desired level, treatment should cease. Patients may, however, require intermittent treatment on a long-term basis upon any recurrence or disease symptoms.

As the skilled artisan will appreciate, lower or higher doses than those recited above may be required. Specific dosage and treatment regimens for any particular patient depends upon a variety of factors, including the activity of the specific compound employed, the age, body weight, general health status, sex, diet, time of administration, rate of excretion, drug combination, the severity and course of the disease, and the patient's disposition to the disease and the judgment of the treating physician.

IL-1, IL-17 or apoptosis other forms of cell death such as pyroptotic cell death and necrotic cell death mediated diseases which may be treated or prevented by the compounds of this invention include, but are not limited to, inflammatory diseases, autoimmune diseases, proliferative disorders, infectious diseases, and degenerative diseases. The apoptosis-mediated diseases which may be treated or prevented by the compounds of this invention include degenerative diseases.

IL-1, IL-17 or apoptosis other forms of cell death such as pyroptotic cell death and necrotic cell death mediated inflammatory diseases which may be treated or prevented include, but are not limited to osteoarthritis, acute pancreatitis, chronic pancreatitis, asthma, and adult respiratory distress syndrome. Preferably the inflammatory disease is osteoarthritis or acute pancreatitis.

IL-1, IL-17 or apoptosis other forms of cell death such as pyroptotic cell death and necrotic cell death mediated autoimmune diseases which may be treated or prevented include, but are not limited to, glomerulonephritis, rheumatoid arthritis, systemic lupus erythematosus, scleroderma, chronic thyroiditis, Graves' disease, autoimmune gastritis, insulin-dependent diabetes mellitus (Type I), autoimmune hemolytic anemia, autoimmune neutropenia, thrombocytopenia, chronic active hepatitis, myasthenia gravis, multiple sclerosis, inflammatory bowel disease, Crohn's disease, psoriasis, atopic dermatitis and graft vs. host disease. Preferably the autoimmune disease is rheumatoid arthritis, inflammatory bowel disease, Crohn's disease, psoriasis, or atopic dermatitis.

IL-1, IL-17 or apoptosis other forms of cell death such as pyroptotic cell death and necrotic cell death mediated destructive bone disorders which may be treated or prevented include, but are not limited to, osteoporosis and multiple myeloma-related bone disorder.

IL-1, IL-17 or apoptosis other forms of cell death such as pyroptotic cell death and necrotic cell death mediated proliferative diseases which may be treated or prevented include, but are not limited to, leukemias and related disorders, such as myelodysplastic syndrome, acute myelogenous leukemia, chronic myelogenous leukemia, metastatic melanoma, Kaposi's sarcoma, and multiple myeloma.

IL-1, IL-17 or apoptosis other forms of cell death such as pyroptotic cell death and necrotic cell death mediated infectious diseases which may be treated or prevented include, but are not limited to, sepsis, septic shock, and Shigellosis.

IL-1, IL-17 or apoptosis other forms of cell death such as pyroptotic cell death and necrotic cell deaths mediated degenerative or necrotic diseases which may be treated or prevented by the compounds of this invention include, but are not limited to, Alzheimer's disease, Parkinson's disease, cerebral ischemia, and myocardial ischemia. Preferably, the degenerative disease is Alzheimer's disease.

IL-1, IL-17 or apoptosis other forms of cell death such as pyroptotic cell death and necrotic cell death mediated degenerative diseases which may be treated or prevented by the compounds of this invention include, but are not limited to, Alzheimer's disease, Parkinson's disease, cerebral ischemia, myocardial ischemia, spinal muscular atrophy, multiple sclerosis, AIDS-related encephalitis, HIV-related encephalitis, aging, alopecia, and neurological damage due to stroke.

Other diseases having an inflammatory or apoptotic component may be treated or prevented by the compounds of this invention. Such diseases may be systemic diseases or diseases with effects localized in the liver or other organs and may be caused by, for example, excess dietary alcohol intake or viruses, such as HBV, HCV, HGV, yellow fever virus, dengue fever virus, and Japanese encephalitis virus.

IL-6, IL-17-, IL-18-, IFN-γ- or TNF-α-mediated disease which may be treated or prevented by the compounds of this invention include, but are not limited to, inflammatory, infectious, autoimmune, proliferative, neurodegenerative and necrotic conditions.

IL-6, IL-17-, IL-18-, IFN-γ- or TNF-α-mediated inflammatory disease which may be treated or prevented include, but are not limited to osteoarthritis, acute pancreatitis, chronic pancreatitis, asthma, rheumatoid arthritis, inflammatory bowel disease, Crohn's disease, ulcerative colitis, cerebral ischemia, myocardial ischemia and adult respiratory distress syndrome. Preferably, the inflammatory disease is rheumatoid arthritis, ulcerative colitis, Crohn's disease, hepatitis or adult respiratory distress syndrome.

IL-6, IL-17-, IL-18-, IFN-γ- or TNF-α-mediated infectious disease which may be treated or prevented include, but are not limited to infectious hepatitis, sepsis, septic shock and Shigellosis.

IL-6, IL-17-, IL-18-, IFN-γ- or TNF-α-mediated autoimmune disease which may be treated or prevented include, but are not limited to glomerulonephritis, systemic lupus erythematosus, scleroderma, chronic thyroiditis, Graves' disease, autoimmune gastritis, insulin-dependent diabetes mellitus (Type I), juvenile diabetes, autoimmune hemolytic anemia, autoimmune neutropenia, thrombocytopenia, myasthenia gravis, multiple sclerosis, psoriasis, lichen planus, graft vs. host disease, acute dermatomyositis, eczema, primary cirrhosis, hepatitis, uveitis, Behcet's disease, atopic skin disease, pure red cell aplasia, aplastic anemia, amyotrophic lateral sclerosis and nephrotic syndrome. Preferably, the autoimmune disease is glomerulonephritis, insulin-dependent diabetes mellitus (Type I), juvenile diabetes, psoriasis, graft vs. host disease or hepatitis.

More preferred diseases or conditions which may be treated or prevented include rheumatoid arthritis, inflammatory bowel disease, including Crohn's disease and ulcerative colitis, inflammatory peritonitis, amyotrophic lateral sclerosis, septic shock, pancreatitis, traumatic brain injury, organ transplant rejection, osteoporosis, osteoarthritis, asthma, uveitis, psoriasis, Alzheimer's disease, myocardial infarction, congestive heart failure, Huntington's disease, atherosclerosis, atopic dermatitis, or leukemias and related disorders, such as myelodysplastic syndrome or multiple myeloma.

Accordingly, one embodiment of this invention provides a method for treating or preventing an IL-1 or apoptosis, pyroptosis or necrosis mediated disease in a subject comprising the step of administering to the subject any compound, pharmaceutical composition, or combination described herein and a pharmaceutically acceptable carrier.

Another embodiment of this invention provides a method for decreasing IL-18 production in a subject comprising the step of administering to the subject any compound, pharmaceutical composition, or combination described herein and a pharmaceutically acceptable carrier.

Yet another embodiment of this invention provides a method for decreasing IFN-γ production in a subject comprising the step of administering to the subject any compound, pharmaceutical composition, or combination described herein and a pharmaceutically acceptable carrier.

Although this invention focuses on the use of the compounds disclosed herein for preventing and treating IL-1, apoptosis, pyroptosis or necrosis-, IL-6, IL-17-, IL-18-, IFN-γ- or TNF-α-mediated disease, the compounds of this invention can also be used as inhibitory agents for other cysteine proteases.

Although the present invention and its advantages have been described in detail, it should be understood that various changes, substitutions and alterations can be made herein without departing from the spirit and scope of the invention as defined in the appended claims.

The present invention will be further illustrated in the following Examples which are given for illustration purposes only and are not intended to limit the invention in any way.

EXAMPLES

Example 1: Adaptive Immune Deficiency in a Lethal Case of COVID-19 in a Liver Transplant Patient-Potential Role for Pyroptosis The liver disease and transplant communities provide a window into populations that are especially important to study in light of coronavirus disease 2019 (COVID-19) as these patients typically have many co-morbidities, including diabetes, obesity and related cardiac issues, cancer, and most notably end-stage organ failure. What these co-morbidities have in common is underlying chronic inflammation involving activation of the inflammasome (Guo H, Callaway J B, Ting J P. Inflammasomes: mechanism of action, role in disease, and therapeutics. Nat Med 2015; 21:677-687). What these patients have in common is lethal experiences with COVID-19 (Onder G, Rezza G, Brusaferro S. Case-Fatality Rate and Characteristics of Patients Dying in Relation to COVID-19 in Italy. JAMA 2020). Putting these two factors together caused Applicants to speculate that the inflammasome, and more specifically pyroptosis, are what may drive tragic outcomes for patients with co-morbidities in the face of COVID-19. Applicants successfully explored this hypothesis in a recent liver transplant patient with several co-morbidities, who rapidly succumbed to the disease, and whose clinical course and immunological phenotype are described in this observation.

Figure 2A:
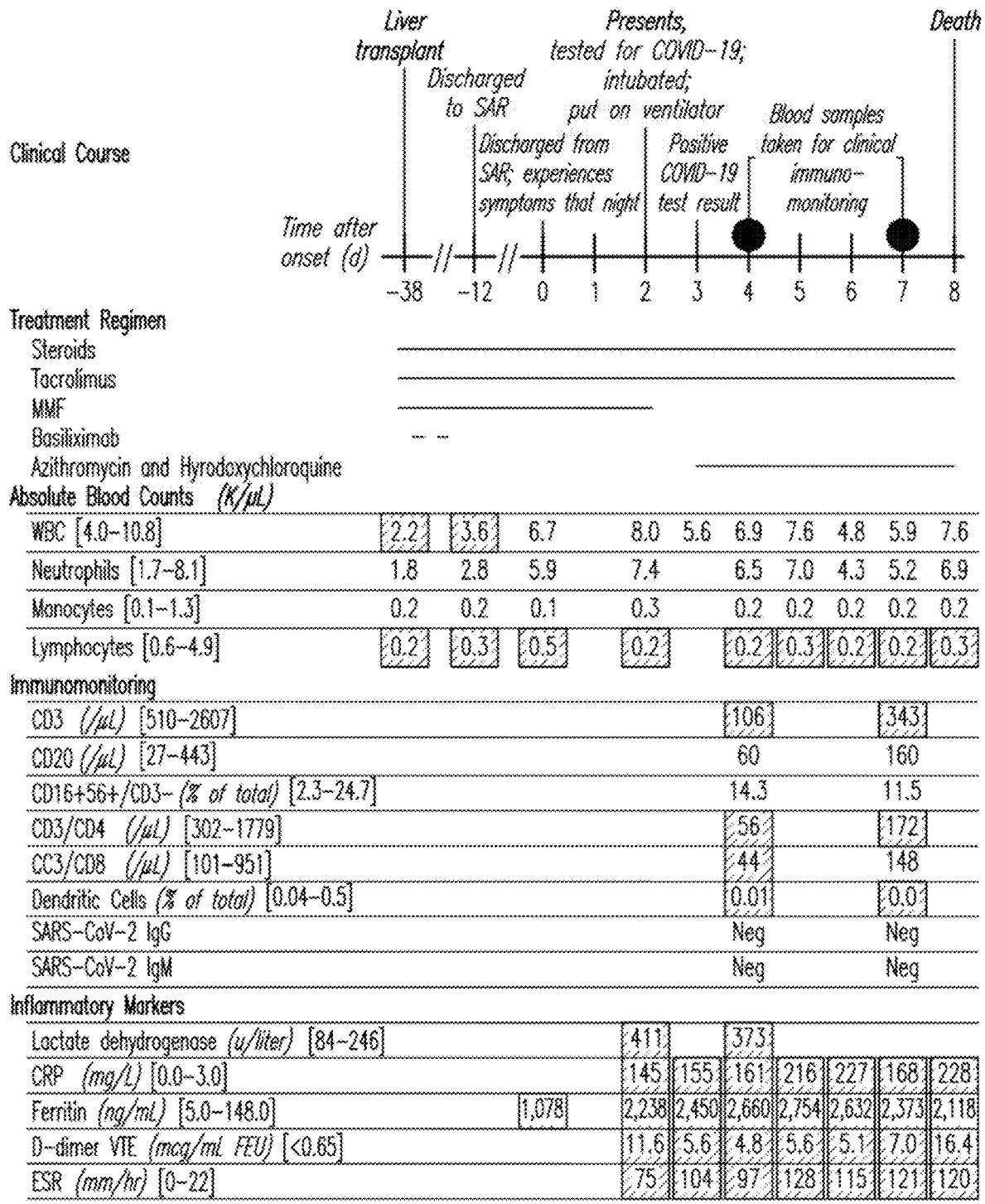
FIG. 2A: Clinical Course of an Immunosuppressed Patient with Rapid Deterioration Due to COVID-19. Chronology of patient clinical course, treatment regimen, absolute blood counts, clinical immunomonitoring data, and inflammatory markers. Red shading denotes that a given value is outside the reference range. Profound CD4 and CD8 T-cell lymphopenia is detected on day 4 after onset of symptoms (d4). On day 7 (d7), despite CD8 T-cell counts normalizing, CD4 Tcells remain in the lymphopenic range, despite an uptrend. NK and B-cell absolute counts and T-cell activation markers CD25 and HLA-DR are normal. Dendritic cells are absent in peripheral blood.
Figure 2B:
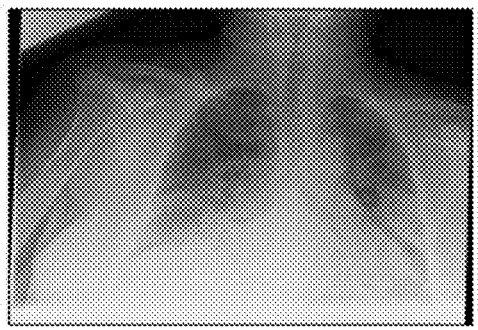
FIG. 2B. Images of patient chest x-rays and non-contrast chest CT scan. On day 2 after onset of symptoms (d2), the chest x-ray showed bilateral perihilar and basilar predominant airspace opacities, which were again demonstrated on day 4. On day 7 after onset of symptoms (d7), the CT scan showed diffuse bilateral pulmonary opacities characterized by severe groundglass opacities and moderate dependent consolidations.
Figure 2B:
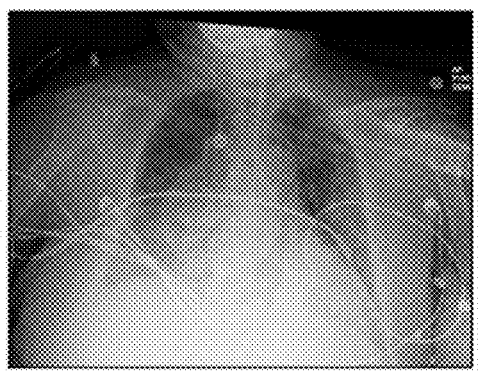
Figure 2B:
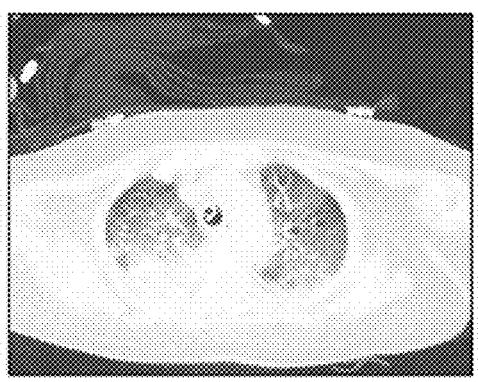

A 65-year old woman, with diabetes, hypertension, obesity, cirrhosis from primary sclerosing cholangitis, and a MELD score of 40 received a liver transplant in early 2020 (FIG. 2A) and was put on standard immunosuppression. 26 days post-transplant she was discharged into a sub-acute rehab facility, where Applicants suspect she contracted SARSCoV-2 as it later turned out to home three COVID-19 cases. Two days after returning home from the facility, she presented emergently with fever, dry cough, and shortness of breath for two days and was tested for COVID-19. A chest x-ray revealed multilobular interstitial infiltrates (FIG. 2B). She rapidly desaturated, got intubated, and underwent cardiopulmonary resuscitation for pulselessness, with return of spontaneous circulation. She was started on ARDSnet ventilation and hypothermia protocols in intensive care. Laboratory results showed marked lymphopenia and elevated inflammatory markers (FIG. 2A). She was treated with Hydroxychloroquine and Azithromycin after confirming COVID-19 the next day. Her neurological exam and head CT upon rewarming showed evidence of anoxic brain injury. ARDS and poor neurological status persisted (FIG. 2B), and she succumbed to COVID-19 six days after admission.

Although evidence for activation of antigen presenting cells (APCs) and involvement of Type-1-interferon response, as indicated by upregulation of CD11b and CD38 on monocytes and tetherin on B-cells, suggested innate immune activation there was a profound adaptive immune dysfunction (FIG. 2A and FIG. 3). Notably, Applicants found no B-cell memory cells and absence of SARS-CoV-2-specific IgG and IgM. Moreover, she exhibited profound T-cell lymphopenia, further underscored by absence of T-regulatory cells, low T-follicular helper cells, overexpression of CD38 in CD8 T-cells, and poor STAT-4 phosphorylation of CD4 T-cells upon IL-12 stimulation. Finally, high levels of lactate dehydrogenase (LDH) (FIG. 2A) and a global increase in caspase-1 staining (FIG. 3) in lymphocytes hinted at pyroptosis (Rayamajhi et al. Methods Mol Biol 2013; 1040:85-90 and Doitsh et al. Nature 2014; 505:509-514), which may explain her poor immune response.

Applicants' findings may shed new light on why and how SARS-CoV-2 infections cause such rapid lethality. T cell lymphopenia and lack of COVID specific IgM indicates that the adaptive immune system never properly kicked in. Caspase-1 overexpression in lymphocytes suggests pyroptosis as one of the possible mechanisms of T-cell depletion and functional abnormalities of other lymphocytes (Doitsh et al. Nature 2014; 505:509-514). This finding, even though limited to one patient presented here and potentially exacerbated by immunosuppressive medication, brings Applicants' attention to a COVID-19 induced acute immunodeficiency, resulting from the necrotic cell death of lymphocytes. Applicants propose that the inflammatory response is secondary to the danger signals from necrotic cell death of immune system cells, resulting in a heightened inflammation compared to the one induced by dying tissue cells (Matzinger P. Tolerance, danger, and the extended family. Annu Rev Immunol 1994; 12:991-1045). The end result is likely a self-damaging shut down of the immune system that further fuels the inflammation created by the viral infection. Applicants provide data backed connection between caspase-1 and COVID-19, a connection with significant therapeutic implications as rather than inhibition of the inflammatory response, preventing the pyroptotic lymphocyte death fueling the inflammation becomes more critical.

This patient was a 65-year-old woman with decompensated liver cirrhosis from primary sclerosing cholangitis complicated by jaundice, ascites, hepatic encephalopathy, and portal hypertension with esophageal varices, and a history of chronic portal vein thrombosis requiring anticoagulation with warfarin and recanalization with transjugular intrahepatic portosystemic shunt (TIPS). Her model for end-stage liver disease (MELDNa) score at time of transplant was 40. Past medical history included insulin dependent diabetes mellitus, obesity (body mass index (BMI) 32), hypertension, and gout. Past surgical history included open cholecystectomy, umbilical hernia repair, and hysterectomy.

She underwent orthotopic liver transplantation in early 2020 (see Supplementary Table 1 for her pre-transplant laboratory panel, noted as day −38 from the onset of COVID-19 symptoms). She received an organ from a 19-year-old male brain-dead deceased donor. Donor/recipient cytomegalovirus (CMV) and Epstein-Barr virus (EBV) serologies were +/+ and +/+, respectively. The liver transplant was performed in a standard fashion (vena cava replacement without veno-venous bypass) with standard portal vein and arterial anastomoses. Intraoperative findings included significant portal hypertension with venous collaterals, dense adhesions from prior open cholecystectomy, intraoperative right atrial thrombus which resolved with tissue plasminogen activator (tPA) lysis, and significant blood loss due to coagulopathy.

After successful liver transplantation the patient was transferred to the intensive care unit (ICU) with external biliary drainage and open abdomen. After resolution of the coagulopathy, she returned to the operating room (OR) 72 hours later in stable conditions for biliary reconstruction and closure of the abdomen.

Induction immunosuppression consisted of methylprednisolone (1 g intravenous therapy (i.v.) post-operative day (POD) 0) and basiliximab (20 mg i.v. POD 2 and 5, respectively). Maintenance immunosuppression regimen included tacrolimus (2 mg orally (p.o.) twice per day), mycophenolate-mofetil (1 g p.o. twice per day), and standard steroid taper. The patient received standard anti-infectious prophylaxis with sulfamethoxazole-trimethoprim, nystatin, and ganciclovir.

Her initial post-transplant course was characterized by slow normalization of serum bilirubin levels and acute renal failure requiring renal replacement therapy (both of which resolved prior to discharge; see also Supplementary Table 1 for her laboratory panel upon discharge, noted as day −12 from the onset of COVID-19 symptoms), and anemia requiring transfusion of two units of packed red blood cells (PRBCs). In addition, her post-transplant course was notable for mental status changes responding to Quetiapine without intracranial abnormal imaging findings, temporary dysphonia from vocal cord paralysis, dysphagia requiring enteral tube feeding via naso-jejunal tube and *Clostridium difficile*-negative diarrhea, which improved after resumption of regular diet. Incidentally, the patient was found to have a chronic left humeral neck fracture on routine post-operative chest x-ray, which was treated conservatively.

On POD 26, the patient was discharged to a subacute rehab (SAR) facility in stable condition with normal allograft function (see Supplementary Table 1 for her labs upon discharge, noted as day −12 from the onset of COVID-19 symptoms). She returned for routine follow ups over the coming weeks, which all showed normal labs, including (coincidently) on the very day that she later reported first feeling symptoms later that night (see Supplementary Table 1 for her labs that day, noted as day 0 from the onset of COVID-19 symptoms).

Two days after discharge from the rehabilitation facility, she presented to Applicants' emergency department with fever 37.6?, dry cough, and shortness of breath for two days. On presentation the peripheral oxygen saturation (S—O2) was 96% on room air; her blood pressure and heart rate where within normal limits. A nasopharyngeal swab specimen was obtained and sent for COVID-19 real-time PCR testing (see methods below for test relevant details). A chest x-ray revealed multilobular bilateral interstitial infiltrates (see FIG. 2B). While completing evaluation in the emergency department, the patient rapidly desaturated (S—$O_2$ 20-30%) and became unresponsive requiring bedside intubation. She was found to be pulseless and underwent immediate cardiopulmonary resuscitation, including chest compressions with return of spontaneous circulation. Upon transfer to intensive care ARDSnet ventilation and hypothermia protocols were initiated. Laboratory results showed marked lymphopenia and elevated inflammatory markers (see FIG. 2A). Empiric antibiotics (Cefepime (2 g i.v. q12 h) and Vancomycin (1 g i.v.) were administered for potential community acquired pneumonia. Hydroxychloroquine (400 mg twice per day followed by 200 mg twice per day) and Azithromycin (250 mg i.v. q24 h) were added the following day upon positive result of the nasopharyngeal swab test for COVID-19. The neurological exam and head CT findings upon rewarming showed evidence of diffuse anoxic brain injury. Poor neurological status and ARDS requiring ventilation (Fi02>=60%) persisted over subsequent days. Repeat CT imaging of the head and chest (see FIG. 2B) showed no improvement in terms of anoxic brain injury and ARDS, and she succumbed to COVID-19 six days after admission, eight days after first experiencing symptoms.

The patient was enrolled in a MedStar Georgetown Transplant Institute biorepository study (IRB #2017-0365). Written informed consent was obtained prior to inclusion into that study. Ethical utilization of transplant organs and tissue abided by principles in the Declaration of Helsinki. The donor organ was not obtained from an executed prisoner or otherwise institutionalized person.

Clinical specimens of the nasopharynx for SARS-CoV-2 testing were obtained, handled, and processed via real-time polymerase chain reaction assay as previously reported by Applicants' hospital group (Iqbal et al. N Engl J Med 2020 and Corman et al. Euro dSurveill 2020; 25). Briefly, viral nucleic acid was extracted by the MagNA Pure 96 IVD automated instrument (ROCHE Diagnostics) from nasopharyngeal swab specimen. Real-Time PCR was performed using the COBAS® Z480 Real-Time PCR System (ROCHE Diagnostics).

Patient samples for clinical immunophenotyping were obtained on day 4 and day 7 after onset of symptoms. Images shown in FIGS. 3A-E are from day 7 sample. A healthy sample was used as a matched control. Samples were processed in accordance with Amerimmune's clinical safety SOPs. Appropriate PPE were used when processing samples.

Peripheral blood from venipuncture was drawn into EDTA and heparin coated vacutainer tubes (BD Bioscience) for clinical immunophenotyping. Whole blood collected in EDTA tubes was immunostained per the clinical standard immunophenotyping protocol (Amerimmune LLC, Fairfax, Va.). The samples were stained with the antibody combinations as indicated in the supplemental Table 1 for 30 minutes at 4° C. Red blood cells were lysed using BD FACS lysis solution (BD Bioscience, Jan Jose, Calif.) as per manufacture directions.

Peripheral blood mononuclear cells (PBMC) were separated from 2 mL of whole blood diluted 1:1 with phosphate buffered saline pH 7.2 (PBS) (Thermo Fisher Scientific, Carlsbad, Calif.) using Lymphoprep (Stem cell Technologies, Cambridge, Mass.) and Accuspin tubes (Sigma-Aldrich, St. Louis, Mo.) as per manufactures directions. PBMCs' were washed in PBS and resuspended in 0.4 mL PBS. 100 μL of the PBMCs were immunostained with a mixture of antibodies as indicated in supplemental Table 2 at 4? for 1 hour. Cells were washed and resuspended in PBS prior to acquisition.

The antibodies utilized from Thermo Fisher Scientific were CD56 SB436 [TULY56], CD45 eF506 [HI130], CD3 FITC [SK7], CD16 PE [B73.1], CD8 PerCP-eF710 [SK1], CD14 PE-CY7 [61D3], CD4 APC [SK-3], CD20 APC-eF780 [2H7] CD25 EF450 [CD25-4E3], CD57 FITC [TBol], TCRγ-δ PE [B1.1], CD4 PerCP-eF710 [SK-3], CD3 PE-CY7 [SK7], TCR αβ APC [IP26], HLA-DR AF700 [LN3], CD8 APC-eF780 [SL1], IgD SB436 [IA6-2], IgA FC Secondary Antibody FITC, IgG FC Secondary Antibody PE, IgM PerCPeF710 [SA-DA4], CD19 PE-CY7 [SJ25C1], CD27 APC [0323], CD5 FITC [UCHT2], CD21 PE [HB5], CD27 PerCP-eF710 [O323], CD45RA FITC [HI100], CD45RO PerCPeF710 [UCHL1], CD294 APC [BM16], CD4 AF700 [RPA-T4], CD3 FITC [SK7], CD14 FITC [61D3], CD16 FITC [3G8], CD19 FITC [SJ25-C1], CD20 FITC [2H7], CD56 FITC [TULY56], CD34 FITC [4H11], CD11c PE [3.9], HLA-DR PerCP-EF710 [L243], CD303a APC [201A], CD4 SB600 [SK-3], CD45RA FITC [HI100], CD3 PE-CY7 [SK7], CD8 AF700 [SK1], CCR5 APC [NP-6G4], CD25 APC [BC96], CD317 PE [26F8], IL-6 PECY7 [MQ2-13A5], MIP1-β APC [FL34Z3L].

The antibodies utilized from BD Bioscience were HLADR BV480 [G46-6], CD38 PerCPCY5.5 [HIT2], CD28 APC [CD28.2], CD45 APC H7 [2D1], CD278 BV421 [DX29], CXCR5 PerCP-CY5.5 [RF8B2], CD127 BV480 [HIL-7R-M21], CD45RO PerCP-CY5.5 [UCHL1], CD20 APC-H7 [2H7], CD11b BV421 [ICRF44], CD16 FITC [NKP15], MIP1-α PE [11A3], HLA-DR PerPC-Cy5.5 [L243], Perforin Alexa488 [δG9], and Granzyme B PE [GB11]. TNF-α BV421 [Mab11] was from Biolegend (San Diego, Calif.).

Apoptosis and pyroptosis were measured by flow cytometry using fluorescent-labeled inhibitors of caspase probe assay, FLICA, as per manufactures protocol (Immunochemistry Technologies, Minneapolis, Minn.). FAM-FLICA probes specific for Caspase 1 and Caspase 3/7 were directly added to 100 μl PBMC, incubated for 1 hour at 37° C. Cells were washed 3 times with wash buffer to remove unbound FLICA probes. Cells were stained for CD45 PE-CY7 [HI30], CD3 AF700 [UCHT1], CD4 PE [RPA-T4], CD45RO PerCP-EF710 [UCHL1] and Viability Dye 780 (Thermo Fisher Scientific, Carlsbad, Calif.) to identify viable CD45+CD3+CD4+CD45RO-T cells. An additional singlet gate was incorporated in the gating scheme to identify singlets.

Whole blood was stimulated with IL-12 (100 ng/ml) for 0, 15, 30, 60 and 120 minutes. Cells were stained as per the BD Phosflow protocol. In brief, cells were stained with CD3 APC [SK7], CD4 PE-CY7 [SK3], CD45RO BV421 [UCHL1] and p-STAT4 [38/p-Stat4]. CD3+CD4+ T cells were identified from the lymphocyte and singlet gate described previously. The CD45RO/pSSTAT4 plots are gated on CD3+CD4+ T cells.

The samples were acquired on a 3 laser BD FACS Canto 10. CS&T beads (BD Bioscience, San Jose, Calif.) were acquired daily to ensure consistent performance of the Canto10. The BD FACS Canto 10 was cleaned with 10 minutes of 10% bleach and water following acquisition of samples. The CANTO10 utilized for this study has been validated for T, B, NK and Dendritic cell immunophenotyping clinical diagnostic testing. Denovo FCS Express v6 clinical edition (De Novo Software, Pasadena, Calif.) was used for flow cytometric analyses.

Monocytes were identified by a standard gating strategy utilizing CD14, CD16 and HLADR to identify classical, intermediate and nonclassical monocytes. CD38 and CD11b MFI and percent positive were examined form CD14++ CD16+ intermediate monocytes.

Figure 3A:
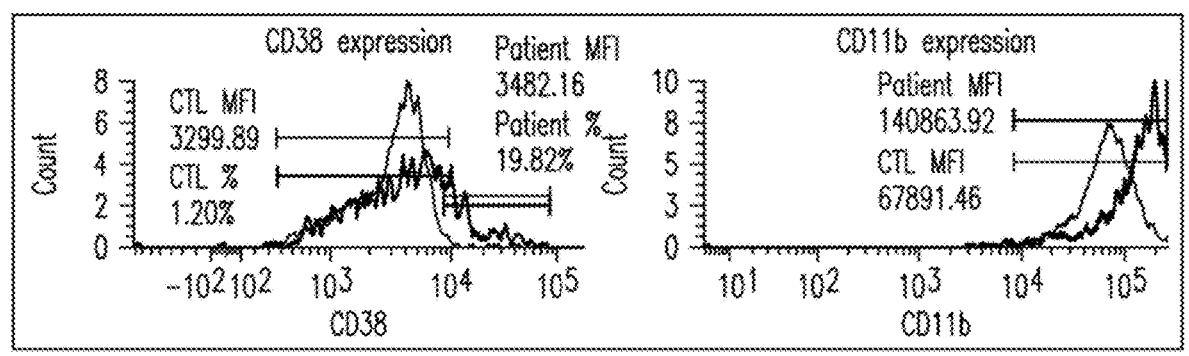
FIG. 3A: Immunological Phenotype of an Immunosuppressed Patient with Rapid Deterioration Due to COVID-19 based on clinical immune phenotyping of peripheral blood samples obtained day 7 after onset of COVID-19 symptoms (d7). Innate Immune Phenotype: CD16+ monocytes showed significant upregulation of CD11b and proinflammatory CD14+CD16+ monocytes showed upregulation of CD38. Approximately 15% of B-cells showed surface tetherin staining. Monocyte cytoplasmic IL6, MIP1α, MIP1β, and TNF-α levels were overall normal compared to controls (data not shown).
Figure 3A:
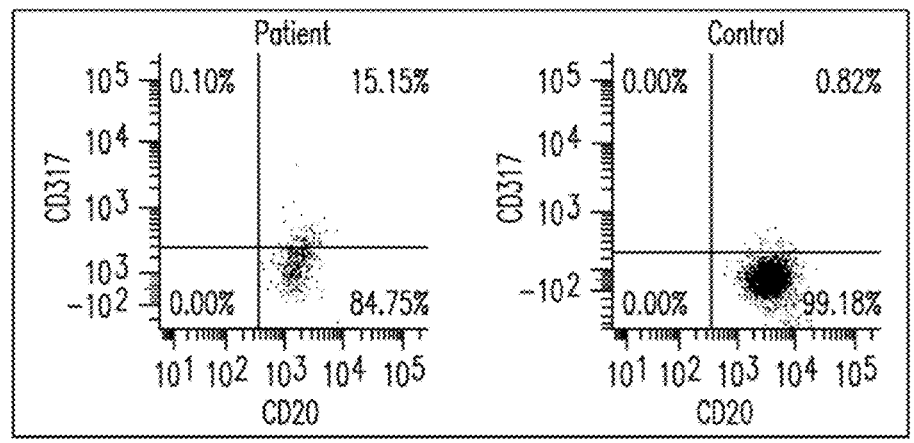
Figure 3B:
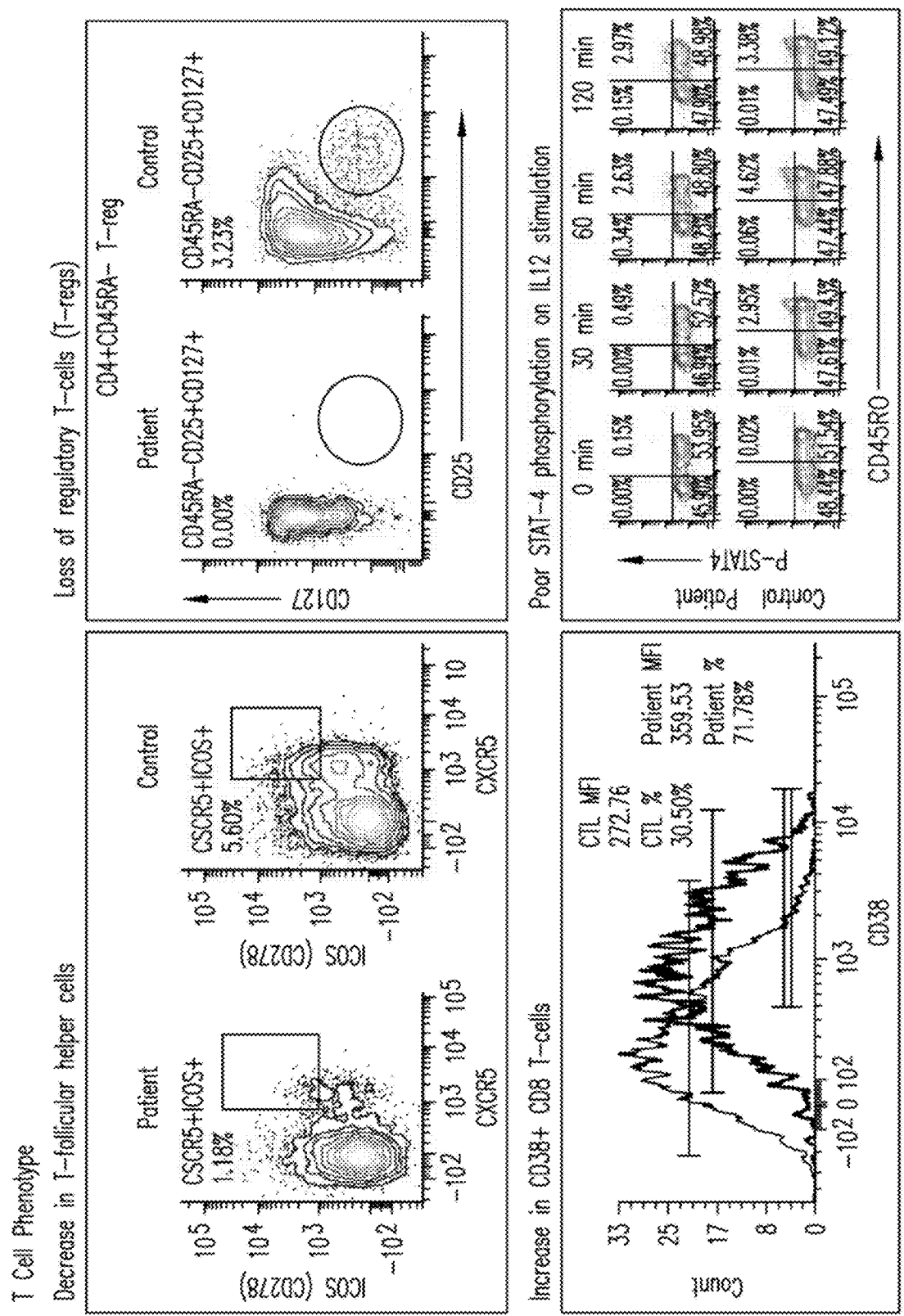
FIG. 3B. T Cell Phenotype: There was a decrease in CXCR5+ ICOS+T-follicular helper cells and complete absence of CD127-CD25+T-reg cells. The majority of CD4 T-cells were naïve and phosphorylated STAT-4 late and poorly on IL-12 stimulation. CD8 T-cells showed strong upregulation of CD38.
Figure 3C:
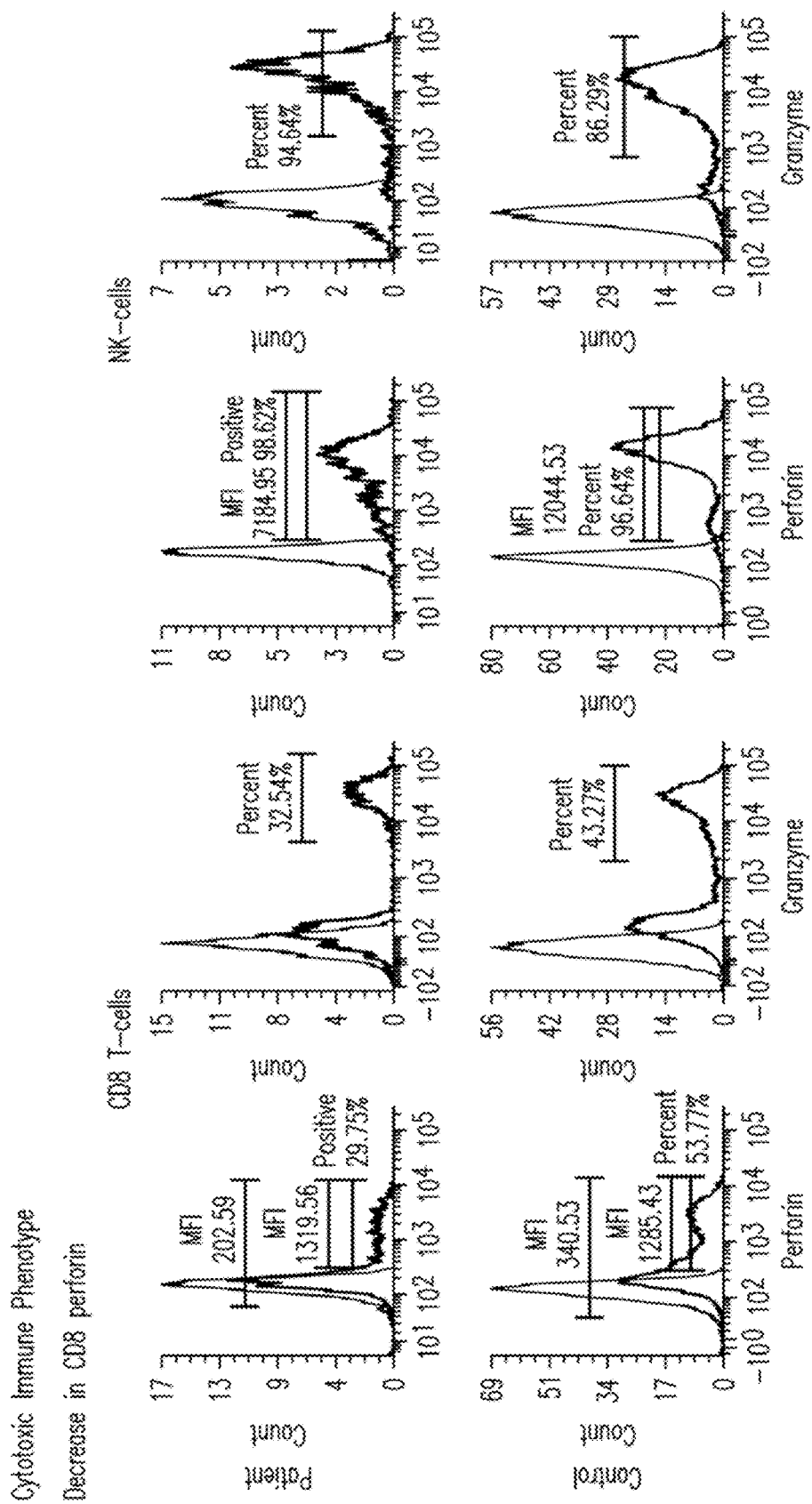
FIG. 3C. Cytotoxic Immune Phenotype: CD8 T-cells showed decrease in % of perforin positive cells. No changes were observed for NK-cell perforin/granzyme staining.
Figure 3D:
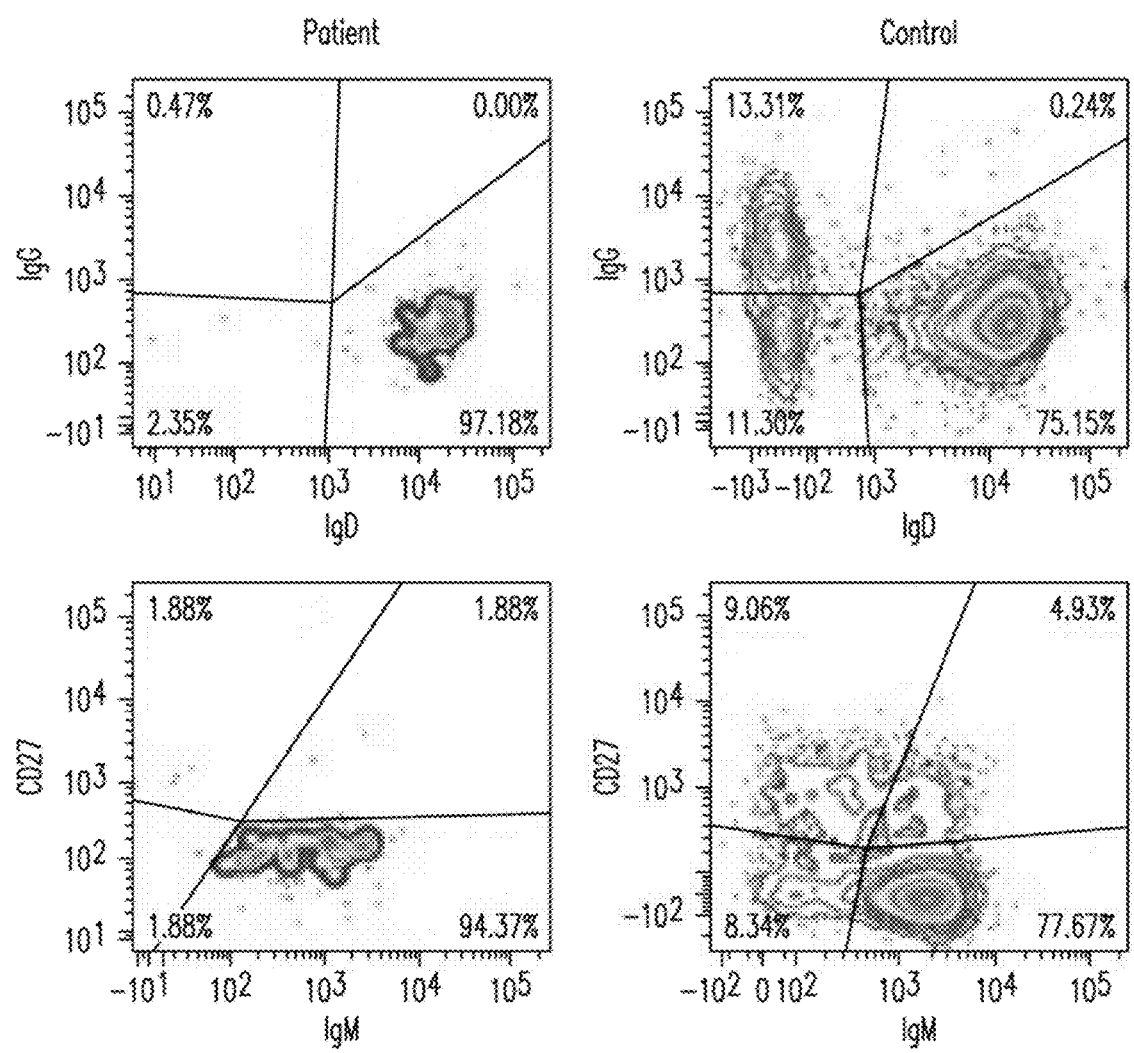
FIG. 3D. Humoral Immune Phenotype: B-cells showed profound loss of CD27+ memory, as well as surface IgG and IgA. SARS-CoV-2-specific IgG and IgM were absent (see also FIG. 2A).
Figure 3E:
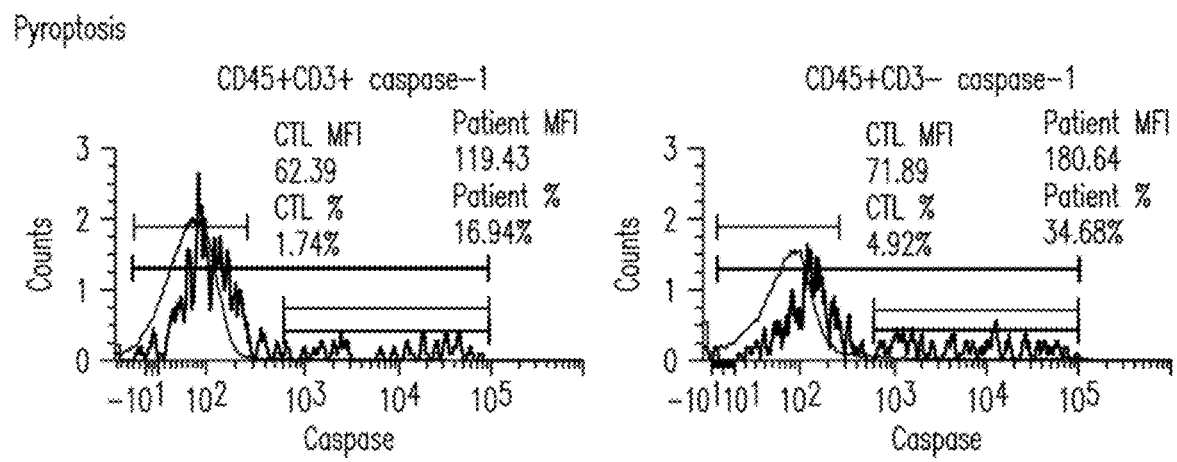
FIG. 3E Pyroptosis: There was increase in caspase-1 staining of CD45+CD3+ T-cells as well as CD45+CD3− cells. Caspase-3 staining was not different than controls (data not shown).

Lymphocytes were identified using a standard gating schematic incorporated gating of lymphocytes on a FSC/SSC plot and singlets on a FSC-A/FSC-H plot. From the lymphocyte plots, T cells were identified as CD45+ on a CD45/SSC plot. CD45+CD3+ cells were gated on a CD3/SSC plot. CD4+ and CD8+ T cells were identified by CD4/CD8 CD3+ gating. Subsequent T cell subpopulations as indicated in FIG. 3B were identified from CD45+CD3+ CD4+ or CD8+ cells.

Perforin and Granzyme B immune-phenotyping was done on CD8+ T cells and NK cells. Lymphocytes were identified as described previously on a FSC/SSC and FSCA/FSC-H plots. NK and T cells were identified by a CD56/TCR α/β plot. NK cells were identified as CD56+TCR α/β- and T cells were identified as TCRα/β+CD56− and CD8+ on a CD8/SSC plot. Identified specific populations were examined for perforin and granzyme staining, using an FMO control for both perforin and granzyme.

From the lymphocyte gating plots, B cells were identified as CD45+, then CD20+ from a CD20/SSC plot. All B cell subpopulations were identified from the CD45+CD20+ population.

For SARS-CoV-2 IgG and IgM antibody detection, Applicants used four lateral flow assay kits for COVID IgG and/or IgM (Dynamiker Technology, Tianjin, China; Wondfo, Guangdong, China; and Shenyang Union Biotechnologies, Liaoning, China), one chemiluminescent kit for COVID-19 IgG and IgM (Xincheng Biotechnologies, Sichuan, China), and ELISA for COVID-19 IgG/IgM (Antibody Biopharma, Gaithersburg, Md., USA). Those tests have a sensitivity in the range of 86% to 92% for known SARS-CoV-2 positive patients based on manufacturer information and previous clinical data. None of them were FDA approved assay at the time of the testing.

Supplementary Table S1 - Patient Clinical Laboratory Results

| | | Time after onset (d) | | | | | |
|---|---|---|---|---|---|---|---|
| | | −38 | −12 | 0 | 1 | 2 | 3 |
| | | | | Event | | | |
| Variable | Reference range | Liver transplant | Discharged to SAR | First symptoms | | Presents at ED | Positive COVID-19 test |
| Troponin (ng/ml) | 0-0.045 | | | | | 0.171 | 0.024 |
| Sodium (mmol/liter) | 137-145 | 135 | 142 | 136 | | 141 | 139 |
| Potassium (mmol/liter) | 3.5-5.1 | 3.8 | 5.1 | 5.3 | | 3.9 | 3.8 |
| Chloride (mmol/liter) | 98-107 | 109 | 115 | 104 | | 113 | 110 |
| Carbon dioxide (mmol/liter) | 21-32 | 19 | 18 | 25 | | 21 | 18 |
| Blood urea nitrogen (mg/dl) | 7-17 | 26 | 49 | 23 | | 14 | 25 |
| Creatinine (mg/dl) | 0.52-1.04 | 0.89 | 0.93 | 0.92 | | 0.71 | 1.30 |
| Glucose (mg/dl) | 65-140 | 482 | 129 | 185 | | 160 | 123 |
| Calcium (mg/dl) | 8.5-10.1 | 7.7 | 8.5 | 8.7 | | 7.6 | 7.7 |
| Total protein (gm/dl) | 6.3-8.2 | 5.2 | 5.5 | 6.7 | | 5.4 | 5.6 |
| Globulin (gm/dl) | 1.3-4.7 | 3.5 | 3.5 | 3.9 | | 3.1 | 3.2 |
| Aspartate aminotransferase (u/liter) | 3-34 | 126 | 15 | 14 | | 19 | 74 |
| Alanine aminotransferase (u/liter) | 15-41 | 128 | 17 | 23 | | 27 | 89 |
| Anion gap (mmol/liter) | 5-15 | 7 | 9 | 7 | | 7 | 11 |
| Albumin (gm/dl) | 3.5-5.0 | 1.7 | 2.0 | 2.8 | | 2.3 | 2.4 |
| Total bilirubin (mg/dl) | 0.2-1.3 | 26.7 | 1.1 | 0.8 | | 0.8 | 0.7 |
| Alkaline phosphatase (u/liter) | 45-117 | 530 | 126 | 87 | | 72 | 76 |
| Lactate dehydrogenase (u/liter) | 84-246 | | | | | 411 | |
| Lactic acid (mmol/liter) | 0.7-2.0 | 0.7 | | | | <0.7 | <0.7 |
| Hemoglobin (gm/dl) | 11-14.5 | 8.2 | 8.1 | 7.8 | | 7.0 | 8.0 |
| Hematocrit (%) | 34.5-44 | 24.9 | 26.4 | 25.6 | | 22.7 | 25.0 |
| Platelet count (k/μL) | 145-400 | 45 | 135 | 145 | | 139 | 94 |

Supplementary Table S1 - Patient Clinical Laboratory Results

| | | Time after onset (d) | | | | |
|---|---|---|---|---|---|---|
| | | 4 | 5 | 6 | 7 | 8 |
| | | | | Event | | |
| Variable | Reference range | | | | | Death |
| Troponin (ng/ml) | 0-0.045 | | | | | |
| Sodium (mmol/liter) | 137-145 | 138 | 138 | 141 | 142 | 147 |
| Potassium (mmol/liter) | 3.5-5.1 | 3.7 | 4.0 | 3.7 | 3.4 | 3.4 |
| Chloride (mmol/liter) | 98-107 | 108 | 109 | 112 | 113 | 118 |
| Carbon dioxide (mmol/liter) | 21-32 | 15 | 16 | 17 | 16 | 14 |
| Blood urea nitrogen (mg/dl) | 7-17 | 28 | 33 | 39 | 43 | 49 |
| Creatinine (mg/dl) | 0.52-1.04 | 1.43 | 1.68 | 1.66 | 1.58 | 1.59 |
| Glucose (mg/dl) | 65-140 | 146 | 178 | 169 | 184 | 249 |
| Calcium (mg/dl) | 8.5-10.1 | 7.9 | 8.0 | 8.2 | 8.2 | 8.7 |
| Total protein (gm/dl) | 6.3-8.2 | 6.0 | 5.8 | 6.0 | 6.4 | 6.4 |
| Globulin (gm/dl) | 1.3-4.7 | 3.8 | 3.9 | 4.2 | 4.4 | 4.5 |
| Aspartate aminotransferase (u/liter) | 3-34 | 71 | 52 | 55 | 57 | 51 |
| Alanine aminotransferase (u/liter) | 15-41 | 88 | 62 | 43 | 36 | 24 |
| Anion gap (mmol/liter) | 5-15 | 15 | 13 | 12 | 13 | 15 |
| Albumin (gm/dl) | 3.5-5.0 | 2.2 | 1.9 | 1.8 | 2.0 | 1.9 |
| Total bilirubin (mg/dl) | 0.2-1.3 | 0.7 | 0.6 | 0.5 | 0.5 | 0.6 |
| Alkaline phosphatase (u/liter) | 45-117 | 79 | 87 | 87 | 94 | 102 |
| Lactate dehydrogenase (u/liter) | 84-246 | 373 | | | | |
| Lactic acid (mmol/liter) | 0.7-2.0 | <0.7 | <0.7 | <0.7 | <0.7 | 1.0 |
| Hemoglobin (gm/dl) | 11-14.5 | 8.2 | 7.8 | 7.3 | 8.7 | 8.4 |
| Hematocrit (%) | 34.5-44 | 25.0 | 24.4 | 22.8 | 26.8 | 26.5 |
| Platelet count (k/μL) | 145-400 | 81 | 107 | 93 | 104 | 113 |

Items highlighted in red are outside the reference range.

Supplementary Table S2 - Patient Immunological Data Results

| | | Time after onset (d) | | | | | |
|---|---|---|---|---|---|---|---|
| | | −38 | −12 | 0 | 1 | 2 | 3 |
| | | | | | Event | | |
| Variable | Reference range | Liver transplant | Discharged to SAR | First symptoms | | Presents at ED | Positive COVID-19 test |
| Troponin (ng/ml) | 0-0.045 | | | | | 0.171 | 0.024 |
| Sodium (mmol/liter) | 137-145 | 135 | 142 | 136 | | 141 | 139 |
| Potassium (mmol/liter) | 3.5-5.1 | 3.8 | 5.1 | 5.3 | | 3.9 | 3.8 |
| Chloride (mmol/liter) | 98-107 | 109 | 115 | 104 | | 113 | 110 |
| Carbon dioxide (mmol/liter) | 21-32 | 19 | 18 | 25 | | 21 | 18 |
| Blood urea nitrogen (mg/dl) | 7-17 | 26 | 49 | 23 | | 14 | 25 |
| Creatinine (mg/dl) | 0.52-1.04 | 0.89 | 0.93 | 0.92 | | 0.71 | 1.30 |
| Glucose (mg/dl) | 65-140 | 482 | 129 | 185 | | 160 | 123 |
| Calcium (mg/dl) | 8.5-10.1 | 7.7 | 8.5 | 8.7 | | 7.6 | 7.7 |
| Total protein (gm/dl) | 6.3-8.2 | 5.2 | 5.5 | 6.7 | | 5.4 | 5.6 |
| Globulin (gm/dl) | 1.3-4.7 | 3.5 | 3.5 | 3.9 | | 3.1 | 3.2 |
| Aspartate aminotransferase (u/liter) | 3-34 | 126 | 15 | 14 | | 19 | 74 |
| Alanine aminotransferase (u/liter) | 15-41 | 128 | 17 | 23 | | 27 | 89 |
| Anion gap (mmol/liter) | 5-15 | 7 | 9 | 7 | | 7 | 11 |
| Albumin (gm/dl) | 3.5-5.0 | 1.7 | 2.0 | 2.8 | | 2.3 | 2.4 |
| Total bilirubin (mg/dl) | 0.2-1.3 | 26.7 | 1.1 | 0.8 | | 0.8 | 0.7 |
| Alkaline phosphatase (u/liter) | 45-117 | 530 | 126 | 87 | | 72 | 76 |
| Lactate dehydrogenase (u/liter) | 84-246 | | | | | 411 | |
| Lactic acid (mmol/liter) | 0.7-2.0 | 0.7 | | | | <0.7 | <0.7 |
| Hemoglobin (gm/dl) | 11-14.5 | 8.2 | 8.1 | 7.8 | | 7.0 | 8.0 |
| Hematocrit (%) | 34.5-44 | 24.9 | 26.4 | 25.6 | | 22.7 | 25.0 |
| Platelet count (k/μL) | 145-400 | 45 | 135 | 145 | | 139 | 94 |

-continued

| Supplementary Table S2 - Patient Immunological Data Results | | | | | | | |
|---|---|---|---|---|---|---|---|
| | | Time after onset (d) | | | | | |
| | | 4 | 5 | 6 Event | 7 | 8 | |
| Variable | Reference range | | | | | Death | |
| Troponin (ng/ml) | 0-0.045 | | | | | | |
| Sodium (mmol/liter) | 137-145 | 138 | 138 | 141 | 142 | 147 | |
| Potassium (mmol/liter) | 3.5-5.1 | 3.7 | 4.0 | 3.7 | 3.4 | 3.4 | |
| Chloride (mmol/liter) | 98-107 | 108 | 109 | 112 | 113 | 118 | |
| Carbon dioxide (mmol/liter) | 21-32 | 15 | 16 | 17 | 16 | 14 | |
| Blood urea nitrogen (mg/dl) | 7-17 | 28 | 33 | 39 | 43 | 49 | |
| Creatinine (mg/dl) | 0.52-1.04 | 1.43 | 1.68 | 1.66 | 1.58 | 1.59 | |
| Glucose (mg/dl) | 65-140 | 146 | 178 | 169 | 184 | 249 | |
| Calcium (mg/dl) | 8.5-10.1 | 7.9 | 8.0 | 8.2 | 8.2 | 8.7 | |
| Total protein (gm/dl) | 6.3-8.2 | 6.0 | 5.8 | 6.0 | 6.4 | 6.4 | |
| Globulin (gm/dl) | 1.3-4.7 | 3.8 | 3.9 | 4.2 | 4.4 | 4.5 | |
| Aspartate aminotransferase (u/liter) | 3-34 | 71 | 52 | 55 | 57 | 51 | |
| Alanine aminotransferase (u/liter) | 15-41 | 88 | 62 | 43 | 36 | 24 | |
| Anion gap (mmol/liter) | 5-15 | 15 | 13 | 12 | 13 | 15 | |
| Albumin (gm/dl) | 3.5-5.0 | 2.2 | 1.9 | 1.8 | 2.0 | 1.9 | |
| Total bilirubin (mg/dl) | 0.2-1.3 | 0.7 | 0.6 | 0.5 | 0.5 | 0.6 | |
| Alkaline phosphatase (u/liter) | 45-117 | 79 | 87 | 87 | 94 | 102 | |
| Lactate dehydrogenase (u/liter) | 84-246 | 373 | | | | | |
| Lactic acid (mmol/liter) | 0.7-2.0 | <0.7 | <0.7 | <0.7 | <0.7 | 1.0 | |
| Hemoglobin (gm/dl) | 11-14.5 | 8.2 | 7.8 | 7.3 | 8.7 | 8.4 | |
| Hematocrit (%) | 34.5-44 | 25.0 | 24.4 | 22.8 | 26.8 | 26.5 | |
| Platelet count (k/μL) | 145-400 | 81 | 107 | 93 | 104 | 113 | |

Items highlighted in red are outside the reference range.

Example 2: Potential Role of the Inflammasome in Transplant Patients with COVID-19

Applicants respond to the Correspondence "COVID-19 and Kidney Transplantation" which shared observations from kidney transplant patients at New York's Montefiore Medical Center and highlighted three themes: comorbidities, inflammation, and low T-cell/lymphocyte counts.

Based on observations from patients at the MedStar Georgetown Transplant Institute Applicants can both confirm and expand these observations based on 11 patients recently hospitalized due to COVID-19, 6 of whom were kidney and liver transplant patients (see below table).

Table for 11 Patients Sorted By Disease Severity—Page 1 of 2

| | | Patient | | | | | |
|---|---|---|---|---|---|---|---|
| | | 1 | 2 | 3 | 4 | 5 | 6 |
| | | Transplant Info | | | | | |
| Organ type | | Liver & Kidney | NA | Kidney | NA | Kidney | NA |
| Immunosuppression at presentation | | FK, MMF | NA | FK, MMF | NA | FK, MMF | NA |
| | | Potential COVID-19 Risk Categories | | | | | |
| Age > 50 | | No | Yes | No | Yes | Yes | Yes |
| Gender | | F | M | M | M | M | F |
| Race/ethnicity | | AA | Other | AA | AA | AA | Caucasian |
| BMI | | 32 | 31 | 37 | 21 | 30 | 29 |
| Comorbidities | | 3 | 4 | 2 | 3 | 4 | 5 |
| Diabetes | | | | | ✓ | ✓ | |
| Obesity | | ✓ | ✓ | ✓ | | ✓ | |
| Hypertension | | | ✓ | ✓ | | ✓ | |
| Heart disease | | ✓ | | | | | ✓ |
| Other | | PE | Liver cirrhosis, ETOH | | Nephrolithiasis, Hyperlipidemia | DVT | Liver disease, COPD, arthritis, hyperlipidemia |
| | | COVID-19 Course and Outcome | | | | | |
| Key symptoms at time of presentation | Fever | ✓ | ✓ | ✓ | | ✓ | |
| | Cough | | ✓ | | ✓ | ✓ | |
| | Dyspnea | | ✓ | ✓ | ✓ | | ✓ |
| | Myalgia/lethargy | | ✓ | ✓ | ✓ | ✓ | |
| | Diarrhea | | | ✓ | ✓ | ✓ | |
| Radiographic viral PNA detection | | ✓ | | ✓ | | ✓ | ✓ |
| Treatment | Hydroxychloroquine | | ✓ | ✓ | ✓ | ✓ | ✓ |
| | Azithromycin | | ✓ | | ✓ | | |

-continued

| Outcome | Hospitalization | ✓ | ✓ | ✓ | ✓ | ✓ | ✓ |
|---|---|---|---|---|---|---|---|
| | Supplemental O₂ | | | ✓ | ✓ | ✓ | ✓ |
| | Intubation/ICU | | | | | | ✓ |
| | No discharge by d 14 | | | | | | |
| | Death | | | | | | |

Inflammatory Markers (initial recorded value | highest recorded value)

| | | | | | | |
|---|---|---|---|---|---|---|
| LDH (u/liter) [84-246] | 246 \| 286 | 337 \| 368 | 203 \| 246 | 518 \| 559 | 240 \| 331 | 957 \| 957 |
| CRP (mg/L) [0.0-3.0] | 43.0 \| 43.0 | 11.5 \| 31.9 | 32.7 \| 70.6 | 240 \| 240 | 46.7 \| 138.0 | 53.3 \| 53.3 |
| Ferritin (ng/mL) [5.0-148.0] | 1432 \| 1432 | 57 \| 113 | 1609 \| 1815 | 522 \| 1295 | 574 \| 620 | 211 \| 238 |
| D-dimer VTE (mcg/mL FEU) [<0.65] | 4.35 \| 4.35 | 1.44 \| 1.44 | 0.49 \| 0.49 | >20 \| >20 | 1.20 \| 1.38 | >20 \| >20 |
| ESR (mm/hr) [0-22] | 78 \| 78 | Not available | 6 \| 12 | Not available | 35 \| 74 | Not available |
| Procalcitonin (ng/ml) [0.00-0.49] | 0.44 \| 0.44 | <0.1 \| <0.1 | <0.1 \| <0.1 | 5.23 \| 5.23 | Not available | 0.34 \| 0.34 |
| IL-6 (pg/ml) [<5.0] | Not available | 7 \| 7 | <5 \| <5 | Not available | Inconclusive | Not available |

Immunomonitoring (initial recoded value | lowest recored value)

| | | | | | | |
|---|---|---|---|---|---|---|
| WBC (K/μL) [4.0-10.8] | 2.3 \| 2.3 | 6.9 \| 5.2 | 4.4 \| 3.2 | 17.7 \| 7.9 | 3.4 \| 2.4 | 17.4 \| 5.9 |
| Lymphocytes (K/μL) [0.6-4.9] | 0.4 \| 0.4 | 1.1 \| 1.1 | 0.6 \| 0.6 | 1.6 \| 0.8 | 0.8 \| 0.8 | 0.9 \| 0.9 |
| CD3 (/μL) [510-2607] | 636 | 1012 | 205 | 470 | 578 | 1373 |
| CD3/CD4 (/μL) [302-1779] | 415 | 562 | 129 | 329 | 386 | 982 |
| CD3/CD8 (/μL) [101-951] | 168 | 401 | 63 | 126 | 169 | 336 |

Caspase-1 Activity (as determined by FAM-FLICA-caspase assay)

| | | | | | | |
|---|---|---|---|---|---|---|
| CD45 + CD3 + % [2.11-4.90] | 22.38 | 26.41 | 16.85 | 18.88 | 14.30 | 21.16 |
| CD45 + CD3 + CD4 + % [1.87-3.67] | 17.61 | 24.93 | 16.77 | 10.66 | 12.30 | 21.22 |
| CD45 + CD3 − % [3.77-16.6] | 22.91 | 14.28 | 28.41 | 28.98 | 36.24 | 0.89 |
| CD45 + CD3 + MFI [58.8-129.0] | 124 | 112 | 110 | 119 | 98 | 154 |
| CD45 + CD3 + CD4 + MFI [51.2-114.8] | 110 | 111 | 107 | 108 | 94 | 159 |
| CD45 + CD3 − MFI [61.2-170.4] | 156 | 112 | 135 | 164 | 137 | 22 |

| | Patient | | | | |
|---|---|---|---|---|---|
| | 7 | 8 | 9 | 10 | 11 |

Transplant Info

| | | | | | |
|---|---|---|---|---|---|
| Organ type | Kidney | NA | NA | Liver | Liver |
| Immunosuppression at presentation | FK, Prednisone | NA | MMF | FK, MMF, Prednisone | FK, MMF, Steroids |

Potential COVID-19 Risk Categories

| | | | | | |
|---|---|---|---|---|---|
| Age > 50 | Yes | Yes | Yes | No | Yes |
| Gender | M | F | F | M | F |
| Race/ethnicity | AA | Caucasian | AA | Caucasian | Other |
| BMI | 22 | 18 | 44 | 24 | 32 |
| Comorbidities | 5 | 3 | >6 | 4 | 4 |
| Diabetes | | | ✓ | ✓ | ✓ |
| Obesity | | | ✓ | | ✓ |
| Hypertension | ✓ | | ✓ | | ✓ |
| Heart disease | | ✓ | | | |
| Other | Gout, TB, BK nephritis | Liver cirrhosis, kidney failure, hypercalcemia | COPD, AIH, DVT, stroke, hyperlipidemia | AKI, HCV, graft rejection | Gout |

COVID-19 Course and Outcome

| | | | | | | |
|---|---|---|---|---|---|---|
| Key symptoms at time of presentation | Fever | ✓ | | ✓ | ✓ | ✓ |
| | Cough | ✓ | | ✓ | ✓ | ✓ |
| | Dyspnea | | | ✓ | | ✓ |
| | Myalgia/lethargy | ✓ | ✓ | ✓ | | |
| | Diarrhea | | | | ✓ | |
| Radiographic viral PNA detection | | ✓ | ✓ | ✓ | ✓ | ✓ |
| Treatment | Hydroxychloroquine | ✓ | ✓ | ✓ | ✓ | ✓ |
| | Azithromycin | | ✓ | ✓ | ✓ | ✓ |
| Outcome | Hospitalization | ✓ | ✓ | ✓ | ✓ | ✓ |
| | Supplemental O₂ | ✓ | ✓ | ✓ | ✓ | ✓ |
| | Intubation/ICU | | | ✓ | ✓ | ✓ |
| | No discharge by d 14 | ✓ | ✓ | ✓ | ✓ | ✓ |
| | Death | | | | | ✓□ |

Inflammatory Markers (initial recorded value | highest recorded value)

| | | | | | |
|---|---|---|---|---|---|
| LDH (u/liter) [84-246] | 257 \| 443 | 162 \| 190 | 388 \| 488 | 352 \| 388 | 411 \| 411 |
| CRP (mg/L) [0.0-3.0] | 63.3 \| 107.0 | 3.4 \| 5.4 | 96.2 \| 296.0 | 31.4 \| 101.0 | 145.0 \| 228.0 |
| Ferritin (ng/mL) [5.0-148.0] | 3254 \| 11230 | 1527 \| 1527 | 259 \| 439 | 2941 \| 4585 | 2238 \| 2754 |
| D-dimer VTE (mcg/mL FEU) [<0.65] | 14.35 \| 14.35 | 2.43 \| 2.43 | 1.92 \| 3.56 | 5.71 \| 5.71 | 11.55 \| 16.37 |
| ESR (mm/hr) [0-22] | 104 \| 104 | 67 \| 67 | 110 \| >150 | 55 \| 58 | 75 \| 128 |
| Procalcitonin (ng/ml) [0.00-0.49] | 46.2 \| 46.2 | 0.12 \| 0.12 | <0.1 \| 4.57 | 0.82 \| 3.74 | >150 \| >150 |
| IL-6 (pg/ml) [<5.0] | 10 \| 10 | 22 \| 22 | 70 \| 70 | <5 \| <5 | <5 \| <5 |

-continued

| Immunomonitoring (initial recoded value | lowest recored value) | | | | | |
|---|---|---|---|---|---|
| WBC (K/µL) [4.0-10.8] | 7.4 | 3.7 | 2.7 | 2.7 | 3.7 | 3.7 | 4.2 | 4.2 | 8.0 | 4.8 |
| Lymphocytes (K/µL) [0.6-4.9] | 1.2 | 0.9 | 0.9 | 0.6 | 0.9 | 0.4 | 0.2 | 0.2 | 0.2 | 0.2 |
| CD3 (/µL) [510-2607] | 735 | 592 | 1071 | 210 | 106 |
| CD3/CD4 (/µL) [302-1779] | 611 | 404 | 668 | 42 | 56 |
| CD3/CD8 (/µL) [101-951] | 108 | 176 | 380 | 160 | 44 |
| Caspase-1 Activity (as determined by FAM-FLICA-caspase assay) | | | | | |
| CD45 + CD3 + % [2.11-4.90] | 13.79 | 20.21 | 19.68 | 28.44 | 18.36 |
| CD45 + CD3 + CD4 + % [1.87-3.67] | 10.95 | 15.63 | 21.54 | 30.83 | 16.77 |
| CD45 + CD3 − % [3.77-16.6] | 12.32 | 2.86 | 3.68 | 6.23 | 28.99 |
| CD45 + CD3 + MFI [58.8-129.0] | 110 | 128 | 156 | 189 | 117 |
| CD45 + CD3 + CD4 + MFI [51.2-114.8] | 105 | 115 | 164 | 205 | 100 |
| CD45 + CD3 − MFI [61.2-170.4] | 130 | 47 | 51 | 41 | 149 |

Items shaded in red denote test values or patient characteristics that either fall outside or at the boundary of the standard reference range or are in a range that was highlighted as worrisome a recent NEJM paper ("Covid-19 and Kidney Transplantation" DOI: 10.1056/NEJMc2011117).

First, Applicants' patients also exhibited low T-cell counts and lymphopenia. In addition, Applicants see comorbidities with an inflammatory profile as especially high-risk for a morbid COVID-19 course (Guo et al. Nat Med 2015; 21:677-687). Given this finding and studies emphasizing the role of the inflammasome in coronaviruses (Shi et al. Cell Death Discov. 5, 101 (2019)), Applicants analyzed caspase-1 activity in their patients. Critically, Applicants found a strong upregulation of caspase-1 activity in both T-cells and lymphocytes as well as high LDH levels across their patients, suggesting pyroptosis as a cause of lymphopenia and a driver of heightened inflammation in COVID-19 similar to SARS-CoV-1 (Yue et al. Cell Death Dis 9, 904 (2018)). This insight has therapeutic implications beyond transplantation as it implies upstream prevention of pyroptosis may be beneficial.

Example 3: A Multicenter, Randomized Study to Evaluate the Safety and Efficacy of VX-765 in Improving Outcome in Patients with COVID-19 Pneumonia Methodology This study is conducted as a randomized safety, tolerability and efficacy study. Study duration is approximately 4 weeks. VX-765 is administered daily up to 15 days. The study is conducted on an in-patient basis with assessments performed at screening and daily thereafter up to 15 days and at 28 days (study termination).

| | |
|---|---|
| Study Duration | Each subject participates in the study for 4 weeks. |
| Study Centers | This is a multi-center trial with approximately 10 sites. |

Objectives The purpose of this study is to evaluate the safety, tolerability and efficacy of VX-765 in subjects with Covid-19 infection.

Primary Safety and Tolerability Objective:

To determine the safety and tolerability of daily VX-765 for up to 15 days in subjects with Covid-19 infection as determined by Adverse Events and Serious Adverse Events.

Primary Efficacy Objectives:

To determine the efficacy of VX-765 in improving outcome from Covid-19 infection as determined by a 7-point ordinal disease severity scale disease severity at 15 days.

Secondary Efficacy Objectives:

To determine the effect of VX-765 on outcome from Covid-19 infection as determined by improvement in the 7-point ordinal disease severity at 28 days. Duration of mechanical ventilation, duration of hospitalization, oxygenation status, ventilator use time from treatment initiation to death and virologic measures is assessed out to 28 days. Other assessments include improvement in markers of pyroptosis such as lymphopenia, T cell counts, LDH levels, Caspase 1 activity levels and other secondary immune markers as read out parameters and/or secondary end points.

| | |
|---|---|
| Number of Subjects | Approximately 80 subjects are entered into the study |
| Study Description | Multicenter study of daily VX-765 for up to 15 days |
| Study Population | Hospitalized patients with Covid-19 infection |
| Study Drug Administration | Oral |
| Inclusion/Exclusion Criteria | The study population is defined as subjects who meet the following criteria: |

Inclusion Criteria:

Subject (or legally authorized representative) provides written informed consent prior to initiation of any study procedures Understands and agrees to comply with planned study procedures Agrees to the collection of nasopharyngeal swabs and venous blood per protocol Male or non-pregnant female adult ≥18 years of age at time of enrollment Laboratory confirmed SARS-CoV-2 infection as determined by PCR, or other commercial or public health assay in any specimen <72 hours prior to randomization Hospitalized patients with illness of any duration, and at least one of the following:

Clinical assessment (presence of crackles/rales) AND SpO2≤94% on room air OR

Acute respiratory failure requiring mechanical ventilation and/or supplemental oxygen OR Radiographic infiltrates by imaging (CT, CXR)

Women of childbearing age must agree to use contraception for the duration of the study Exclusion Criteria Pregnant or breast feeding Uncontrolled, clinically significant heart diseases such as arrhythmias, angina or uncompensated congestive heart failure Non-hospitalized patients Study Product, Dose, Route, Regimen VX-765 is administered in oral form three times a day for up to 15 days.

The first group of subjects is dosed with 300 mg VX-765.

Study Endpoints Safety and Tolerability Endpoints:

Adverse Events and Serious Adverse Events out to 28 days, as evaluated with subject report, clinical assessment and vital signs, chemical chemistry and electrocardiograms (EKG).

Primary Efficacy Endpoint:

The primary efficacy endpoint is the severity rating on the following 7-point ordinal disease severity scale at 15 days.

Not hospitalized, no limitations on activities
Not hospitalized, limitation on activities
Hospitalized, not requiring supplemental oxygen
Hospitalized, requiring supplemental oxygen
Hospitalized, on non-invasive ventilation or high flow oxygen devices
Hospitalized, on invasive mechanical ventilation or ECMO
Death Secondary Efficacy Endpoints:

The severity rating on the 7-point ordinal disease severity scale at days 3, 6, 9, 12, and 28

Time to discharge or to a National Early Warning Score (NEWS) of <2 maintained for 24 hours, whichever occurs first (at 3, 6, 9, 12, 15, and 28 days)

Change from baseline in NEWS at days 3, 6, 9, 12, 15, and 28

Number of oxygen free days over 28 days
Incidence and duration of new oxygen use over 28 days
New mechanical ventilation over 28 days
Ventilator free days over 28 days
Duration of hospitalization
SARS-CoV-2 in nasopharyngeal sample at days 3, 6, 9, 12, 15, and 28
Quantitative SARS-CoV-2 virus in blood at days 3, 6, 9, and 12

Statistical Considerations Study Populations:

Safety Population: All enrolled subjects who have received at least 1 dose of study drug Efficacy Evaluable Population: All subjects in the Safety Population who complete the study with no major protocol violations Analysis Methods:

Descriptive summary statistics is presented for the safety and tolerability endpoints overall. Continuous variables are summarized using the number of observations, mean, standard deviation, median, minimum, and maximum. Categorical variables are summarized using frequency counts and percentages. Summary statistics are provided for Stage 1. Inferential statistics are performed in Stage 2.

Stage 2 Primary Efficacy Endpoint Analysis:

The primary efficacy endpoint analysis is a treatment group comparison of the patients' day 15 7-point ordinal disease severity scale using a Cochran-Mantel-Haenszel (CMH) row mean score difference test controlling for the baseline score. The primary efficacy analysis compares the pooled Stage 2 placebo groups to the pooled Stage 2 VX-765 groups at the two-sided 0.05 Type I error rate.

Sample Size Justification:

For Stage 1, the sample size of 4 subjects per group (2 on VX-765, 2 on placebo) is designed to provide an initial assessment of safety and tolerability for the initial doses of VX-765. The Stage 2 sample size of 28 patients in a VX-765 treatment group (i.e., the 2 VX-765 treatment groups combined) provides a 95% probability that an AE with an underlying rate of 10% occurs in these patients. Additionally, in Stage 2, a sample size of 28 patients per group (i.e., pooling the Stage 2 placebo groups and the VX-765 groups) provides approximately 80% power to detect a treatment difference at the 2-sided 0.05 Type I error rate based on a using a CMH row mean score difference test controlling for the baseline score.

This assumes the following day 15 distribution for the seven-category disease severity score.

Distribution of 7-point Ordinal Disease Severity Scale at 15 Days for Power Calculations

| | 7-Point Ordinal Disease Severity Scale | | | | | | |
|---|---|---|---|---|---|---|---|
| | 1 | 2 | 3 | 4 | 5 | 6 | 7 |
| VX-765 | 30% | 30% | 20% | 13% | 1% | 1% | 5% |
| Placebo | 10% | 20% | 20% | 20% | 5% | 5% | 20% |

Safety and Tolerability Objectives

To determine the safety and tolerability of VX-765 for up to 15 days in subjects with Covid-19 infection as determined by Adverse Events and Serious Adverse Events Safety and Tolerability Endpoints Adverse Events and Serious Adverse Events out to 28 days, as evaluated with subject report, clinical assessment, vital signs, chemical chemistry and electrocardiograms (EKG).

Primary Efficacy Objective:

To determine the efficacy of VX-765 in improving outcome from Covid-19 infection as determined by the 7-point ordinal disease severity scale at 15 days.

Primary Efficacy Endpoint:

The primary efficacy endpoint is the severity rating on the following 7-point ordinal disease severity scale at 15 days.

Not hospitalized, no limitations on activities
Not hospitalized, limitation on activities
Hospitalized, not requiring supplemental oxygen
Hospitalized, requiring supplemental oxygen
Hospitalized, on non-invasive ventilation or high flow oxygen devices
Hospitalized, on invasive mechanical ventilation or ECMO
Death Secondary Efficacy Objectives:

To determine the effect of VX-765 on outcome from Covid-19 infection as determined by improvement in the 7-point ordinal disease severity scale at 28 days. Duration of mechanical ventilation, duration of hospitalization, oxygenation status, ventilator use, time from treatment initiation to death and virologic measures is assessed out to 28 days.

Secondary Efficacy Endpoints:

The severity rating on the 7-point ordinal disease severity scale at days 3, 6, 9, 12 and 28

Time to discharge or to a (NEWS) of <2 maintained for 24 hours, whichever occurs first (at 3, 6, 9, 12, 15 and 28 days)

Change from baseline in NEWS at days 3, 6, 9, 12, 15, and 28

The National Early Warning Score, (NEWS) has demonstrated the ability to discriminate patients at risk of poor outcomes. This score is based on the following 7 clinical parameters Respiration rate
Oxygen saturation
Any supplemental oxygen
Temperature
Systolic blood pressure
Heart rate
Level of consciousness Number of oxygen free days over 28 days
Incidence and duration of new oxygen use over 28 days
New mechanical ventilation over 28 days
Ventilator free days over 28 days
Duration of hospitalization
SARS-CoV-2 in nasopharyngeal sample at days 3, 6, 9, 12, 15, and 28
Quantitative SARS-CoV-2 virus in blood at days 3, 6, 9, and 12

During the 15-day dosing period, it is anticipated that no more than 2 subjects out of 40 (5.0.0%) have an adverse event of grade 4 or 5 that is at least possibly related to VX-765. Should there be more than 2 subjects with an adverse event grade 4 or 5 that is at least possibly related to VX-765 in patients receiving VX-765, the study is put on an immediate clinical hold.

In addition, individual safety stopping rules include:

Reaching dose-limiting tolerability (DLT) before clinical improvement

Having a non-DLT respiratory adverse event >grade 3 during study medication inhalation that is at least possibly attributable to VX-765

Tolerability endpoints are referred to as the DLT and include wheezing/worsening of breathing.

The purpose of this randomized study is to obtain safety, tolerability and efficacy data in hospitalized patients with Covid-19 infection treated with VX-765 in addition to standard of care. The study drug/placebo is delivered every 8 hours for up to 15 days.

The study is conducted in two stages. Stage 1 is single-blind (patient is blinded, but the physicians and sponsor is unblinded), whereas Stage 2 is double-blind (patient and physician is blinded, sponsor is unblinded). In Stage 1, 24 patients is treated in groups of 4, randomized 1:1 to VX-765 or placebo and treated with escalating doses. The first group (n=4) is treated with VX-765 or placebo at 0.5 mg (in 2.5 mls normal saline). The second group (n=4) is treated with VX-765 or placebo at 1.0 mg (in 5 ml normal saline). Subsequent groups (each group n=4) is treated with VX-765 or placebo at 2.0 mg (in 10 mls normal saline), 3.0 mg (in 15 mls normal saline), 4.0 mg (in 20 mls normal saline) or 5.0 mg (in 25 mls normal saline). In Stage 2, 28 patients is randomized 1:1 to VX-765 or placebo at the highest dose without any drug-related adverse events, and another 28 patients is randomized 1:1 to VX-765 or placebo at the dose just below the highest dose without any drug-related adverse events.

| Stage 1 Single-Blinded Cohort | | |
|---|---|---|
| STAGE 1 | Randomization 1:1 | |
| Cohort (n = 24) | VX-765 + SOC* | Placebo + SOC* |
| 1 (n = 4) | 10 mg/kg | Placebo tablet |
| 2 (n = 4) | 12.5 mg/kg | Placebo tablet |
| 3 (n = 4) | 25 mg/kg | Placebo tablet |
| 4 (n = 4) | 50 mg/kg | Placebo tablet |
| 5 (n = 4) | 75 mg/kg | Placebo tablet |
| 6 (n = 4) | 100 mg/kg | Placebo tablet |

*SOC: Standard of Care
Note:
Based on a review of the safety and tolerability data of each dosing group, the DSMB has the option of allowing an additional 4 patients to be randomized to a dosing group

| Stage 2 Double-Blinded Cohort | | |
|---|---|---|
| STAGE 2 | Randomization 1:1[a] | |
| Cohort (n = 56) | VX-765 | Placebo |
| 1 (n = 28) | Highest dose at which no drug-related adverse events occurred in Stage 1 | Highest dose at which no drug-related adverse events occurred in Stage 1 |
| 2 (n = 28) | Next highest dose | Next highest dose |

[a]To balance the distribution of oxygen support between the two groups as an indicator of severe respiratory failure, randomization in Stage 2 is stratified on the basis of respiratory support methods at the time of enrollment: no oxygen support with nasal duct or mask, or high flow oxygen, noninvasive ventilation, or invasive ventilation including ECMO.

Approximately 80 subjects are entered at up to 10 sites in the USA. Hospitalized patients with illness of any duration are assessed for eligibility on the basis of a positive reverse transcriptase polymerase chain reaction (RT-PCR) assay or other commercial or public health assay for SARS-CoV-2 in a respiratory tract sample. Patients who test positive in any sample <72 hours prior to randomization are eligible. In addition to a positive SARS-CoV-2 test, patients are required to have crackles/rales and an SpO2≤94% on room air, or respiratory failure requiring supplemental oxygen/ventilation, or radiographic infiltrates by imaging (CT, CXR).

All eligible patients receive standard of care. Standard of care include supplemental oxygen, noninvasive and invasive ventilation, antibiotics, vasopressors and ECMO.

In addition, patients receive study medication/placebo, administered three times a day for up to 15 days. The lowest dose group receives 10 mg/kg orally. The highest dosing group receives 100 mg/kg orally. Medication is discontinued if the patient improves to the point where they can be discharged.

Patients are assessed daily for 15 days or until discharge, and again on days 12, 15, and 28. All data is entered into an EDC daily.

Subjects who prematurely discontinue study drug for any reason are asked to have an Early Termination (ET) visit the day the last study drug dose is administered.

Schedule of Events

| | Time Point (Days) | | | | | | | | | | | | |
|---|---|---|---|---|---|---|---|---|---|---|---|---|---|
| | D 1 | D 2 | D 3 | D 4 | D 5 | D 6 | D 7 | D 8 | D 9 | D 10 | D 12 | D 15 | D 28 |
| I/E | X | | | | | | | | | | | | |
| Consent | X | | | | | | | | | | | | |
| Demo | X | | | | | | | | | | | | |
| Meds | X | X | X | X | X | X | X | X | X | X | X | X | X |
| PE | X | | | | | | | | | | | | X |
| ECG | X | | | | | X | | | | X | | | X |
| SpO2 | X | X | X | X | X | X | X | X | X | X | X | X | X |

|  | Time Point (Days) | | | | | | | | | | | | |
| --- | --- | --- | --- | --- | --- | --- | --- | --- | --- | --- | --- | --- | --- |
|  | D 1 | D 2 | D 3 | D 4 | D 5 | D 6 | D 7 | D 8 | D 9 | D 10 | D 12 | D 15 | D 28 |
| Labs | X | | | | | | | | | X | | | X |
| Pregnancy | X | | | | | | | | | | | | |
| Temp | X | | X | | | X | | | X | | X | X | X |
| HR | X | | X | | | X | | | X | | X | X | X |
| SBP | X | | X | | | X | | | X | | X | X | X |
| RR | X | X | X | X | X | X | X | X | X | X | X | X | X |
| LOC | X | | X | | | X | | | X | | X | X | X |
| CXR | X | | | | | | | | | | | X | X |
| CT* | X | | | | | | | | | | | X | X |
| CoV-2 N/P | X | | X | | | X | | | X | | X | X | X |
| CoV-2 Blood | X | | X | | | X | | | X | | X | | |
| AE | X | X | X | X | X | X | X | X | X | X | X | X | X |
| NEWS | X | | X | | | X | | | X | | X | X | X |
| 7-POS | X | | X | | | X | | | X | | X | X | X |
| IP/Placebo | X | X | X | X | X | X | X | X | X | X | X | X | |
| COVID-19 immune labs | X | | X | | X | | | | X | X | X | X | X |

I/E: Inclusion/Exclusion criteria; Demo: Demographics; PE: Physical Examination; Labs: CBC and chemistry; Pregnancy testing: For women of child-bearing potential, using urine pregnancy kit (UPT); SpO2: peripheral Oxygen Saturation; 7-POS: 7-Point Ordinal Disease Severity Scale; NEWS: National Early Warning Score; AE: Adverse Event; LOC: Level Of Consciousness; CT*: CT scan is optional alternative to CXR; CXR: Chest X-Ray; CoV-2 N/P: Quantitative SARS-CoV-2 PCR from Nasopharyngeal swab sample; CoV-2 Blood: Quantitative SARS-CoV-2 PCR from blood sample. IP: Investigational product or placebo administration. COVID-19 immune labs include caspase-1, CBC with differential, T cell counts, LDH.

7-Point Ordinal Disease Severity Scale:

This is an assessment of the clinical status and it serves as the primary endpoint. The scale is as follows:

Not hospitalized, no limitations on activities

Not hospitalized, limitation on activities

Hospitalized, not requiring supplemental oxygen

Hospitalized, requiring supplemental oxygen

Hospitalized, on non-invasive ventilation or high flow oxygen devices

Hospitalized, on invasive mechanical ventilation or ECMO

Death

The NEW Score has demonstrated the ability to discriminate patients at risk of poor outcomes and is being used as an efficacy measure. This score is based on 7 clinical parameters:

Respiration rate

Oxygen saturation

Any supplemental oxygen

Temperature

Systolic blood pressure

Heart rate

Level of consciousness

Quantitative Nasopharyngeal SARS-CoV-2 RNA testing (RT-PCR):

Nasopharyngeal or throat swabs are used. Any FDA approved or commercial testing method is acceptable.

Quantitative blood SARS-CoV-2 RNA testing (RT-PCR):

Blood samples are used. Any FDA approved or commercial testing method is acceptable.

Study Population

Hospitalized patients with illness of any duration are assessed for eligibility on the basis of a positive reverse transcriptase polymerase chain reaction (RT-PCR) assay or other commercial or public health assay for SARS-CoV-2 in a respiratory tract sample. Patients who test positive in any sample <72 hours prior to randomization are eligible.

Number of Subjects

Approximately 80 subjects are entered at up to 10 sites in the USA.

Selection Criteria

Hospitalized patients with illness of any duration are assessed for eligibility on the basis of a positive reverse transcriptase polymerase chain reaction (RT-PCR) assay or other commercial or public health assay for SARS-CoV-2 in a respiratory tract sample. Patients who test positive in any sample <72 hours prior to randomization are eligible. In addition to a positive SARS-CoV-2 test, patients are required to have crackles/rales and an SpO2≤94% on room air, or respiratory failure requiring supplemental oxygen/ventilation, or radiographic infiltrates by imaging (CT, CXR).

Inclusion Criteria:

Subject (or legally authorized representative) provides written informed consent prior to initiation of any study procedures.

Understands and agrees to comply with planned study procedures

Agrees to the collection of nasopharyngeal swabs and venous blood per protocol.

Male or non-pregnant female adult ≥18 years of age at time of enrollment.

Laboratory confirmed SARS-CoV-2 infection as determined by PCR, or other commercial or public health assay in any specimen <72 hours prior to randomization.

Hospitalized patients with illness of any duration, and at least one of the following:

Clinical assessment (presence of crackles/rales) AND SpO2≤94% on room air OR

Acute respiratory failure requiring mechanical ventilation and/or supplemental oxygen OR Radiographic infiltrates by imaging (CT, CXR)

Women of childbearing age must agree to use contraception for the duration of the study.

Exclusion Criteria:

Pregnant or breast feeding

Uncontrolled, clinically significant heart diseases such as arrhythmias, angina or uncompensated congestive heart failure Non-hospitalized patients Discontinuation Criteria and Early Termination Procedures Subjects may withdraw voluntarily from participation in the study at any time and for any reason. Subjects may also be withdrawn on the basis of the Investigator's clinical judgment.

When a subject withdraws or is withdrawn before completing the study, the date and reason for withdrawal are to be documented. Subjects who withdraw or who are withdrawn prematurely are to attend an early discontinuation visit, at which time they complete all assessments as outlined in the Schedule of Events.

In the event that a subject is withdrawn prematurely due to an adverse event or serious adverse event, the adverse event or serious adverse event is followed until it resolves or stabilizes, or until it is judged by the investigator to be no longer clinically significant.

Concomitant and Prohibited Medication

Hydroxychloroquine

Non-study drug anti-viral agents such as lopinavir, remdesivir, ritonavir, ribavirin or interferon-1β

Any other medication not approved for the treatment of SARS-CoV-2.

All study medication contains VX-765 in a 300 mg tablet, which may be broken up depending on the dosage. The total dose administered is based on the total weight administered to the patient.

Packaging and Labelling

Study medication is supplied in blinded, single-use syringes packaged in kits. Each kit contains either drug product tablets only or placebo tablets only. Labelling clearly identifies that the tablets contain an investigational drug product but does not include any patient-specific information. The kit box labelling complies with regulatory requirements for investigational drug labelling and includes a pre-assigned individual medication ID number for randomization assignment and storage conditions. Individual syringes within the kit are not labelled with the medication ID number and should not be removed from the kit until time of use. Labelling includes a tamper-proof emergency use method for unblinding.

Storage, Dispensing and Reconciliation of Study Drug and Identity of Investigational Products All study medication should be stored at room temperature until dispensed. Storage in hospital should be in a locked and secure location accessible only to site staff involved with this study.

If a hospital becomes aware that study medication has not been properly handled, the sponsor must be contacted immediately. In such an event, study medication should not be utilized until the sponsor provides further direction.

Neither the investigator nor any study personnel distributes any study medication to any person not participating in this study. The study medication is administered at the discretion and direction of the investigator in accordance with the conditions specified in this protocol. It is the investigator's responsibility to ensure that accurate records of study medication issuance and return are maintained.

The sponsor is responsible for the tracking and accountability of study medication dispensed to hospitals and informs hospitals how to return or destroy study medication once it is no longer needed at the site.

Identification of Investigation Products

| Product Name | VX-765 |
|---|---|
| Dosage form | Tablet containing 300 mg VX-765 |
| Route/dosage | Oral. |

VX-765 doses are as follows:
10 mg/kg
12.5 mg/kg
25 mg/kg
50 mg/kg
75 mg/kg
100 mg/kg
(Placebo subjects receive same volume as treatment subjects at each dosing level)
Dosing Instructions. Oral
Observations and Measurements Subject informed consent must be obtained prior to conducting any study-related procedures. The informed consent can be signed by a next of kin if necessary. The Principal Investigator at each center ensures that the subject is given full and adequate oral and written information about the nature, purpose, possible risk and benefit of the study. Subjects must also be notified that they are free to discontinue from the study at any time. The subject should be given the opportunity to ask questions and allowed time to consider the information provided.

All assessments and procedures is completed according to the Schedule of Events.

Instructions to Subjects

VX-765 is administered by hospital staff. There are no specific instructions to patients.

Warnings and Precautions

Pre-Existing Medical Conditions

All subjects enrolled in the study have SARS-CoV-2 infection and respiratory symptoms.

Treatment Emergent Adverse events

A treatment-emergent adverse event (TEAE) is defined as any event not present prior to the initiation of the treatments or any event already present that worsens in either intensity or frequency following exposure to the treatments.

An adverse event is typically collected after signing the informed consent form and could be related or unrelated to the study drug. A TEAE is for after the subject actually takes the study drug.

Separate summaries for adverse events that occur during treatment (summary of treatment emergent adverse events) is provided.

Laboratory Abnormalities

Clinical labs is performed by each hospital in their own laboratories. Labs to be drawn during the study include serum chemistries, a hematology panel and coagulation panel. A serum pregnancy test must be performed, and the result must be negative prior to the entry of women of child-bearing potential. COVID 19 immune labs (such as (caspase-1, CBC with differential, T cell counts, LDH) are also performed.

Clinical laboratory reports must be reviewed by a physician for out-of-range values within 12 hours of receipt. Out-of-range values is evaluated using the following notations:

NS: Not clinically significant
LE: Laboratory Error
PT: Subject abnormal; relates to the subject's usual state of health
CS: Clinically Significant. This value cannot be explained by any of the other flags.

By definition a lab value flagged as "CS" must be entered on the adverse clinical laboratory event page in the CRF. A laboratory test flagged "CS" must be repeated as soon as possible. The investigator may use his/her own judgment as to whether the abnormal finding is sufficient reason to immediately withdraw the subject from the study.

If a laboratory value is considered to be serious and life-threatening and at least possibly attributable to the study drug, the subject should be immediately discontinued from the study and appropriate therapy started.

Adverse Event Assessment and Recording

All adverse events, exacerbations of concomitant illnesses, or events known to be related to underlying disease processes or concomitant medications are to be recorded on the CRF throughout the study. If a pre-existing condition worsens on study, the date on which the exacerbation began should be recorded. Onset dates for study treatment-related adverse events must be on or after the date of initial study treatment use. The need to record an adverse event on the CRF is not dependent on whether the adverse event is associated with the use of the study medication. In order to avoid vague, ambiguous or colloquial expressions, the adverse event should be recorded in standard medical terminology.

Adverse event recording includes the date of onset, severity, duration, whether or not the study medication was discontinued because of the event, the treatment given and the outcome. The investigator must also assess whether the event was related to the study medication, concurrent drug therapy, underlying disease, a combination of these factors, or if it is unknown. Subjects with an adverse event should be carefully followed to determine outcome.

The investigator uses the National Cancer Institute (NCI) definitions to grade the severity of the event.

Grade 1: Mild; asymptomatic or mild symptoms; clinical or diagnostic observations only; intervention not indicated Grade 2: Moderate; minimal, local, or non-invasive intervention indicated; limiting age-appropriate ADL Grade 3: Severe or medically significant but not immediately life-threatening; hospitalization or prolongation of hospitalization indicated; disabling; limiting self-care ADL.

Grade 4: Life-threatening consequences; urgent intervention indicated

Grade 5: Death

The relationship or association of the study medication in causing or contributing to the adverse event is characterized as remote, possible or probable as defined below:

Not related: Evidence indicates no plausible direct relationship to the study medication Remote: Suggests other conditions are reasonably likely to account for the event including concurrent illness, progression or expression of the disease state, or reaction to concurrent medication Possible: Suggests that the association of the event with the study medication is unknown; however, the adverse event is not reasonably supported by other conditions Probable: Suggests that a reasonable temporal sequence of the event with medication administration exists and, based upon the investigator's clinical experience, the association of the event with study medication seems likely Definite: Suggests that based upon the investigator's experience, the association of the event with the study medication seems very certain.

Procedures such as surgery should not be recorded as adverse events. However, the medical condition for which the procedure was performed should be reported if it meets the definition of adverse event.

Reporting Requirements

Any adverse event, including both observed or volunteered problems, complaints, or symptoms that begins any time between the start of the first dose and within 30 days after the end of the last dose are to be recorded briefly on the appropriate CRF and in detail in the source documents. A check list of adverse events may not be used during this study.

The following are specific definitions that are relevant to meeting your reporting obligations and which are included in the FDA Regulations, 21 CFR Part 312.32, and International Conference on Harmonization of Technical Requirements for Registration of Pharmaceuticals for Human Use (ICH) Guidelines:

Adverse Event: Any untoward medical occurrence in a subject administered a pharmaceutical product and which does not necessarily have to have a causal relationship with this treatment. An adverse event can be any unfavorable sign (including an abnormal laboratory finding), symptom, or disease temporally associated with the use of the investigational drug, whether or not considered related to the investigational drug.

Serious Adverse Event: An untoward event or reaction that at any dose:

results in death is life-threatening prolongs existing hospitalization results in permanent or significant disability or incapacity requires intervention to prevent permanent impairment/damage Life-threatening: An event which a subject was at risk of death at the time of event.

There is a distinction between the severity and the seriousness of an adverse event. Severe is a measurement of intensity, thus a severe reaction is not necessarily a serious adverse event. For example, a headache may be severe in intensity, but would not be serious unless it met one of the criteria for serious adverse events listed previously.

Serious Adverse Events

Adverse events (AEs) and serious adverse events (SAEs) are collected from the first dose of IP is administered until 28 days after the last dose of IP. Medical occurrences that began prior to the start of study treatment, but after obtaining informed consent were recorded on the Medical History/Current Medical Conditions CRF. The investigator or site staff is responsible for the detection and documentation of events meeting the criteria and definition of an adverse event or serious adverse event, as provided in the study protocol. However, any SAEs assessed as related to study participation (e.g., dosing, protocol mandated procedures, invasive tests, or change in existing therapy) or related to a concomitant medication is recorded from the time a subject consent to participate in the study up to and including any follow-up contact.

In the event of an AE or SAE, it is the responsibility of the Investigator to review all documentation (e.g., hospital progress notes, laboratory, and diagnostics reports) relative to the event and attempt to establish a diagnosis of the event based on signs, symptoms, and other clinical information. The diagnosis was to be documented as the adverse event or serious adverse event and not the individual's signs/symptoms. Once an Investigator becomes aware that a SAE has occurred in a study subject, they are' to report the information within 24 hrs and provide an assessment of causality.

Notification of Serious Adverse Events

Under IND regulations, 21 CFR Part 312.64, investigators are required to notify the Sponsor promptly, within 24 hours of the sites' notification of any SAEs, deaths, or life-threatening problems with the investigational drug. This regulation also requires that if the adverse event is alarming, the investigator must notify the Sponsor immediately.

A Serious Adverse Event (SAE) is a significant hazard, contraindication, or precaution considered to be serious. This includes, but is not limited to, blood dyscrasias, endocrine disturbances, hemorrhage from any site, or severe skin disorder. Additional examples are intensive treatment for allergic bronchospasm, blood dyscrasias or convulsions.

Subjects who experience a SAE must be given appropriate examinations and treatment. The investigator must provide written information to the sponsor as soon as possible.

When an investigator is in doubt when to report an event, the investigator should err on the side of caution.

All appropriate SAEs is reported immediately to appropriate regulatory authorities by the Sponsor. A copy of all FDA reportable serious adverse events is mailed to all investigators participating in ongoing clinical studies with the study medication in order to permit prompt notification of the appropriate institutional review board (IRB).

Departure from Protocol for Emergency or Adverse Event

In medical emergencies, the investigator should use medical judgment and remove the subject from immediate hazard and decide whether the subject may continue in the study. The IRB should also be notified as to the type of emergency and the course of action. The CRF for the subject must describe the departure from the protocol and state the reason.

Safety Monitoring

A Data Safety and Monitoring Board (DSMB) has been established to monitor the safety of the subjects during the study. The DSMB includes members who are independent of this study and its Sponsor Team with relevant clinical expertise, including a good understanding of the safety of medications for respiratory illnesses. These members include a statistician, an infectious disease specialist and/or a pulmonologist. The methodology and the operating procedures for the safety reviews is developed by the infectious disease specialist and/or pulmonologist in collaboration with the sponsor and is documented in the DSMB Charter. The DSMB is not blinded. They review all SAEs and determine whether the study can proceed or whether protocol modifications are required.

Stopping Rules

During the 15-day dosing period, it is anticipated that no more than 2 subjects out of 40 (5.0%) have an adverse event of grade 4 or 5 that is at least possibly related to VX-765. Should there be more than 2 subjects with an adverse event grade 4 or 5 that is at least possibly related to VX-765 in the cohort of subjects, the study is put on an immediate clinical hold.

In addition, individual safety patient study stopping rules include:

Reaching dose-limiting tolerability (DLT) before clinical improvement

Having a non-DLT respiratory adverse event >grade 3 within 24 hours of taking study medication that is at least possibly attributable to VX-765

Follow-Up and Final Reports

The investigator shall provide an accurate final report within 1 month after completion, termination or discontinuation of the study. The final report may not precede completion of monitoring relevant CRFs.

Regulatory Aspects

Neither the investigator shall modify this protocol without first obtaining concurrence of the other in writing. All changes must be submitted to the IRB. Protocol modifications which impact subject safety, or the validity of the study must be approved by the IRB and submitted to the FDA before implementation. In the case of a medical emergency to increase safety of subjects, a change may be made after discussion with the sponsor. In these instances, the IRB and FDA is notified as soon as possible.

The following populations are considered for statistical analyses.

Safety Population: The Safety Population consists of all patients who receive at least one dose of study drug.

Efficacy Evaluable Population: The Efficacy Evaluable Population includes all patients in the Safety Population who complete the dosing period with no major protocol violations.

Analysis Methods

General Methods

Details of the statistical analysis methodology is provided in a separate statistical analysis plan (SAP), which is finalized prior to the interim analysis being performed.

Continuous variables are summarized using the number of observations, number of observations above the limit of quantification (if applicable), mean, standard deviation (SD) median, and range. Categorical variables is summarized using frequency counts and percentages.

Analysis of Subject Disposition, History, and Baseline Characteristics

Subject disposition, including analysis population allocation, subjects enrolled, completed each period, discontinued, and primary reason for discontinuation, is summarized using frequency and percentage.

Protocol deviations is summarized using frequency and percentage.

Medical history data and prior and concomitant medications is summarized using frequency and percentage.

Subjects' age, height, weight, and baseline disease characteristics is summarized using descriptive statistics. Gender, race, and other categorical variables is provided using frequency and percentage.

Safety Analyses

All safety analyses are performed on the Safety Population. The safety data is presented in individual listings and summary tables summarizing results by cohort and treatment group.

Adverse Events

AEs are coded according to the latest version of the Medical Dictionary for Regulatory Activities (MedDRA). The intensity/severity of AEs is graded according to NCI CTCAE.

TEAEs, AEs leading to study treatment discontinuation, AEs leading to dose interruption, AEs related to study medication, SAEs, and AEs leading to death are summarized by system organ class, preferred term, and study period. A summary of AEs that are CTCAE Grade 3 or higher, as well as the most frequent preferred terms, is provided.

If a subject experiences the same preferred term multiple times within a period, then the event is counted only once within the period and by greatest severity.

Descriptive statistics are used to summarize the safety data both by treatment group and overall.

Clinical Laboratory Values

All laboratory test results are summarized by period together with the change from baseline. The frequency distribution for low/normal/high or normal/abnormal is summarized as well. The denominators for calculating the percentages are based on the number of subjects with non-missing values in the Safety Population.

Vital sign results are summarized by period, together with the change from baseline.

Summaries of physical examinations present frequency distribution of abnormal findings by body system and period. The denominators for calculating the percentages are based on the number of subjects evaluated for a particular body system of each dose level in the Safety Population.

Electrocardiogram (EKG) findings are classified as normal vs abnormal. The number and percentage of each category are summarized using frequency table for each period. The denominators for calculating the percentages are based on the number of subjects with non-missing values in each period.

Tolerability is measured by DLT endpoints.

The frequency of occurrence for each tolerability endpoint including wheezing and increasing difficulty in breathing is summarized by cohort and treatment group. Percentages are based on the number of subjects in each dosing level in the Safety Population.

Efficacy Analyses

Primary Efficacy Endpoint Analyses

Summary statistics are provided for Stage 1, in Stage 2 inferential statistics are also performed.

Stage 2 Primary Efficacy Endpoint Analyses

The primary efficacy endpoint analysis is a treatment group comparison of the patients' day 15 7-point ordinal disease severity scale using a Cochran-Mantel-Haenszel (CMH) row mean score difference test controlling for the baseline score. The primary efficacy analysis compares the pooled Stage 2 placebo groups to the pooled Stage 2 VX-765 groups at the two-sided 0.05 Type I error rate.

The primary efficacy analysis is performed on the Safety population.

Sensitivity analyses for the primary efficacy endpoint including comparing the individual VX-765 groups to placebo are specified.

Stage 2: Secondary Efficacy Endpoint Analyses

The Stage 2 secondary efficacy endpoint analysis methods are specified.

Handling of Missing Data

The approaches to handling missing data are specified.

Sample Size/Power Considerations

For Stage 1, the sample size of 4 subjects per group (2 on VX-765, 2 on placebo) is designed to provide an initial assessment of safety and tolerability for the initial doses of VX-765. The Stage 2 sample size of 28 patients in an VX-765 treatment group (i.e., the 2 VX-765 treatment groups combined) provides a 95% probability that an AE with an underlying rate of 10% occurs in these patients. Additionally, in Stage 2, a sample size of 28 patients per group (i.e., pooling the Stage 2 placebo groups and the VX-765 groups) provides approximately 80% power to detect a treatment difference at the 2-sided 0.05 Type I error rate based on a using a CMH row mean score difference test controlling for the baseline score. This assumes the following day 15 distribution for the seven-category disease severity score. Power was estimated based on the distribution of scores presented using the Mantel-Haenszel mean score statistic with modified ridit scoring.

Distribution of 7-point Ordinal Disease Severity Scale at 15 Days for Power Calculations

| | 7-Point Ordinal Disease Severity Scale | | | | | | |
|---|---|---|---|---|---|---|---|
| | 1 | 2 | 3 | 4 | 5 | 6 | 7 |
| VX-765 | 30% | 30% | 20% | 13% | 1% | 1% | 5% |
| Placebo | 10% | 20% | 20% | 20% | 5% | 5% | 20% |

This study has an estimated maximum duration of up to 4 weeks for each subject. The study duration from first subject enrolled to last subject out is expected to be 6 months.

The Principal Investigator(s) at each center ensures that the subject is given full and adequate oral and written information about the nature, purpose, possible risk and benefit of the study. Subjects must also be notified that they are free to discontinue from the study at any time. The subject should be given the opportunity to ask questions and allowed time to consider the information provided.

The subject's informed consent must be obtained before conducting any study procedures.

During the study, a dedicated Clinical Research Associate (CRA) has regular contacts with the investigational site, for the following:

Provide information and support to the investigator(s)

Confirm that facilities remain acceptable

Confirm that the investigational team is adhering to the protocol, that data are being accurately recorded in the eCRFs, and that investigational product accountability checks are being performed Perform source data verification. This includes a comparison of the data in the eCRFs with the subject's medical records at the hospital or practice, and other records relevant to the study. This requires access to all original records for each subject (e.g. clinic charts) as described in the study monitoring plan.

The CRA is available over the course of the study if the investigator(s) or other staff needs information or advice. Remote and central monitoring visits are conducted until it is possible to perform on-site visits.

Audits and Inspections

Authorized representatives of a regulatory authority, an Independent Ethics Committee (IEC) or an Institutional Review Board (IRB) may visit the site to perform audits or inspections, including source data verification. The purpose of an audit or inspection is to systematically and independently examine all study-related activities and documents to determine whether these activities were conducted, and data were recorded, analyzed, and accurately reported according to the protocol, Good Clinical Practice (GCP) guidelines of the International Conference on Harmonization (ICH), and any applicable regulatory requirements.

Ethics Committee Review

The final study protocol, including the final version of the Informed Consent Form, must be approved or given a favorable opinion in writing by an IRB or IEC as appropriate.

The Principal Investigator is responsible for informing the IRB or IEC of any amendment to the protocol in accordance with local requirements. In addition, the IRB or IEC must approve all advertising used to recruit subjects for the study. The protocol must be re-approved by the IRB or IEC upon receipt of amendments and annually, as local regulations require.

The Principal Investigator is also responsible for providing the IRB with reports of any reportable serious adverse drug reactions from any other study conducted with the investigational product.

Progress reports and notifications of serious adverse drug reactions are provided to the IRB or IEC according to local regulations and guidelines.

The study is performed in accordance with ethical principles that have their origin in the Declaration of Helsinki and are consistent with ICH/GCP, applicable regulatory requirements on Bioethics.

Any research information obtained about the subject in this study is kept confidential. A subject is not identified by name, only by his/her initials. The subject's name or any identifying information does not appear in any reports published as a result of this study.

However, information obtained from individual subject's participation in the study may be disclosed with his/her consent to the health care providers for the purpose of obtaining appropriate medical care. The subject's medical records/charts, tests with his/her name on them may be made available to the appropriate contract research organization (CRO), its potential eventual partners, and any other regulatory authorities. This is for the purpose of verifying information obtained for this study. Confidentiality is maintained throughout the study within the limits of the law.

A subject's name is not given to anyone except the researchers conducting the study, who have pledged an oath of confidentiality. All identifying information is kept behind locked doors, under the supervision of the study Investigator and is not transferred outside of the investigator site.

A subject may take away his/her permission to collect, use and share information about him/her at any time. If this situation occurs, the subject is not able to remain in the study. No new information that identifies the subject is gathered after that date. However, the information about the subject that has already been gathered and transferred may still be used and given to others as described above in order to preserve the scientific integrity and quality of the study.

The site maintains records of study treatment delivered to the study site; the inventory at the site; the administration to each subject; and the return of materials for storage or disposal. These records should include dates, quantities, batch/serial numbers, expiration dates, in-clinic temperature log, and unique code numbers assigned to the product and study subjects.

Investigator maintains records that document adequately that the subjects were provided with the correct study drug and reconciles the products received from the drug dispensing center. Investigational product is not returned until accountability has been fully monitored.

Modifications to the protocol are only possible by approved protocol amendments. All protocol amendments are approved by the appropriate regulatory authorities as well as each institutional review board prior to implementation. The Investigator must not implement any deviations from, or changes to the protocol, except where it is necessary to eliminate an immediate hazard to the study subject.

The protocol must be read thoroughly, and the instructions followed exactly. Any deviation to the protocol has to be reported as soon as possible to Clinical Research Associate/designee. The governing reporting guidelines for protocol deviations must be adhered to by the Investigator.

This study may be prematurely terminated, if in the opinion of the Investigator, there is sufficient reasonable cause. Written notification documenting the reason for study termination is provided to the Investigator by the terminating party. Circumstances that may warrant termination include, but are not limited to:

Determination of unexpected, significant, or unacceptable risk to subjects.

Failure to enroll subjects at an acceptable rate.

Insufficient adherence to protocol requirements.

Insufficient complete and/or evaluable data.

Plans to modify, suspend, or discontinue the development of VX-765.

Should the study be closed prematurely, all study materials must be returned.

Inspection of Records

The Investigator agrees to allow inspection of the drug storage area, study drug stocks, drug accountability records, subject charts and study source documents, and other records relative to study conduct.

All data relating to study procedures is entered on to eCRFs. All forms must be completed electronically. All requested information must be entered in the eCRF. Sites are trained on the eCRF Completion Guidelines which provided instructions on how to enter the required data in the Electronic Data Capture (EDC) system.

eCRFs are completed for each subject. It is the Investigator's responsibility to ensure the accuracy, completeness, and timeliness of the data entered in each subject's eCRF. Source documentation supporting the eCRF data should indicate the subject's participation in the study and document the dates and details of study procedures, adverse events, and subject status.

The Investigator, or designee, should complete the eCRF as soon as possible after information is collected, preferably on the same day that a subject is seen for an examination, treatment, or any other study procedure. Any outstanding entries must be entered immediately after the final examination. An explanation should be given for all missing data.

Study records and source documents must be preserved for the longer of (i) two (2) years following completion of the study; or (ii) two (2) years following the termination or withdrawal of the Investigational New Drug application under which this study was conducted; or (iii) the period required by local, state, and federal laws, regulations and FDA Guidance.

The Investigator agrees to comply with all applicable federal, state, and local laws and regulations relating to the privacy of subject health information, including, but not limited to, the Standards for Individually Identifiable Health Information, 45 CFR, Parts 160 and 164 (the Health Insurance Portability Accountability Act of 1996 [HIPAA] Privacy Regulation). The Investigator shall ensure that study subjects authorize the use and disclosure of protected health information in accordance with HIPAA Privacy Regulation.

Participating sites, the study database, and study documentation including subject medical records may be subject to a quality assurance audit during the course of the study. In addition, inspections may be conducted by regulatory bodies at their discretion.

Laboratory Tests

| Hematology/Immunology | Serum Chemistry | Urinalysis |
| --- | --- | --- |
| White Blood Cell (WBC) Count | Albumin | Appearance |
| Red Blood Cell (RBC) Count | Alanine Aminotransferase (ALT) | pH |
| Hemoglobin (Hb) | Alkaline Phosphatase (ALP) | Protein |

-continued

| Hematology/Immunology | Serum Chemistry | Urinalysis |
|---|---|---|
| Hematocrit (Hct) | Aspartate Aminotransferase (AST) | Glucose |
| Mean Corpuscular Volume (MCV) | Blood Urea Nitrogen (BUN)/Creatinine | Ketone Bodies |
| Red Blood Cell Distribution Width (RDW) | Ratio | Indicators of Blood and WBCs |
| | Calcium | Specific Gravity |
| Platelet Count | Carbon Dioxide | Urobilinogen |
| ESR sedation rate | Chloride | |
| Differential - absolute and percent of: | Creatinine | |
| | Glucose | |
| Neutrophils | Magnesium | |
| Lymphocytes | Potassium | |
| Monocytes | Sodium | |
| Eosinophils | Total Bilirubin | |
| Basophils | Total Protein | |
| COVID-19 immune panel | Urea Nitrogen | |
| (Caspase-1 levels in T cells and | Lactate Dehydrogenase (LDH) | |
| lymphocytes, and absolute counts | Creatine Kinase, Total | |
| and % of CD3+ T cells, CD4+ T | | |
| cells, CD8+ T cells) | | |

Pregnancy tests
A serum pregnancy test is performed on all female subjects of child-bearing potential at the screening visit. Urine Pregnancy Test (on site): Urine human chorionic gonadotropin (HCG) (pre-menopausal females only)

Example 4: Safety, Tolerability, and Treatment Effect of Belnacasan in Patients with COVID-19: A Proof of Concept Randomized, Double-Blind, Placebo-Controlled Trial of Orally Administered Belnacasan Tablets for the Treatment of Mild to Moderate COVID-19

Abbreviations

9-POS 9-Point Ordinal Disease Severity Scale
ADL Activities of daily living
AE Adverse event
ALC Absolute lymphocyte count
ALP Alkaline phosphatase
ALT Alanine aminotransferase
AST Aspartate aminotransferase
BMI Body mass index
CFR Code of Federal Regulations
CRF Case report form
CRP C-reactive protein
CS Clinically significant
CT Computed tomography
COVID-19 Coronavirus disease 2019
CTCAE Common terminology criteria for adverse events
CXR Chest x-ray
DLT Dose limiting toxicity
DSMB Data and safety monitoring board
ECMO Extracorporeal membrane oxygenation
EDC Electronic data capture
EKG Electrocardiogram
ET Early termination
FDA Food and Drug Administration
G-CSF Granulocyte colony-stimulating factor
GCP Good Clinical Practice
GGT Gamma-glutamyl transferase
HIPAA Health Insurance Portability and Accountability Act
HR Heart rate
I/E Inclusion/Exclusion
ICH International Council for Harmonization
IDS Investigational Drug Services
IND Investigational New Drug
IP Investigational product
IRB Institutional review board
LAR Legally authorized representative
LDH Lactate dehydrogenase
LOC Level of consciousness
NCS Not clinically significant
PE Physical examination
P-gp P-glycoprotein
QID Four times a day
RP MedStar Health Research Pharmacy
RR Respiratory rate
RT-PCR Reverse transcriptase polymerase chain reaction
SAE Serious adverse events
SAP Statistical analysis plan
SARS Severe acute respiratory syndrome
SBP Systolic blood pressure
SOC Standard of care
SpO2 Peripheral capillary oxygen saturation
TID Three times a day
TNF-α Tumor necrosis factor alpha
WHC Washington Hospital Center
WHO World Health Organization Safety, tolerability, and treatment effect of belnacasan in patients with COVID-19: A phase 2, proof of concept randomized, double-blind, placebo-controlled trial of orally administered belnacasan tablets for the treatment of mild to moderate COVID-19

Study Phase. 2/Proof of Concept

Methodology. This study is conducted as a proof of concept safety, tolerability and treatment effect Phase 2 trial in subjects with confirmed SARS-CoV-2 infection and mild to moderate COVID-19.

In this hypothesis generating, randomized, double-blind, placebo-controlled trial, 24 subjects are given 900 mg TID of belnacasan and 24 subjects are given a placebo TID. Belnacasan or placebo are given for 28 days and assessments of safety, tolerability, and treatment effect is performed for 60 days. Subjects in both treatment arms are also treated with the background standard of care that is at that time appropriate and commensurate with their COVID-19 disease severity.

Subjects use a diary to record study drug intake as well as symptoms and activity levels; assess physical parameters using a study-provided thermometer and pulse oximeter; be assessed at regular intervals via telemedical and in-person follow-up clinic visits; and give blood for laboratory tests. A Data Safety & Monitoring Board (DSMB) is engaged throughout for data monitoring and safety evaluation.

Study Duration. Subjects are in the study for 60 days. The study lasts 3-6 months.

Study Centers. This study is conducted at Washington Hospital Center (WHC) and/or other MedStar hospital and/or critical or clinical care sites.

Objectives. The purpose of this trial is to assess the safety, tolerability and treatment effect of the orally administered Caspase-1 inhibitor, belnacasan, for the treatment of patients with mild to moderate COVID-19 and to generate hypotheses for future trials.

Primary Objective: To determine the safety and tolerability of belnacasan (VX-765/RVT-201/MSR-001) administered orally for 28 days in subjects with mild to moderate COVID-19 as determined by Adverse Events and Serious Adverse Events.

Secondary Objective: To generate data on the treatment effect of belnacasan (VX-765/RVT-201/MSR-001) administered orally for 28 days in subjects with mild to moderate COVID-19 as determined by its effect size on outcomes in five areas:

Clinical recovery and resolution of COVID-19 symptoms
Physical functions and parameters relevant to COVID-19
COVID-19 related deterioration and mortality
WHO 9-point ordinal scale for clinical improvement
Surrogate markers of COVID-19-related inflammation and organ involvement The hypothesized end result of treatment with belnacasan would be to reduce the symptomatic and clinical burden, length of disease course, and disease progression of COVID-19.

Number of Subjects. The intent is to enroll 48 subjects to participate in a 1:1 allocation in this randomized, double-blind, placebo-controlled safety, tolerability and treatment effect trial.

Study Description. A Phase 2, proof of concept randomized, double-blind, placebo-controlled trial of orally administered belnacasan tablets for the treatment of mild to moderate COVID-19. Belnacasan or placebo is administered for 28 days and follow-up occurs for 60 days, alongside background standard of care.

Study Population. Subjects with an RT-PCR assay confirmed SARS-CoV-2 infection and mild to moderate COVID-19 at time of enrollment.

Study Drug Administration. Oral, three times per day as per protocol.

Inclusion/Exclusion Criteria. The study population is defined as subjects who meet the following criteria:

Inclusion Criteria:

Subject (or legally authorized representative) provides written informed consent prior to the initiation of any study procedures.

Subject understands and agrees to comply with planned study procedures, including using the diary.

Subject agrees to the collection of nasopharyngeal swabs and venous blood per protocol.

Subject is male or non-pregnant female adult ≥18 years of age at time of consent.

Women with a history of menstruation must agree to use two methods of contraception, at least one of which is highly effective, for the duration of the study as well as to undergo additional pregnancy testing during the study.

Subject has a laboratory confirmed SARS-CoV-2 infection as determined by RT-PCR assay prior to enrollment.

Subject has evidence of either mild or moderate COVID-19 illness of less than 7 days from first onset, with minimal baseline symptom severity based on patient-reported FDA scoring system defined as follows:

Subject presents with at least two common symptoms of COVID-19 from the following list: stuffy or runny nose, sore throat, cough, low energy or tiredness, muscle or body ache, headache, chills or shivering, feeling hot or feverish, nausea, vomiting, diarrhea, shortness of breath with exertion (without supplemental oxygen requirement) with a score of 2 or higher; impairment in sense of smell or taste with a score of 1 or higher OR Subject presents with any (i.e., at least one) symptom of COVID-19 as defined above AND clinical evidence of moderate COVID-19 as defined by FDA guidance for industry (such as respiratory rate >20 breaths per minute, heart rate >90 beats per minute, with oxygen saturation >93% on room air at sea level).

Subject presents with high-risk for COVID-19-related inflammation determined by at least one comorbidity, including obesity, diabetes, hypertension, stable heart disease, respiratory disease, or non-severe fatty liver disease and/or age >60 years.

Subject's overall health condition is deemed as suitable to fully and safely participate in this trial as determined by the Investigator.

Exclusion Criteria

Any clinical signs indicative of severe or critical COVID-19 as defined by FDA guidance for Industry at the time, including SpO2<93% and/or oxygen requirement.

Hospitalization for COVID-19, or consideration thereof

ICU level of care and/or non-mechanical/mechanical ventilation and/or oxygen supplementation at time of enrollment.

Pregnant or breast-feeding subjects.

Subjects who cannot swallow tablets.

History of any pre-existing organ impairment, such as:

Severe kidney disease (known or estimated GFR <30 mL/minute) or on dialysis.

Uncontrolled, clinically significant heart diseases such as arrhythmias, angina or heart failure as defined by AHA/ACC Grade C and D.

Chronic respiratory disease requiring supplemental oxygen.

Moderate and severe hepatic impairment as defined by Child-Pugh scoring Class B and Class C Elevated liver function tests (determined by ALT, AST, GGT, or ALP >2× upper limit of normal, and total Bilirubin >upper limit of normal).

History of malignancy or immunodeficiency within the prior 5 years.

Acute respiratory illness other than COVID-19.

Active bacterial, viral or fungal infection (including HIV, hepatitis B, hepatitis C).

While dosed with the IP, the taking of prohibited concomitant medication or the ingestion of food that interferes with the IP, including:

Non-COVID19-related anti-viral medication such as lopinavir, ritonavir, ribavirin or interferon-1β.

Systemically administered immunosuppressive and anti-inflammatory agents, other than background standard of care for COVID-19 at the time.

Drugs and foods that are potent inhibitors or inducers of CYP3A4 and/or P-gp, as listed in FDA "Drug Development and Drug Interactions: Table of Substrates, Inhibitors and Inducers", including (including herbal medications such as St. John's Wort) within 30 days or 5 half-lives (whichever is longer) prior to the first dose of study drug.

Any other diseases or medical conditions or concomitant medications that are deemed as not compatible or appropriate for the subject's ability to fully and safely participate in this trial as determined by the Investigator.

Study Product, Dose, Route, Regimen. 48 subjects participate in this randomized, double-blind, placebo-controlled safety, tolerability and treatment effect trial. In a 1:1 allocation, 24 subjects receive 900 mg (three tablets each containing 300 mg) TID of orally administered belnacasan and 24 subjects receive placebo tablets (three placebo tablets) TID, whereby randomization is determined via a randomization table.

Study Endpoints. Primary Endpoint:

Incidence of Adverse Events and Serious Adverse Events assessed out to day 60.

Secondary Endpoints:

Secondary endpoints relate to generating data on the treatment effect of belnacasan as determined by its effect size on outcomes in five areas:

1. Clinical Recovery and Resolution of COVID-19 Symptoms

1a. Sustained recovery and resolution rates of common COVID-19 symptoms:

(i.e., stuffy or runny nose, sore throat, cough, low energy or tiredness, muscle or body ache, headache, chills or shivering, feeling hot or feverish, nausea, vomiting, diarrhea, shortness of breath with exertion; impairment in sense of smell or taste)

Proportion of subjects in treatment group versus placebo group, respectively, who per symptom questionnaire on days 4, 7, 10, 14, 21, 28, 42, 60 post randomization have achieved for two consecutive days:

scores not higher than 0 for all symptoms scores not higher than 1 for all symptoms scores not higher than 0 for all symptoms other than impairment of taste or smell scores not higher than 1 for all symptoms other than impairment of taste or smell 1b. Sustained improvement of global impression rates: Proportion of subjects in treatment group versus placebo group, respectively, who per symptom questionnaire on days 4, 7, 10, 14, 21, 28, 42, 60 post randomization have answered for two consecutive days "Yes" to "In the past 24 hours, have you returned to your usual health (before your COVID-19 illness)?"

"Yes" to "In the past 24 hours, have you returned to your usual activities (before your COVID-19 illness)?"

"None" to "In the past 24 hours, what was the severity of your overall COVID-19 related symptoms at their worst?"

"Mild" to "In the past 24 hours, what was the severity of your overall COVID-19 related symptoms at their worst?"

1c. Time to sustained recovery, resolution or improvement: comparison in treatment group versus placebo group, respectively of the number of days from randomization to the first day of achieving each item in 1a and 1b above.

2. Physical Functions and Parameters Relevant to COVID-19

2a. Parameter rates: Proportion of subjects in treatment group versus placebo group, respectively, who on days 4, 7, 10, 14, 21, 28, 42, 60 post randomization per thermometer or pulse oximeter reading experienced:

fever at any point between enrollment and day 2 post randomization and who were afebrile <38C oxygenation of SpO2>=96% or >93% in room air when resting 2b. Time to and length of parameters: comparison in treatment group versus placebo group, respectively of the number of days from randomization to the first day of achieving sustained (i.e., at least 2 days) resolution of fever for subjects who presented with fever at any point between enrollment and day 2 post randomization with temperature <38C or >=38C experienced in total during the first 28 days post randomization from randomization to the first day post randomization of achieving oxygenation of SpO2>=96% in room air when resting for subjects who presented with SpO2>93% and <96% in room air, when resting, at enrollment with oxygenation of SpO2>=96% or SpO2>93% in room air, when resting, in total during the first 28 days post randomization 3. COVID-19 Related Deterioration and Mortality 3a. Deterioration and mortality rates: Proportion of treatment group, versus placebo group, respectively, who per subject reporting or medical records by day 14, day 28 and by day 60 post randomization had experienced:

an emergency department visit, other than at study enrollment or study visits hospitalization for COVID-19 hospitalization for COVID-19 requiring oxygen hospitalization for COVID-19 requiring ICU hospitalization for COVID-19 requiring ventilation COVID-19 related death death hospitalization or death 3b. Time to and length of deterioration: Comparison of treatment group versus placebo group, respectively, in the number of days from randomization until the first day of experiencing hospitalization for COVID-19 of hospitalization for COVID-19 experienced in total by day 14, by day 28 and by day 60 post randomization of hospitalization for COVID-19 requiring oxygen experienced in total by day 14, by day 28 and by day 60 post randomization of hospitalization for COVID-19 requiring ICU experienced in total by day 14, by day 28 and by day 60 post randomization of hospitalization for COVID-19 requiring ventilation experienced in total by day 14, by day 28 and by day 60 post randomization 4. WHO 9-Point Ordinal Scale 0. Uninfected or "no clinical or virological evidence of infection"

defined as subject answering "Yes" to "In the past 24 hours, have you returned to your usual health (before your COVID-19 illness)?"

1. Not hospitalized, no limitations on activities defined as subject answering "Yes" to "In the past 24 hours, have you returned to your usual activities (before your COVID-19 illness)?"

2. Not hospitalized, limitation on activities defined as subject answering "No" to "In the past 24 hours, have you returned to your usual activities (before your COVID-19 illness)?"

3. Hospitalized, not requiring supplemental oxygen

4. Hospitalized, requiring supplemental oxygen

5. Hospitalized, on non-invasive ventilation or high flow oxygen devices

6. Hospitalized, intubated

7. Hospitalized, advanced life support including invasive mechanical ventilation or ECMO 8. Death 4a) Ordinal scale rates: proportion of treatment group versus placebo group, respectively who had experienced:

an improvement from scale 2 at randomization to scale 1 or 0 on days 4, 7, 10, 14, 21, 28, 42, 60 post randomization, an improvement from scale 1 at randomization to scale 0 on days 4, 7, 10, 14, 21, 28, 42, 60 post randomization a sustainment from scale 1 at randomization to scale 1 on days 4, 7, 10, 14, 21, 28, 42, 60 post randomization any improvement of the scale (i.e., at least a 1-point decrease) between enrollment and days 7, 14, 28, 42, 60 post randomization any worsening of the scale (i.e., at least a 1-point increase) between enrollment and days 7, 14, 28, 42, 60 post randomization scale 4 or higher by day 28 or day 60 post randomization scale 6 or higher by day 28 or day 60 post randomization 4b) Ordinal scale averages, highs, and lows: Comparison of treatment group versus placebo group, respectively, at days 14, 28 and 60 post randomization in the average of daily scale value on that day overall average of daily scale value experienced since enrollment in the worst (i.e., highest) daily scale value experienced since enrollment in the best (i.e., lowest) daily scale value experienced since enrollment 4c) Time to improvement: Comparison of treatment group versus placebo group, respectively, in the number of days from enrollment until first experiencing a 1-point improvement sustained over at least 2 days by day 14, day 28 and by day 60 post randomization 4d) Length of ordinal scale experience: Comparison of treatment group versus placebo group, respectively, in the total number of days by day 14, day 28 and by day 60 post randomization on which subjects experienced a given scale value (i.e., 3, 4, 5, 6, 7)

5. Surrogate Markers of COVID-19-Related Inflammation and Organ Involvement

5a) Analysis and comparison of surrogate markers of COVID-19 related inflammation and organ involvement as determined by biochemistry, hematology, and immunology labs and studies, in treatment group versus placebo group, respectively, for values on days 1, 7, 14, 21, 28 post randomization changes from enrollment to days 7, 14, 21, or 28 post randomization changes between days 7, 14, 21, 28 post randomization 5b) Reference range rates: proportion of treatment group versus placebo group, respectively, who experience normal/in-range values for a given marker at days 7, 14, 21, 28 post randomization Statistical Considerations Study Populations:

Safety & Tolerability Population: All enrolled subjects who have received at least 1 dose of IP (belnacasan or placebo) are studied. Even if subjects have discontinued study treatment, as long as they maintain consent, they continue to be in the study and included in analysis, i.e., their safety and tolerability information continues to be collected for at least 60 days.

Treatment Effect Evaluable Populations: All enrolled subjects who have received at least 1 dose of IP (belnacasan or placebo) are studied. Even if subjects have discontinued study treatment, as long as they maintain consent, they continue to be in the study and included in analysis, i.e., their outcome information continues to be collected for at least 60 days.

Analysis Methods:

FDA Data Standard Guidelines are followed. Continuous variables are summarized using the number of observations, number of observations above the limit of quantification (if applicable), mean, standard deviation (SD) median, and range. Categorical variables are summarized using frequency counts and percentages. Comparison of belnacasan and placebo groups utilize Poisson regression for counts, Cox proportional hazards regression for time-to-event data and mixed effects models for continuous and categorical data obtained over study days.

Primary Safety and Tolerability Analysis:

All safety & tolerability analyses are performed on the Safety Population. The safety data is presented in individual listings and summary tables. Overall safety is assessed by the number of belnacasan dosed subjects experiencing a grade 4 or 5 SAE during the trial. Of 24 subjects enrolled in the belnacasan group, 3 or more developing a grade 4 or 5 SAE potentially related to belnacasan would be considered unlikely due to chance. Therefore, belnacasan is determined safe if no more than 2 subjects develop a grade 4 or 5 SAE in the belnacasan group potentially related to belnacasan. If 3 or more subjects in the belnacasan group develop SAEs potentially related to belnacasan during the trial, belnacasan is considered not safe, and the trial stopped or placed on clinical hold as noted.

Secondary Treatment Effect Endpoint Analysis:

Event counts over 60 days are analyzed by Poisson regression. Time to events is analyzed by Cox regression. Differences between belnacasan and placebo with respect to change in continuous endpoints are assessed by mixed effects models for continuous repeated measures data and mixed effects logistic models for repeated categorical variables. Endpoint proportions of belnacasan and placebo groups are assessed by contingency table analysis (chi-square).

Sample Size Considerations:

As this is a proof-of-concept study, it is likely not be powered to detect belnacasan-placebo differences that are clinically meaningful. For example, the observed difference in endpoint rate ratios would need to be over 60% to achieve 80% power with an alpha error rate of 5% for 24 subjects in each group. This study provides an estimate of the belnacasan effect size to inform a larger trial where a more clinically meaningful difference can be detected.

Background and Study Rationale

For more than one year, coronavirus disease 2019 (COVID-19)—an acute respiratory disease caused by SARS-CoV-2 that also has profound multi-systemic inflammatory involvement—has cost countless lives and livelihoods, especially for vulnerable populations with comorbidities characterized by chronic inflammation. The full spectrum of COVID-19 ranges from asymptomatic, to a mild, self-limiting respiratory tract illness, to severe progressive pneumonia, multi-organ failure, and death [1]. Since its first discovery, the virus has continued to spread, even with attempted control with a variety of public health measures. There are more than 32 million cases in the United States, accounting for a quarter of the worlds documented cases, and over 570,000 deaths [2]. In general, there is likely an underestimate of total cases since the prevalence of asymptomatic carriers is yet unknown. What is clear, is that individuals at highest risk are those over 65 years and/or those with concomitant chronic conditions most notably hypertension, diabetes, pre-diabetes, obesity, chronic cardio-respiratory disorders and chronic renal and liver impairment [1, 3-6]. While there are racial disparities in the greater number of Black and Hispanic patients experiencing a more severe course there is no evidence that this is related to anything other than underlying comorbidities and socioeconomic factors, often limiting their ability to socially distance.

There have been promising scientific breakthroughs for preventing and treating severe COVID-19, including via vaccines, monoclonal antibody and steroid treatments. However, there is to-date no targeted treatment for SARS-CoV-2-mediated inflammation and subsequent complications in COVID-19. In general drug treatments aimed at the virus have so far not lived up to their promise. Most notably the nucleotide analog remdesivir was demonstrated to mitigate the course of the illness when given early in the course [7]. Subsequent data however failed to show a benefit. While antibody for treatment has been available the uptake of this therapy has been limited by parenteral administration. While efficacious in patients with mild to moderate COVID-19 who are at high risk of progressing to severe disease [8], monoclonal antibodies (e.g., bamlanivimab, casirivimab, and imdevimab) are costly and their administration is complicated for outpatients and providers as it is given intravenously, in an hour long infusion that must take place in a separate unit since recipients are infectious. A late 2020 report from the Department of Health and Human Services found that only 5-20% of available supply had been used. Currently the most widely accepted and available treatment is dexamethasone having shown a clear benefit in seriously affected, hospitalized patients [9].

The most hopeful remedy for the population at large is vaccination and at this time vaccines from three sources (Pfizer/BioNTech, Moderna, Johnson & Johnson) have been authorized for emergency use in the United States after having demonstrated the ability to prevent disease in up to 95% of individuals [10]. However, vaccines may not be sufficient to address COVID-19 across the US population for four reasons. First, vaccine hesitancy persists (https://aspe.hhs.gov/pdf-report/vaccine-hesitancy). Second, vaccination may only confer immunity for a limited number of months, necessitating the need for booster shots (https://www.cnbc.com/2021/04/21/scientist-who-helped-develop-pfizer-biontech-covid-vaccine-agrees-third-shot-is-needed-as-immunity-wanes.html), which may not be taken, or taken on time, by all who need them. Third, immunocompromised people, such as transplant recipients on immunosuppressive medication, have recently been shown to not develop sufficient antibodies through vaccination [11, 12]. Fourth, it remains to be seen to what extent vaccines are effective against emerging new variants with immune-escape properties [13-15].

Moreover, given that even mild COVID-19 cases can result in devastating, likely inflammatory-driven, persisting effects (https://www.cdc.gov/coronavirus/2019-ncov/long-term-effects.html), there is clearly an unmet need for a therapeutic option, especially an oral one, that can mitigate harmful uncontrolled inflammation and dysfunctional immune responses during a SARS-CoV-2 infection.

Fortunately, over the past year there has been better understanding of the immunologic pathophysiology of COVID-19, which in later stages is driven primarily by host immune responses to the virus [16]. In the spring of 2020, Applicants' team was the first to publish data linking the inflammasome/caspase-1/pyroptosis axis to heightened pro-inflammatory IL-18 levels, lymphopenia and poor outcome in COVID-19 patients [6]. Over the summer of 2020, a Brazilian study in over 100 patients expanded Applicants' findings, and also showed direct evidence of NLRP3 inflammasome activation and caspase-1 mediated pyroptosis in SARS-CoV-2-infected monocytes in vitro, as well as in blood and lung tissue of COVID-19 patients [17, 18]. Inflammasome formation, as evidenced by expression of caspase-1 and NLRP3 in leukocytes and endothelial cells, was also found in the lungs of patients with fatal COVID-19 pneumonia [19, 20]. Most recently, several studies further corroborated and expanded these findings by showing that SARS-CoV-2 infects monocytes and directly activates the inflammasome/caspase-1/pyroptosis axis leading to pro-inflammatory cell death and cytokine release [21, 22]. Importantly, it was further demonstrated that a caspase-1 specific inhibitor was effective in blocking pyroptotic cell death of SARS-CoV-2-infected monocytes and subsequent release of the pro-inflammatory cytokines IL-1B, IL-6, and TNF-α [21]. In addition, from a mechanistic standpoint, it was recently shown that SARS-CoV-2 viroporin encoded by ORF3a activates the NLRP3 inflammasome and caspase-1 via potassium efflux [23]. Moreover, key ORF3a amino acid residues required for inflammasome activation were found to be conserved in virus isolates across continents, highlighting the universality of this inflammatory pathway [23].

Taken together, a growing body of evidence demonstrates that upstream SARS-CoV-2-mediated inflammasome and caspase-1 activation leading to pyroptosis, trigger uncontrolled hyper-inflammation via cytokine release (IL-18, IL-1β, IL-6, and TNF-α) as well as immune dysfunction of monocytes and lymphocytes downstream [16, 24-28]. Moreover, activation of the inflammasome/caspase-1/pyroptosis axis could also explain COVID-19 related organ damage and tissue pathology of the heart, kidney, lungs, liver, pancreas and nervous systems, as it has been shown that SARS-CoV-2 also appears to cause pyroptosis in a variety of other cell types, including lung pneumocytes and endothelial cells in these organs [27-32].

Figure 4:
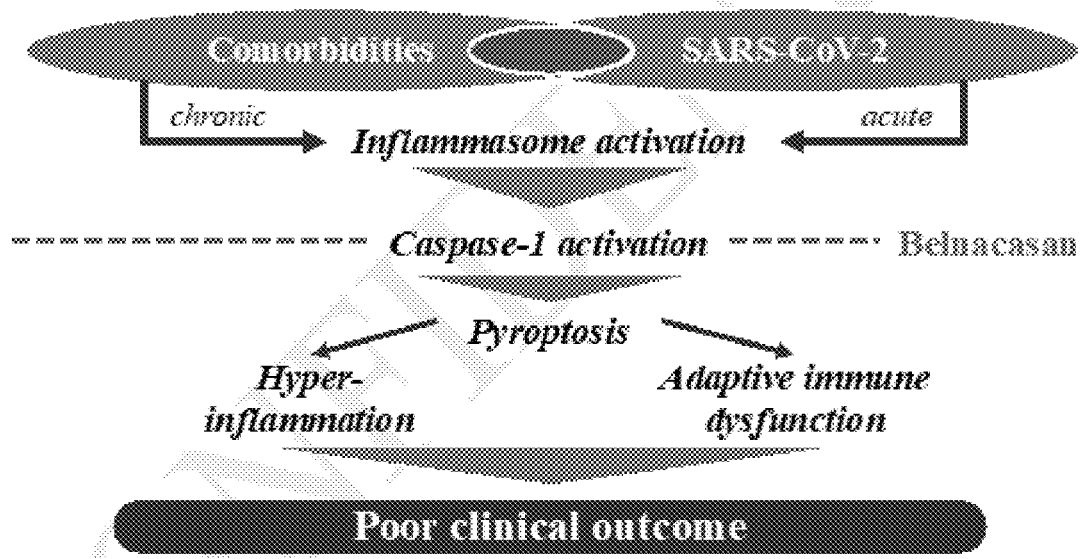
FIG. 4: The Inflammasome and COVID-19: Rational for belnacasan.

Based on this growing body of evidence, this trial proposes that the orally-administered belnacasan, which following hydrolysis on contact with water is a highly specific caspase-1 inhibitor (also known as IL-1β converting enzyme) upstream of pyroptosis and pro-inflammatory cytokine release, is a much more targeted and potentially safer alternative to current generalized anti-inflammatory COVID-19 treatments such as corticosteroids, especially for comorbid patients with an already chronically-activated inflammasome [6, 25, 27, 28, 33-36] (FIG. 4).

Belnacasan (VX-765/RVT-201/MSR-001)

The drug substance has a molecular formula of $C_{24}N_{33}ClN_4O_6$ and has molecular weight of 509.0 and comes as a tablet preparation. It is hydrolyzed on contact with water to an active form and is a caspase-1 inhibitor (caspase-1 is also known as IL-1β converting enzyme). Blocking this enzyme with belnacasan (VX-765/RVT-201/MSR-001) has been shown to prevent production of IL-1β, IL-18, and pyroptosis in healthy and disease states. The drug has been extensively developed originally by Vertex Pharma and more recently Roivant Sciences but currently has no FDA or IND approved usage for any indication.

Dosing Rationale

Belnacasan (VX-765/RVT-201/MSR-001) has previously been studied in rodents and large animals including dogs and monkeys to doses of up to 2000 mg/kg/day for toxicity studies in dogs. Dosing at these levels and in multi-dosing schedules have not shown any severe and particularly life-threatening side effects. In human trials, including for conditions such as seizure disorders, the drug has been trialed in increments of 300 mg/dose on a TID or QID regimen up to 900 mg QID for 13 weeks, in nearly 100 patients.

Detailed pharmacokinetic studies from Vertex/Roivant are available for review. In brief, ex-vivo studies have demonstrated that Lipopolysaccharide stimulated IL-1B production is 50% suppressed by the active metabolite of belnacasan at a concentration of 0.8 mcg/ml. This translated in to 50% suppression of IL-1B by single oral dose of 400 mg while 80% suppression was achieved with doses of 800 and 1600 mg. There was gradual but marked inhibition of IL-18 over 14 days in healthy controls as compared to placebo and 60% inhibition with 900 mg TID as well as 1200 mg TID and 1800 mg TID during the duration of the study. For this study Applicants have therefore chosen Applicants' primary dose as 900 mg TID in the absence of data on acute viral infection/COVID-19.

The drug has previously been manufactured with appropriate due diligence in tablet form at 300 mg/tablet (Data available from Roivant Sciences) and is manufactured by the same compounding pharmacy (Metrics), in the original format for immediate use in this trial.

For this trial Applicants treat for a maximum of 28 days. Applicants' rationale for this timeframe is that while there is an expectation that the illness lasts up to 12-15 days in those who recover without complication, others endure a longer duration, and some experience persistent, new onset or worsening disease related symptoms. A recent study from the Centers for Disease Control and Prevention (https://www.cdc.gov/mmwr/volumes/70/wr/mm7017e3.htm?s_cid=mm7017e3_w) found that among 3,171 non-hospitalized adult COVID-19 patients, 69% had one or more outpatient visits 28-180 days after the diagnosis. Two thirds had a visit for a new primary diagnosis, and approximately one third had a new specialist visit. Symptoms potentially related to COVID-19 were common new visit diagnoses. Visits for these symptoms decreased after 60 days but for some patients continued through 120-180 day. Furthermore, some individuals develop sequela that are likely related to post-viral immune dysregulation in the first few months albeit there is little known about this group. Though Applicants are unlikely to learn about the effect of the drug in this latter population Applicants do need to establish safety for a duration that includes the other groups mentioned above.

Brief Summary of Known Systemic Safety Profile of Belnacasan (VX-765/RVT-201/MSR-001)

Based on files held by Vertex and Roivant Sciences, which contains evidence from animal and human studies, there is no indication that belnacasan (VX-765/RVT-201/MSR-001) causes severe or life-threatening side effects. The only preclinical finding on toxicity studies was a reduction of the heart rate in dogs at 2000 mg/kg/day, a dose that was estimated to be 10-25 times higher than the maximum in this study (900 mg QID). In humans with epilepsy the drug has been used at dosages of 3600 mg/day for up to 13 weeks. Adverse effects reported in humans were headache, dizziness, nausea and vomiting, abdominal discomfort and rash. Seizure was reported in more than one patient in one study on epilepsy.

In modern history there is been no greater health threat to life and livelihood than COVID-19, especially in the United States. While progress is being made to find treatments, there are potential drawbacks to all options. First, even with the prospect of vaccines being successful, there is a likelihood that patients with co-morbid conditions suffer a protracted illness at least; that it takes time for the vaccine and any needed boosters to reach critical mass in the population, especially in the face of vaccine hesitancy; and that vaccines might not always be effective, especially as new virus strands and variants continue to emerge and early data show that immunosuppressed patients may struggle to develop anti-bodies. Second, while the most frequently heralded therapeutic of remdesivir offers the potential for earlier clearance of the virus, the inflammatory cascade results in continued need for inpatient and especially intensive care in high-risk patients. Furthermore, as an IV drug, the treatment itself requires inpatient treatment and likely needs specific timing to be optimally effective. Third, the prospect of immunosuppression, for example with a broad therapy such as dexamethasone or other equivalent corticosteroid, affects the inflammatory cascade but any use beyond a few days carries risks and therefore disadvantages that Applicants believe come to light with greater use of the drug and scrutiny of outcomes going forward. Over the next 12 months it is reasonable to expect that a large part of the United States population undergoes vaccination with the majority of these individuals being afforded some immunity for what is yet an undetermined length of time. What is clear however is that this form of coronavirus is likely to be around for the foreseeable future and though fewer people are at risk for COVID-19, an effective treatment is necessary. While antiviral treatment may have an effect, it is clear from the pathophysiology that clearing virus may not be enough and such specific therapies to mitigate the individual's inflammatory response is important to reduce morbidity and mortality. Applicants believe that what is needed is an immunologically targeted medication that can be taken orally—and without the prospect of major immunosuppression in at-risk patients—and that can even be taken for early treatment in high-risk patients. Based on the data presented here Applicants believe that belnacasan (VX-765/RVT-201/MSR-001) fulfils this role.

Primary Objective

To determine the safety and tolerability of belnacasan (VX-765/RVT-201/MSR-001) administered orally for 28 days in subjects with mild to moderate COVID-19 as determined by Adverse Events and Serious Adverse Events.

Primary Endpoint

Incidence of Adverse Events and Serious Adverse Events assessed out to day 60.

Secondary Objective

To generate data on the treatment effect of belnacasan (VX-765/RVT-201/MSR-001) administered orally for 28 days in subjects with mild to moderate COVID-19 as determined by its effect size on outcomes in five areas:

Clinical recovery and resolution of COVID-19 symptoms
Physical functions and parameters relevant to COVID-19
COVID-19 related deterioration and mortality
WHO 9-point ordinal scale for clinical improvement
Surrogate markers of COVID-19-related inflammation and organ involvement The hypothesized end result of treatment with belnacasan would be to reduce the symptomatic and clinical burden, length of disease course, and disease progression of COVID-19.

Secondary Endpoints

1. Clinical Recovery and Resolution of COVID-19 Symptoms

1a. Sustained recovery and resolution rates of common COVID-19 symptoms:

(i.e., stuffy or runny nose, sore throat, cough, low energy or tiredness, muscle or body ache, headache, chills or shivering, feeling hot or feverish, nausea, vomiting, diarrhea, shortness of breath with exertion; impairment in sense of smell or taste)

Proportion of subjects in treatment group versus placebo group, respectively, who per symptom questionnaire on days 4, 7, 10, 14, 21, 28, 42, 60 post randomization have achieved for two consecutive days:

scores not higher than 0 for all symptoms scores not higher than 1 for all symptoms scores not higher than 0 for all symptoms other than impairment of taste or smell scores not higher than 1 for all symptoms other than impairment of taste or smell 1b. Sustained improvement of global impression rates: Proportion of subjects in treatment group versus placebo group, respectively, who per symptom questionnaire on days 4, 7, 10, 14, 21, 28, 42, 60 post randomization have answered for two consecutive days "Yes" to "In the past 24 hours, have you returned to your usual health (before your COVID-19 illness)?"

"Yes" to "In the past 24 hours, have you returned to your usual activities (before your COVID-19 illness)?"

"None" to "In the past 24 hours, what was the severity of your overall COVID-19 related symptoms at their worst?"

"Mild" to "In the past 24 hours, what was the severity of your overall COVID-19 related symptoms at their worst?"

1c. Time to sustained recovery, resolution or improvement: comparison in treatment group versus placebo group, respectively of the number of days from randomization to the first day of achieving each item in 1a and 1b above.

2. Physical Functions and Parameters Relevant to COVID-19

2a. Parameter rates: Proportion of subjects in treatment group versus placebo group, respectively, who on days 4, 7, 10, 14, 21, 28, 42, 60 post randomization per thermometer or pulse oximeter reading experienced:

fever at any point between enrollment and day 2 post randomization and who were afebrile <38C oxygenation of SpO2>=96% or >93% in room air when resting 2b. Time to and length of parameters: comparison in treatment group versus placebo group, respectively of the number of days from randomization to the first day of achieving sustained (i.e., at least 2 days) resolution of fever for subjects who presented with fever at any point between enrollment and day 2 post randomization with temperature <38C or >=38C experienced in total during the first 28 days post randomization from randomization to the first day post randomization of achieving oxygenation of SpO2>=96% in room air when resting for subjects who presented with SpO2>93% and <96% in room air, when resting, at enrollment with oxygenation of SpO2>=96% or SpO2>93% in room air, when resting, in total during the first 28 days post randomization 3. COVID-19 Related Deterioration and Mortality 3a. Deterioration and mortality rates: Proportion of treatment group, versus placebo group, respectively, who per subject reporting or medical records by day 14, day 28 and by day 60 post randomization had experienced:

an emergency department visit, other than at study enrollment or study visits hospitalization for COVID-19 hospitalization for COVID-19 requiring oxygen hospitalization for COVID-19 requiring ICU hospitalization for COVID-19 requiring ventilation COVID-19 related death death hospitalization or death 3b. Time to and length of deterioration: Comparison of treatment group versus placebo group, respectively, in the number of days from randomization until the first day of experiencing hospitalization for COVID-19 of hospitalization for COVID-19 experienced in total by day 14, by day 28 and by day 60 post randomization of hospitalization for COVID-19 requiring oxygen experienced in total by day 14, by day 28 and by day 60 post randomization of hospitalization for COVID-19 requiring ICU experienced in total by day 14, by day 28 and by day 60 post randomization of hospitalization for COVID-19 requiring ventilation experienced in total by day 14, by day 28 and by day 60 post randomization 4. WHO 9-Point Ordinal Scale 0. Uninfected or "no clinical or virological evidence of infection"

defined as subject answering "Yes" to "In the past 24 hours, have you returned to your usual health (before your COVID-19 illness)?"

1. Not hospitalized, no limitations on activities defined as subject answering "Yes" to "In the past 24 hours, have you returned to your usual activities (before your COVID-19 illness)?"

2. Not hospitalized, limitation on activities defined as subject answering "No" to "In the past 24 hours, have you returned to your usual activities (before your COVID-19 illness)?"

3. Hospitalized, not requiring supplemental oxygen

4. Hospitalized, requiring supplemental oxygen

5. Hospitalized, on non-invasive ventilation or high flow oxygen devices

6. Hospitalized, intubated

7. Hospitalized, advanced life support including invasive mechanical ventilation or ECMO 8. Death 4a) Ordinal scale rates: proportion of treatment group versus placebo group, respectively who had experienced:

an improvement from scale 2 at randomization to scale 1 or 0 on days 4, 7, 10, 14, 21, 28, 42, 60 post randomization, an improvement from scale 1 at randomization to scale 0 on days 4, 7, 10, 14, 21, 28, 42, 60 post randomization a sustainment from scale 1 at randomization to scale 1 on days 4, 7, 10, 14, 21, 28, 42, 60 post randomization any improvement of the scale (i.e., at least a 1-point decrease) between enrollment and days 7, 14, 28, 42, 60 post randomization any worsening of the scale (i.e., at least a 1-point increase) between enrollment and days 7, 14, 28, 42, 60 post randomization scale 4 or higher by day 28 or day 60 post randomization scale 6 or higher by day 28 or day 60 post randomization 4b) Ordinal scale averages, highs, and lows: Comparison of treatment group versus placebo group, respectively, at days 14, 28 and 60 post randomization in the average of daily scale value on that day overall average of daily scale value experienced since enrollment in the worst (i.e., highest) daily scale value experienced since enrollment in the best (i.e., lowest) daily scale value experienced since enrollment 4c) Time to improvement: Comparison of treatment group versus placebo group, respectively, in the number of days from enrollment until first experiencing a 1-point improvement sustained over at least 2 days by day 14, day 28 and by day 60 post randomization 4d) Length of ordinal scale experience: Comparison of treatment group versus placebo group, respectively, in the total number of days by day 14, day 28 and by day 60 post randomization on which subjects experienced a given scale value (i.e., 3, 4, 5, 6, 7)

5. Surrogate markers of COVID-19-related inflammation and organ involvement

Heart: troponin; Kidney: creatinine, blood urea nitrogen (BUN), electrolytes (calcium, carbon dioxide, chloride, potassium, sodium, magnesium); Pancreas: glucose, HbA1c, lipase; Liver: ALT, AST, ALP, total bilirubin; Muscle weakness: creatinine kinase; Hematology: red blood cell count, hemoglobin, platelet count, prothrombin time (PT), partial thromboplastin time (PTT), d-dimer; Immunology: white blood cell count, neutrophils, lymphocytes, monocytes, eosinophils, T cells, SARS-CoV-2 viral load in nasopharyngeal sample, SARS-CoV-2 serology in blood; Inflammation: CRP, ferritin, LDH, caspase-1, IL-18, IL-1β, IL-1 receptor antagonist, gasdermin D, IL-6, TNF-α, G-CSF 5a) Analysis and comparison of surrogate markers of COVID-19 related inflammation and organ involvement as determined by biochemistry, hematology, and immunology labs and studies, in treatment group versus placebo group, respectively, for values on days 1, 7, 14, 21, 28 post randomization
changes from enrollment to days 7, 14, 21, or 28 post randomization
changes between days 7, 14, 21, 28 post randomization 5b) Reference range rates: proportion of treatment group versus placebo group, respectively, who experience normal/in-range values for a given marker at days 7, 14, 21, 28 post randomization The drug in an oral form has been used in nearly one hundred patients without a history of major side effects. During the trial, it is therefore anticipated that no more than 2 subjects out of 24 have an adverse event of grade 4 or 5 that is at least possibly related to belnacasan (VX-765/RVT-201/MSR-001). Should there be 3 or more subjects with an adverse event grade 4 or 5 that is at least possibly related to belnacasan (VX-765/RVT-201/MSR-001) in subjects receiving the IP, the study is put on an immediate clinical hold. Safety Monitoring processes are identified in Section 7.14.

In addition, individual safety stopping rules include having a non-DLT respiratory adverse event >grade 3 during study medication administration that is at least possibly attributable to belnacasan (VX-765/RVT-201/MSR-001).

Study Description

This is a phase 2 proof of concept randomized, double-blind, placebo-controlled trial with the purpose of assessing the safety, tolerability and treatment effect of the orally administered Caspase-1 inhibitor, belnacasan, for the treatment of patients with mild to moderate COVID-19. 24 subjects are given 900 mg TID of belnacasan and 24 subjects are given a placebo TID for 28 days, and assessments of safety, tolerability, and treatment effect are performed for up to 60 days.

At the screening/baseline/day 1 Visit, subjects provide informed consent and be screened for eligibility based on the Inclusion/Exclusion criteria Subjects also receive the first dose of study drug at this visit once study eligibility has been confirmed, and the second dose of study drug is taken approximately 8-12 hours after the first dose. Study drug is continued three times daily (morning, mid-day, and nighttime doses) through day 28.

The trial duration is approximately 60 days (8.5 weeks) for all subjects enrolled. As outlined in the Schedule of Events Table in Section 5.2, over the course of the study duration, all subjects use a diary to record IP intake as well as symptoms and activity levels with guidance to do so at the same time each day; assess physical parameters using a study-provided thermometer and pulse oximeter; be assessed at regular intervals via telemedical and in-person follow-up clinic visits; and give blood for laboratory tests.

Subjects are instructed to complete the diary at the same time each day, at a time that is consistently convenient for them. The Study Team conduct in-person visits with the subjects on days 7, 14, 21, and 28 and telephonic visits with subjects on days 1, 4, 10, 42, and 60. The Telemetry Care Team conducts telephonic visits daily through day 28. Subjects receive reminders to complete the diary via text message and/or email. Subjects who prematurely discontinue study drug for any reason are asked to have an Early Termination (ET) visit the day the last study drug dose is administered; moreover, they are encouraged to stay enrolled so that further safety and outcome information can be collected and analyzed.

All data collected by the Study Team and Telemetry Care Team is entered into the EDC daily, for this trial OnCore is used. OnCore is a Clinical Trial Management System in which subject visits can be monitored as well as Case Report Forms developed. Subjects are asked to hand in their subject diary during visits on days 7, 14, 21, and 28.

Background Standard of Care

All eligible subjects receive background standard of care, however there are certain prohibited medications subjects cannot be given while dosed with the IP as outlined in Exclusion Criteria. Background standard of care are commensurate with disease severity and aligned to standards at the time of the trial. At present, standard of care includes antiviral treatment with remdesivir, monoclonal antibodies against SARS-CoV-2, dexamethasone, supplemental oxygen, noninvasive and invasive ventilation, antibiotics, vasopressors and ECMO; but this may evolve over the coming months as new therapies or treatments come online.

Patients recruited to the study are not be asked to forgo background standard of care in any way. Recruitment is based on inclusion and exclusion criteria and include only individuals evaluated in an emergency room from designated institutions and triaged not to need in-hospital care. These individuals have the potential but not the likelihood for hospital admission with worsening COVID-19 disease progression. Current outpatient standard of care includes symptomatic treatment and this is not be altered to the point that analgesics and antipyretics are held. Patients whose COVID-19 related illness deteriorates to the point that they need ambulatory medical care or hospitalization remain in the study and medical care as determined by managing physicians are not subverted in any manner as part of the study. Patient data collection as per study diary and study visits are maintained for the minimum 60 days and study drug is provided and monitored for compliance unless there is an indication for discontinuation of study drug, see section on drug discontinuation.

Study Population

Emergency Department or Critical Care presenting subjects, who are not under immediate consideration for inpatient admission and with onset of at least one moderate COVID-19 symptom of less than 7 days, is assessed for eligibility on the basis of a positive reverse transcriptase polymerase chain reaction (RT-PCR) assay for SARS-CoV-2 in a respiratory tract sample on presentation to the hospital.

Enrollment of Diverse Study Population

Recognizing that COVID-19 disproportionately impacts racial and ethnic minorities, the study seeks to enroll a diverse patient population. The envisioned trial site, MedStar Washington Hospital Center, is the largest hospital in the District of Columbia. Its primary service area includes 11 zip codes, most of which are the zip codes that make up Wards 5, 7, and 8. Minorities represent 58% of the population in DC overall, and 69%, 97%, and 96% of the population in Wards 5, 7, and 8, respectively. Three Metrobuses service the campus and MedStar provides free, wheelchair-accessible shuttle buses from two Metrorail stations. Moreover, subjects receive financial support for travel to and from study visits.

Number of Subjects

Approximately 48 subjects are recruited at WHC or other MedStar hospital and/or critical/clinical care sites.

Selection Criteria

Inclusion Criteria:

Subject (or legally authorized representative) provides written informed consent prior to the initiation of any study procedures.

Subject understands and agrees to comply with planned study procedures, including using the diary.

Subject agrees to the collection of nasopharyngeal swabs and venous blood per protocol.

Subject is male or non-pregnant female adult ≥18 years of age at time of consent.

Women with a history of menstruation must agree to use two methods of contraception, at least one of which is highly effective, for the duration of the study as well as to undergo additional pregnancy testing during the study.

Subject has a laboratory confirmed SARS-CoV-2 infection as determined by RT-PCR assay prior to enrollment.

Subject has evidence of either mild or moderate COVID-19 illness of less than 7 days from first onset, with minimal baseline symptom severity based on patient-reported FDA scoring system defined as follows:

Subject presents with at least two common symptoms of COVID-19 from the following list: stuffy or runny nose, sore throat, cough, low energy or tiredness, muscle or body ache, headache, chills or shivering, feeling hot or feverish, nausea, vomiting, diarrhea, shortness of breath with exertion (without supplemental oxygen requirement) with a score of 2 or higher; impairment in sense of smell or taste with a score of 1 or higher OR Subject presents with any (i.e., at least one) symptom of COVID-19 as defined above AND clinical evidence of moderate COVID-19 as defined by FDA guidance for industry (such as respiratory rate >20 breaths per minute, heart rate >90 beats per minute, with oxygen saturation >93% on room air at sea level).

Subject presents with high-risk for COVID-19-related inflammation determined by at least one comorbidity, including obesity, diabetes, hypertension, stable heart disease, respiratory disease, or non-severe fatty liver disease and/or age >60 years.

Subject's overall health condition is deemed as suitable to fully and safely participate in this trial as determined by the Investigator.

Exclusion Criteria:

Any clinical signs indicative of severe or critical COVID-19 as defined by FDA guidance for Industry at the time, including SpO2<93% and/or oxygen requirement.

Hospitalization for COVID-19, or consideration thereof

ICU level of care and/or non-mechanical/mechanical ventilation and/or oxygen supplementation at time of enrollment.

Pregnant or breast-feeding subjects.

Subjects who cannot swallow tablets.

History of any pre-existing organ impairment, such as:

Severe kidney disease (known or estimated GFR <30 mL/minute) or on dialysis.

Uncontrolled, clinically significant heart diseases such as arrhythmias, angina or heart failure as defined by AHA/ACC Grade C and D.

Chronic respiratory disease requiring supplemental oxygen.

Moderate and severe hepatic impairment as defined by Child-Pugh scoring Class B and Class C Elevated liver function tests (determined by ALT, AST, GGT, or ALP >2× upper limit of normal, and total Bilirubin >upper limit of normal).

History of malignancy or immunodeficiency within the prior 5 years.

Acute respiratory illness other than COVID-19.

Active bacterial, viral or fungal infection (including HIV, hepatitis B, hepatitis C).

While dosed with the IP, the taking of prohibited concomitant medication or the ingestion of food that interferes with the IP, including:

Non-COVID19-related anti-viral medication such as lopinavir, ritonavir, ribavirin or interferon-1β.

Systemically administered immunosuppressive and anti-inflammatory agents, other than background standard of care for COVID-19 at the time.

Drugs and foods that are potent inhibitors or inducers of CYP3A4 and/or P-gp, as listed in FDA "Drug Development and Drug Interactions: Table of Substrates, Inhibitors and Inducers", including herbal medications such as St. John's Wort within 30 days or 5 half-lives (whichever is longer) prior to the first dose of study drug.

Any other diseases or medical conditions or concomitant medications that are deemed as not compatible or appropriate for the subject's ability to fully and safely participate in this trial as determined by the Investigator.

Discontinuation Criteria and Early Termination Procedures

Subjects may withdraw voluntarily from participation in the study at any time and for any reason. Subjects may also be withdrawn on the basis of the Investigator's clinical judgment. This study may be terminated at the discretion of MedStar Health or of any regulatory agency for reasons including safety and/or treatment effect.

For enrolled subjects Applicants anticipate that the main reasons for discontinuation of therapy is either withdrawal of consent for continuation in the study or inability to tolerate the study. Other instances may include patient death, inability to take the study drug from severity of illness or in-hospital complexity of illness. Subjective intolerance of the drug from minor side effects or alternatively cessation of COVID-19 related symptoms well ahead of the 28-day schedule may cause patients to want to discontinue the drug. With regards to drug toxicity itself, Applicants anticipate minor symptomatology from adverse effects, such as headache, dizziness, nausea and vomiting, abdominal discomfort and rash (see also 1.4) based on prior human trial experience with the study drug. Should any subject dosed on the study drug experience seizures, which was reported as an unrelated adverse event in an epilepsy trial, that individual would be subject to discontinuation out of an abundance of caution.

Any emergent symptom that has no clear cause results in a hold on subsequent study drug dosing until protocol assessment by the Study Investigator. The reasons for discontinuation of study drug are documented clearly. In all cases study protocol monitoring continues for the entire 60 days of the protocol as long as the subject stays consented.

When a subject withdraws or is withdrawn before completing the study, the date and reason for withdrawal are to be documented. Subjects who withdraw or who are withdrawn prematurely are to attend an early termination, at which time they complete all assessments as outlined in the Schedule of Events (Table 1); moreover they are encouraged to stay enrolled so that further safety and outcome information can be collected and analyzed.

In the event that a subject is withdrawn prematurely due to an adverse event or serious adverse event, the adverse event or serious adverse event is followed until it resolves or stabilizes, or until it is judged by the Investigator to be no longer clinically significant.

Concomitant and Prohibited Medication

At time of enrollment, and at any point during the study, medication or the ingestion of food that interferes with the IP would preclude participation in the study, including:

Non-COVID19-related anti-viral medication such as lopinavir, ritonavir, ribavirin or interferon-1β.

Systemically administered immunosuppressive and anti-inflammatory agents, other than background standard of care for COVID-19 at the time.

In vitro studies suggest that CYP-mediated metabolism is not a major route of clearance for belnacasan (VX-765/RVT-201/MSR-001) or VRT-043198. However, belnacasan (VX-765/RVT-201/MSR-001) was metabolized by CYP3A4 in a recombinant enzyme system.

Drugs and foods that are potent inhibitors or inducers of CYP3A4 and/or P-gp, as listed in FDA "Drug Development and Drug Interactions: Table of Substrates, Inhibitors and Inducers", including herbal medications such as St. John's Wort within 30 days or 5 half-lives (whichever is longer) prior to the first dose of study drug Subjects should also be advised against the consumption of grapefruit juice since it is a known inhibitor of CYP3A.

Study Drugs

All study medication is managed by the MedStar Health Research Pharmacy (RP). The Pharmacy stores and dispenses medication to subjects.

For all enrolled subjects, the first dose is given orally on day 1 as soon as the subject qualifies and signs the informed consent document. Subjects are closely monitored for at least 30 minutes to assure they do not experience any untoward effect.

For outpatient subjects (and discharged former inpatient subjects), subjects are instructed to take subsequent doses at 0600, 1400, 2200 (+/−4 hours). They self-record administration in a subject diary (see Appendix) to be reviewed by the study team who assesses compliance at each visit. The study team, under direction of the Investigator, provides any needed medication education, including adequate storage requirements, with the subject and any relevant family member(s) or caretaker.

For subjects who become inpatients over the course of the trial, study medication is supplied to the unit in which subjects are admitted and is dosed by clinical nursing, recorded in the electronic medical record, and overseen by the study team. Doses are given at 0600, 1400, 2200 (+/−4 hours). Those who cannot swallow tablets receive crushed tablets suspended in water and immediately administered through a nasogastric tube, by hospital nursing staff. At discharge and subsequent outpatient visits, enough medication is dispensed to the subject to assure they have adequate supply until their next on-site follow-up visit.

Storage, Dispensing and Reconciliation of Study Drug and Identity of Investigational Products All study medication is stored at room temperature until dispensed. Storage within the RP is locked and secure, accessible only to investigational pharmacy staff. Storage condition temperatures are recorded 24 hours a day, 7 days a week, and 365 days per year and the RP is immediately made aware of any temperature excursions. In such an event, study medication is not utilized until MedStar Health provides further direction. It is the Investigator's responsibility to ensure that accurate records of study medication dispensation and administration are maintained. The RP supports the Investigator in medication accountability and dispensation tracking, they have a clear process for return and destruction of investigational medications.

TABLE

Identification of Investigation Product

| | |
|---|---|
| Product Name | Belnacasan (VX-765/RVT-201/MSR-001) |
| Dosage form | Tablet containing 300 mg of API |
| Route/dosage | Oral |
| Dosing Instructions | Three tablets, three times per day (0600, 1400, 2200 +/− 4 hours) |
| Product Name | Placebo |
| Dosage form | Tablet containing 0 mg of API |
| Route/dosage | Oral |
| Dosing Instructions | Three tablets, three times per day (0600, 1400, 2200 +/− 4 hours) |

Observations and Measurements

Subject informed consent must be obtained prior to conducting any study-specific procedures. The informed consent can be signed by the subjects' legally authorized representative (LAR) if necessary. The Investigator assures that each subject/LAR is adequately consented to the requirements of participation including the potential risks and benefits and voluntary nature of the trial that he or she is free to discontinue participating in the study at any time. The subject/LAR is given the opportunity to ask questions and allowed adequate time to consider the information provided. All assessments and procedures are completed according to the Schedule of Events. A custom subject diary has been developed for this study. The diary is tested for basic comprehensibility before finalizing and using with subjects.

Instructions to Subjects

At enrollment, the Study Team explains the subject diary (see Appendix) and ensure they understand what to enter in each field. They are told of the importance of collecting the information in the diary for scientific purposes, and that even if they discontinue intake of the study drug, they should continue to participate in the study, continue to fill in the diary, and continue to attend planned study visits.

For outpatient subjects (and discharged former inpatient subjects), subjects are instructed to take 3 tablets of IP at 0600, 1400, 2200 (+/−4 hours) for up to 28 days. They self-record administration of the IP in the subject diary to be reviewed by the study team who assesses compliance at each visit. The study team, under direction of the Investigator, provide any needed medication education, including adequate storage requirements, with the subject and any relevant family member(s) or caretaker.

For subjects who become inpatients over the course of the trial, study medication are supplied to the unit in which subjects are admitted and are dosed by clinical nursing, recorded in the electronic medical record, and overseen by the study team. Doses are given at 0600, 1400, 2200 (+/−4 hours). Those who cannot swallow tablets receive crushed tablets suspended in water and immediately administered through a nasogastric tube, by hospital nursing staff. As study medication is administered by hospital staff, and there are no specific instructions to subjects. At discharge and subsequent outpatient visits, enough medication is dispensed to the subject to assure they have adequate supply until their next on-site follow-up visit.

Women with a history of menstruation must agree to use effective method of contraception and protections that align with International Council on Harmonization M3 R2 guidelines for highly effective methods of contraception for the duration of the study (i.e., two forms of contraception, whereby one result in a less than 1 percent per year failure rate when used consistently and correctly), as well as to undergo additional pregnancy testing during the study on day 14. Details of all pregnancies in female participants are collected for 60 days after randomization.

Warnings and Precautions

Subjects are watched carefully for signs of previously documented symptoms in human patients that have received belnacasan (VX-765/RVT-201/MSR-001), as well as symptoms to indicate a drug reaction or new symptoms that could be temporally attributable to the drug. The most frequent adverse effects in humans have been mild and mainly include headache, nausea, lethargy and dizziness. No serious side effects have been described in human and animal studies.

NCI CTCAE Definitions of Dose Limiting Adverse Events

The National Cancer Institute (NCI), Common Terminology Criteria for Adverse Events (CTCAE) are used for monitoring adverse events throughout study including those related to dose limitation. As noted above, adverse events with belnacasan (VX-765/RVT-201/MSR-001) have been mild and of no consequence (grade 1 and 2 by CTCAE criteria). There is no dose escalation in this trial that could result in new symptoms though it is possible that mild symptoms may become more severe.

Pre-Existing Medical Conditions

All subjects enrolled in the study have SARS-CoV-2 infection and at least two moderate COVID-19 symptoms or one moderate symptom and clinical evidence of moderate COVID-19. Subjects present with high-risk for COVID-19-related inflammation, due to at least one comorbidity, including obesity, diabetes, hypertension, stable heart disease, respiratory disease, or non-severe fatty liver disease and/or age >60 years.

Acute Conditions Brought on by COVID-19.

The development of acute kidney and/or hepatic injury has been reported as a possible complication during the disease progression of COVID-19. Acute kidney and/or hepatic injury are addressed in the following manner depending on whether at, (1) enrollment, (2) during the study period when drug is being administered in an ambulatory setting, (3) or during admission to hospital for COVID-19 related deterioration or other illness.

Potential participants in this study undergoes initial evaluation in the emergency room that includes background laboratory testing. If the testing indicates renal failure, GFR <30 or features of acute renal failure, most notably anuria, edema on examination in a previously healthy individual, the potential participant are not be enrolled as per the inclusion criteria or otherwise clarified with the nephrology consultant managing the patient. Similarly, potential participants shown to have evidence of elevated liver function tests (determined by ALT, AST, GGT, or ALP >2× upper limit of normal, and total Bilirubin >upper limit of normal) is not be enrolled in the study.

Laboratory testing throughout the study period may, though unlikely, show an acute change in renal or liver testing to indicate acute organ-specific disease or involvement as a possible complication of COVID-19. In such a circumstance, subjects are directed to seek care from the respective hospital/specialist. In the case of acute liver injury with functional impairment, the IP is discontinued immediately after blood has been taken for future assessment of drug levels. In the case of subjects with elevated liver function tests suggestive of acute liver injury without functional impairment, IP is held to discern in the first instance the possibility of an adverse event and restarted in consultation with the managing hepatologist if it is determined to be COVID-19 related hepatopathy. In the case of subjects with acute renal injury, IP is held to discern in the first instance the possibility of an adverse event and restarted in consultation with the managing nephrologist if it is determined to be COVID-19 related nephropathy. DSMB guidelines for unblinding is followed in these cases as relevant.

Acute liver and kidney injury may be seen in the face of hospital admission in patients with worsening COVID-19, in which case the patients are managed similarly to number 2 above (also see discontinuation).

Treatment Emergent Adverse Events

A treatment-emergent adverse event (TEAE) is defined as any event not present prior to the initiation of the treatments or any event already present that worsens in either intensity or frequency following the start of IP administration.

Adverse events are captured following the first dose of IP and could be related or unrelated to the study drug. A TEAE is defined as any AE that occurs after the subject takes the first dose of IP.

Separate summaries for adverse events that occur during treatment (summary of treatment emergent adverse events) are provided.

Laboratory Abnormalities

Clinical labs are performed locally at WHC or other MedStar clinical sites. Labs to be drawn during the study include serum chemistries, a hematology panel and an immune panel. A serum pregnancy test must be performed, and the result must be negative prior to the entry of women of child-bearing potential.

Clinical laboratory reports must be reviewed by a physician for out-of-range values within 12 hours of receipt. Out-of-range values are evaluated using the following notations:

NCS: Not clinically significant

LE: Laboratory Error

PT: Subject abnormal; relates to the subject's usual state of health

CS: Clinically Significant. This value cannot be explained by any of the other indicators.

By definition a lab value flagged as "CS" indicates an adverse event and are captured on the CRF. A laboratory test flagged "CS" should be repeated as soon as possible, then the Investigator should use his or her judgment as to whether the abnormal finding is sufficient reason to immediately withdraw the subject from the study.

If a laboratory value is considered to be serious and life-threatening and at least possibly related to the study drug, the subject should be immediately discontinued from the study and appropriate therapy started.

Adverse Event Assessment and Recording

All adverse events, exacerbations of concomitant illnesses, or events known to be related to underlying disease processes or concomitant medications are to be recorded on the CRF throughout the study. If a pre-existing condition worsens during the study, the date on which the exacerbation began should be recorded. Onset dates for study treatment-related adverse events must be on or after the date of initial study treatment use.

Adverse event recording includes the date of onset, severity, duration, whether or not the study medication was discontinued because of the event, the treatment given, and the outcome. The Investigator must also assess whether the event was related to the study medication, concurrent drug therapy, underlying disease, a combination of these factors, or if it is unknown. Subjects experiencing an adverse event should be carefully followed to determine outcome.

The Investigator use the NCI-CTCAE for adverse event monitoring, version 5.0 is applied in all instances. CTCAE version 4.03 may also be used especially when assessing laboratory tests given the complexity in applying version 5.0 in all instances, see www.lexjansen.com/phuse-us/2020/dh/DH16.pdf Definitions to grade the severity of the event:

Grade 1: Mild; asymptomatic or mild symptoms; clinical or diagnostic observations only; intervention not indicated.

Grade 2: Moderate; minimal, local, or non-invasive intervention indicated; limiting age-appropriate ADL.

Grade 3: Severe or medically significant but not immediately life-threatening; hospitalization or prolongation of hospitalization indicated; disabling; limiting self-care ADL.

Grade 4: Life-threatening consequences; urgent intervention indicated.

Grade 5: Death.

The relationship or association of the study medication in causing or contributing to the adverse event is characterized as not related, remote, possible, probable, or definite as defined below:

Not related: Evidence indicates no plausible direct relationship to the study medication Remote: Suggests other conditions are reasonably likely to account for the event including concurrent illness, progression or expression of the disease state, or reaction to concurrent medication Possible: Suggests that the association of the event with the study medication is unknown; however, the adverse event is not reasonably supported by other conditions Probable: Suggests that a reasonable temporal sequence of the event with medication administration exists and based upon the Investigator's clinical experience, the association of the event with study medication seems likely Definite: Suggests that based upon the Investigator's experience, the association of the event with the study medication seems very certain.

Planned procedures such as surgery should not be recorded as adverse events. However, the medical condition for which the procedure was performed should be reported if it meets the definition of adverse event.

Reporting Requirements

Any adverse event, defined below, that begins any time between the start of the first dose and within 28 days after the end of the last dose are to be recorded on the appropriate CRF and in detail in the source documentation (preferably the electronic medical record directly).

Adverse Event: Any untoward medical occurrence in a subject administered a pharmaceutical product, which does not necessarily have to have a causal relationship with this treatment. An adverse event can be any unfavorable sign (including an abnormal laboratory finding), symptom, or disease temporally associated with the use of the investigational drug, whether or not considered related to the investigational drug.

Serious Adverse Event: An untoward event or reaction that at any dose:

results in death is life-threatening prolongs existing hospitalization results in permanent or significant disability or incapacity requires intervention to prevent permanent impairment/damage Life-threatening: An event which a subject was at risk of death at the time of event. There is a distinction between the severity and the seriousness of an adverse event. Severity is a measurement of intensity, thus a severe reaction is not necessarily a serious adverse event. For example, a headache may be severe in intensity, but would not be serious unless it met one of the criteria for serious adverse events listed previously.

Serious Adverse Events

Adverse events (AEs) and serious adverse events (SAEs) is collected from the time the first dose of IP is administered until 28 days after the last dose of IP. Medical occurrences that began prior to the start of study treatment, but after obtaining informed consent is captured as Medical History/Current Medical Conditions on the CRF. The Investigator or site staff is responsible for the identification and documentation of events meeting the criteria and definition of an adverse event or serious adverse event, as provided in the study protocol. SAEs assessed as related to study participation (e.g., dosing, protocol mandated procedures, invasive tests, or change in existing therapy) or related to a concomitant medication is captured once the subject has taken the first dose of study medication.

In the event of an AE or SAE, it is the responsibility of the Investigator to review all documentation (e.g., hospital progress notes, laboratory, and diagnostics reports) relative to the event and attempt to establish a diagnosis of the event based on signs, symptoms, and other clinical information. Once the Investigator becomes aware that an SAE has occurred, they are' to report the information to MedStar Health within 24 hours and provide an assessment of causality.

Notification of Serious Adverse Events

The Sponsor reports all serious adverse events to regulatory agencies as required. In addition to the serious adverse events described previously, other events that in the Investigator's opinion suggest a significant hazard, contraindication, or precaution should be considered serious. This includes, but is not limited to, blood dyscrasias, endocrine disturbances, hemorrhage from any site, or severe skin disorder. Additional examples are intensive treatment for allergic bronchospasm, blood dyscrasias or convulsions.

Subjects who experience an SAE must be given appropriate examinations and treatment. The Investigator must provide written information to the Sponsor as soon as possible.

Reporting a Serious Adverse Event

All appropriate SAEs are reported immediately to the FDA per reporting criteria for an IND Safety Report. The event(s) are reported locally to the IRB of record when the event meeting reporting criteria per MedStar Health Research Institute IRB policy.

Departure from Protocol for Emergency or Adverse Event

In medical emergencies, the Investigator should use medical judgment and remove the subject from immediate hazard. As soon as possible after removing the subject from hazard, the Investigator must contact MedStar Health by telephone to permit a decision as to whether the subject may continue in the study. The IRB should also be notified as to the type of emergency and the course of action. The CRF for the subject must capture the departure from the protocol and state the reason.

Safety Monitoring

A Data Safety and Monitoring Board (DSMB) is established to monitor the safety of the subjects during the study. The DSMB includes members who are independent of this study and its Sponsor Team, and with relevant clinical expertise, including a good understanding of the safety of medications for respiratory illnesses. These members may include one or more of the following—a statistician, an infectious disease specialist and/or a pulmonologist. The methodology and the operating procedures for the safety reviews are developed by the infectious disease specialist and/or pulmonologist in collaboration with the Investigator and are documented in the DSMB Charter. They review all SAEs and determine whether the study can proceed or whether protocol modifications are required.

Stopping Rules

During the study it is anticipated that no more than 2 subjects out of 24 have an adverse event of grade 4 or 5 that is at least possibly related to belnacasan (VX-765/RVT-201/MSR-001). Should there be more than 3 subjects with an adverse event grade 4 or 5 that is at least possibly related to the IP, the study is put on an immediate clinical hold.

In addition, individual safety subject study stopping rules include having a non-DLT respiratory adverse event >grade 3 within 24 hours of taking study medication that is at least possibly attributable belnacasan (VX-765/RVT-201/MSR-001).

Follow-Up and Final Reports

The Investigator shall provide MedStar Health with an accurate final report within 1 month after completion, termination or discontinuation of the study. The final report may not precede completion of monitoring relevant CRFs.

Regulatory Aspects

Neither the Investigator nor MedStar Health shall modify this protocol without first obtaining concurrence of the other in writing. All modifications must be submitted to the IRB with approval prior to implementation. Protocol modifications which impact subject safety or the validity of the study must be approved by the IRB and submitted to the FDA before implementation. In the case of a medical emergency to increase safety of subjects, a change may occur immediately, and the IRB and FDA are notified as soon as possible.

Populations for Analyses

The following populations are considered for statistical analyses.

Safety & Tolerability Population: All enrolled subjects who have received at least 1 dose of IP (belnacasan or placebo) are studied. Even if subjects have discontinued study treatment, as long as they maintain consent, they continue to be in the study and included in analysis, i.e., their safety and tolerability information continue to be collected for at least 60 days.

Treatment Effect Evaluable Populations: All enrolled subjects who have received at least 1 dose of IP (belnacasan or placebo) are studied. Even if subjects have discontinued study treatment, as long as they maintain consent, they continue to be in the study and included in analysis, i.e., their outcome information continue to be collected for at least 60 days.

Analysis Methods

General Methods

FDA Data Standard Guidelines are followed. Continuous variables are summarized using the number of observations, number of observations above the limit of quantification (if applicable), mean, standard deviation (SD) median, and range. Categorical variables are summarized using frequency counts and percentages. Comparison of belnacasan (VX-765/RVT-201/MSR-001) and placebo groups utilize Poisson regression for counts, Cox proportional hazards regression for time-to-event data and mixed effects models for continuous and categorical data obtained over study days.

Analysis of Subject Disposition, History, and Baseline Characteristics

Subject disposition, including analysis population allocation, subjects enrolled, completed each period, discontinued, and primary reason for discontinuation, are summarized using frequency and percentage. Protocol deviations are summarized using frequency and percentage. Medical history data and prior and concomitant medications are summarized using frequency and percentage. Subjects' age, height, weight, and baseline disease characteristics are summarized using descriptive statistics. Gender, race, and other categorical variables are provided using frequency and percentage.

Safety & Tolerability Analyses

All safety & tolerability analyses are performed on the Safety Population. The safety dataise presented in individual listings and summary tables.

Overall safety is assessed by the number of belnacasan VX-765/RVT-201/MSR-001 dosed subjects experiencing a grade 4 or 5 SAE during the trial. Of 24 subjects enrolled in the belnacasan group, 3 or more developing a grade 4 or 5 SAE potentially related to belnacasan would be considered unlikely due to chance.

Therefore, belnacasan is determined safe if no more than 2 subjects develop a grade 4 or 5 SAE in the belnacasan group potentially related to belnacasan. If 3 or more subjects in the belnacasan group develop SAEs potentially related to belnacasan during the trial, belnacasan is considered not safe, and the trial stopped or placed on clinical hold as noted.

Primary Endpoint Analysis

Primary endpoints of adverse and serious adverse events (AE/SAE) is assessed by Poisson regression for count data. Events are counted out to 60 days from randomization to belnacasan or placebo groups. Because some subjects may be followed for less than 60 days, subject follow-up time are included in the Poisson regression as the exposure time variable. If counts are not Poisson-distributed, either over- or under-dispersed, negative binomial regression analyze AE/SAE events with appropriate adjustment for over/under dispersion. Comparison of belnacasan vs. placebo is expressed as the incidence rate ratio (IRR).

Adverse Events

AEs are coded according to the latest version of the Medical Dictionary for Regulatory Activities (MedDRA). The intensity/severity of AEs is graded according to NCI CTCAE.

TEAEs, AEs leading to study treatment discontinuation, AEs leading to dose interruption, AEs related to study medication, SAEs, and AEs leading to death are summarized by system organ class, preferred term, and study period. A summary of AEs that are CTCAE Grade 3 or higher, as well as the most frequent preferred terms, are provided.

If a subject experiences the same adverse events multiple times within a period, then the event is counted only once within the period and by greatest severity.

Descriptive statistics are used to summarize the safety data.

Clinical Laboratory Values

All laboratory test results are summarized by period together with the change from baseline. The frequency distribution for low/normal/high or normal/abnormal are summarized as well. The denominators for calculating the percentages are based on the number of subjects with non-missing values in the Safety Population.

Vital Signs

Vital sign results are summarized by period, together with the change from baseline.

Physical Examination

Summaries of physical examinations present frequency distribution of abnormal findings by body system and period. The denominators for calculating the percentages are based on the number of subjects evaluated for a particular body system of each dose level in the Safety Population.

Electrocardiogram (EKG)

EKG findings are classified as normal vs abnormal. The number and percentage of each category is summarized using frequency table for each period. The denominators for calculating the percentages are based on the number of subjects with non-missing values in each period.

Treatment Effect Analyses

Secondary Endpoint Analyses

Event counts over 60 days are analyzed by Poisson regression as described above in 8.4. Time to events are analyzed by Cox regression. Differences between belnacasan and placebo with respect to change in continuous endpoints are assessed by mixed effects models for continuous repeated measures data and mixed effects logistic models for repeated categorical variables. Endpoint proportions of belnacasan and placebo groups are assessed by contingency table analysis (chi-square).

Handling of Missing Data

Although every effort is made to obtain complete data, missing values likely occur when data are collected longitudinally. Patterns of missingness over time as well missingness with respect to demographic and clinical variables are assessed. For Poisson and Cox regression analyses, all data can be used up to subject dropout time.

Sample Size Considerations

A total of 48 subjects are randomized, 24 to belnacasan (VX-765/RVT-201/MSR-001) 900 mg TID and 24 to placebo. As this is a proof-of-concept study, it is likely not powered to detect belnacasan—placebo differences that are clinically meaningful. For example, the observed difference in primary endpoint rate ratios would need to be over 60% to achieve 80% power with an alpha error rate of 5% for 24 subjects in each group. This study provides an estimate of the belnacasan effect size to inform a larger trial where a more clinically meaningful difference can be detected.

This study has an estimated maximum duration of up to 8.5 weeks for each subject. The study duration from first subject enrolled to last subject enrolled is expected to be 3-6 months.

Subject Information and Informed Consent

The Investigator ensures that the subject/LAR fully understands study participation requirements including possible risks and benefits. Subjects must also be notified that they are free to withdraw from the study at any time. During the informed consent process, the subject should be given the opportunity to ask questions and allowed time to consider the information provided. The subjects' informed consent must be obtained before conducting any study-specific procedures.

Study Monitoring

During the study, a dedicated Clinical Research Associate (CRA) have regular contacts with the investigational site, for the following:

Provide information and support to the Investigator,

Confirm that facilities remain acceptable,

Confirm that the investigational team is adhering to the protocol, that data is being accurately recorded in the eCRFs, and that investigational product accountability checks are being performed, Perform source data verification. This includes a comparison of the data in the eCRFs with the subjects' medical records, and other records relevant to the study. This requires access to all original records for each subject (e.g., clinic charts) as described in the study monitoring plan.

Record and report any protocol deviations not previously sent to MedStar Health.

Confirm adverse events and serious adverse events have been properly documented on eCRFs and confirm any serious adverse events have been forwarded to MedStar Health, and those serious adverse events that met criteria for reporting have been reported to the IRB.

The CRA is available over the course of the study if the Investigator or other staff needs information or advice. Remote visits are conducted until it is possible to perform on-site visits.

Audits and Inspections

Authorized representatives of the FDA, or the Institutional Review Board (IRB) may visit the site to perform audits or inspections, including source data verification. The purpose of any inspection is to systematically and independently examine all study-related activities and documents to determine whether these activities were conducted, and data were recorded, analyzed, and accurately reported according to the protocol, Good Clinical Practice (GCP) guidelines of the International Conference on Harmonization (ICH), and FDA regulations. The Investigator/Sponsor should contact the site immediately if contacted by a regulatory agency about an inspection.

Ethics Committee Review

The final study protocol, including the final version of the Informed Consent Form, must be approved by the MedStar Health Research Institute IRB.

The Sponsor is responsible for submitting any modifications to the Protocol to the IRB and obtaining approval in advance of implementing these modifications. In addition, the IRB must approve all advertising used to recruit subjects for the study. The study must also be renewed annually with the IRB as long as study conduct is occurring.

The Investigator/Sponsor are also responsible for providing the IRB with reports of any reportable new information (RNI) including any serious adverse drug reactions from any other study conducted with the investigational product.

Standards

The study is performed in accordance with ethical principles that have their origin in the Declaration of Helsinki and are consistent with ICH/GCP and applicable regulatory requirements.

Confidentiality

Any research information obtained specific to subjects enrolled into this study are kept confidential. A subject are not identified by name, only by a unique study number. The subject's name or any identifying information does not appear in any reports published as a result of this study.

However, information obtained from individual subjects' participation in the study may be disclosed with his/her consent to the healthcare providers for the purpose of obtaining appropriate medical care. The subject's medical records/charts, tests with his/her name on them may be made available to the appropriate contract research organization (CRO), MedStar Health, IRB, and the FDA. This is for the purpose of verifying information obtained for this study.

A subject's name is not to be given to anyone except the researchers conducting the study, who have pledged an oath of confidentiality. All identifying information is kept behind locked doors, under the supervision of the Investigator and is not to be transferred outside of WHC/MedStar as applicable.

A subject may take away his/her permission to collect, use and share information about him/her at any time. If this situation occurs, the subject is not able to remain in the study. No new information that identifies the subject is gathered after that date. However, the data about the subject that has already been collected may still be used and given to others as described above in order to preserve the scientific integrity and quality of the study.

Protocol Adherence

The records of study treatment delivered to subjects and IP inventory is maintained at WHC/MedStar; the administration to each subject; and storage or disposal of any unused IP. These records should include dates, quantities, batch/serial numbers, expiration dates, IDS temperature log, and unique code numbers assigned to the product and study subjects.

The Investigator maintains records that document adequately that the subjects were provided with the correct study drug and maintains IP accountability and tracking records.

Amendments to the Protocol

Modifications to the protocol are only possible by approved protocol amendments authorized by the Sponsor, approved by the IRB, and deemed as not-objectionable by the FDA. The Investigator must not implement any deviations from, or changes to the protocol, except where it is necessary to eliminate an immediate hazard to the study subject.

Protocol Deviations

The protocol must be conducted compliantly, significant deviations from the protocol is reported to the FDA and/or IRB per policy.

Study Termination

This study may be prematurely terminated, if in the opinion of the Investigator or MedStar Health there is sufficient reasonable cause. Circumstances that may warrant termination include, but are not limited to:

Determination of unexpected, significant, or unacceptable risk to subjects.

Failure to enroll subjects at an acceptable rate.

Insufficient adherence to protocol requirements.

Insufficient complete and/or evaluable data.

Plans to modify, suspend, or discontinue the development of belnacasan (VX-765/RVT-201).

Inspection of Records

MedStar Health is allowed to audit data for the purpose of monitoring any aspect of the study they deem necessary, pursuant to local restrictions on monitoring due to health concerns. The Investigator agrees to allow the IRB and regulatory authorities to inspect the drug storage area, study drug stocks, drug accountability records, subject charts and study source documents, and other records relative to study conduct. Remote access can be granted in the event the pandemic prevents on-site monitoring.

Data Management

All data relating to study procedures is entered onto the eCRF (OnCore platform). CRF completion guidelines are developed to assure the required data is appropriately captured. eCRFs are completed for each subject. It is the Investigator's responsibility to ensure the accuracy, completeness, and timeliness of the data entered in each subject's eCRF. Source documentation supporting the eCRF data should indicate the subject's participation in the study and document the dates and details of study procedures, adverse events, and subject status.

The Investigator, or designee, should complete the eCRF as soon as possible after data is collected, preferably on the same day that a subject is seen for an examination, treatment, or any other study procedure. Any outstanding entries must be entered immediately after the final examination. An explanation should be given for all late or missing data.

Liability and Insurance

MedStar Health has subscribed to an insurance policy covering, in its terms and conditions, its legal liability for certain injuries to participating persons arising out of this research performed strictly in accordance with the scientific protocol as well as with applicable law and professional standards.

Retention of Records

Investigators shall retain study records and source documents for a period of 2 years following the date a marketing application is approved for the drug for the indication for which it is being investigated; or, if no application is to be filed or if the application is not approved for such indication, until 2 years after the investigation is discontinued and FDA is notified and/or the period required by local, state, and federal laws, regulations and FDA Guidance.

The Investigator agrees to comply with all applicable federal, state, and local laws and regulations relating to the privacy of protected health information, including, but not limited to, the Standards for Individually Identifiable Health Information, 45 CFR, Parts 160 and 164 (the Health Insurance Portability Accountability Act of 1996 [HIPAA] Privacy Regulation). The Investigator shall ensure that study subjects authorize the use and disclosure of protected health information in accordance with HIPAA Privacy Regulation.

Data Quality Assurance

WHC/MedStar and all relevant subject study and medical records may be subject to a quality assurance audit during the course of the study. In addition, inspections may be conducted by the FDA at their discretion.

Both the use of data and the publication policy are detailed within the clinical study agreement. Intellectual property rights (and related matters) generated by the Investigator and others performing the clinical study are subject to the terms of a clinical study agreement that is agreed between the Institution and MedStar Health or their designee. With respect to such rights, MedStar Health or its designee solely owns all rights and interests in any materials, data, and intellectual property rights developed by Investigators and others performing the clinical study described in this protocol, subject to the terms of any such agreement. In order to facilitate such ownership, Investigators are required to assign all such inventions directly to MedStar Health or its designee, as are set forth in the clinical study agreement.

APPENDIX

| Labs and Tests | |
|---|---|
| Hematology | Serum Chemistry |
| Complete Blood Count: | Albumin |
| White Blood Cell (WBC) Count | Alanine Aminotransferase (ALT) |
| Red Blood Cell (RBC) Count | Alkaline Phosphatase (ALP) |
| Hemoglobin (Hb) | Aspartate Aminotransferase (AST) |
| Hematocrit (Hct) | Blood Urea Nitrogen (BUN) |
| Mean Corpuscular Volume (MCV) | Calcium |
| Red Blood Cell Distribution Width (RDW) | Carbon Dioxide |
| | Chloride |
| Platelet Count | Creatinine |
| Differential - absolute and percent of: | Glucose |
| | Lipase |
| Neutrophils | Magnesium |
| Lymphocytes | Potassium |
| Monocytes | Sodium |
| Eosinophils | Total Bilirubin |
| Basophils | Total Protein |
| Coagulation Tests: | Lactate Dehydrogenase (LDH) |
| Partial Thromboplastin Time (PTT) | Creatine Kinase, Total |
| Prothrombin Time (PT) | CRP |
| Immune Cell Counts - absolute and percent of: | Ferritin |
| | D-Dimer |
| CD3+ T cells | HbA1c |
| Serum and Plasma Levels of Cytokines and Inflammasome Markers: | Screening Tests |
| | HIV |
| | Hepatitis B |
| IL-18 | Hepatitis C |
| IL-1β | Pregnancy (serum pregnancy test for women of child-bearing potential per MedStar definition) |
| IL-1 receptor antagonist | |
| IL-6 | |
| Gasdermin D | |
| G-CSF | |
| TNF-α | |
| Caspase-1 | |

FIGS. 5A-5C provide a Subject Diary.

A randomization table such as the one below are used to allocate subjects to belnacasan or placebo group (N=24 each). Assignment of A or B to treatment or placebo blinded to subjects and investigators.

| Sequential subject | Group assignment | Sequential subject | Group assignment |
|---|---|---|---|
| 1 | A | 25 | B |
| 2 | B | 26 | A |
| 3 | B | 27 | A |
| 4 | A | 28 | B |
| 5 | A | 29 | A |
| 6 | B | 30 | B |
| 7 | A | 31 | A |
| 8 | B | 32 | B |
| 9 | A | 33 | A |
| 10 | A | 34 | A |
| 11 | B | 35 | B |
| 12 | B | 36 | B |
| 13 | B | 37 | B |
| 14 | A | 38 | B |
| 15 | A | 39 | A |
| 16 | B | 40 | A |
| 17 | B | 41 | B |
| 18 | A | 42 | A |
| 19 | B | 43 | B |
| 20 | A | 44 | A |
| 21 | B | 45 | A |
| 22 | B | 46 | B |
| 23 | A | 47 | B |
| 24 | A | 48 | A |

The invention is further described by the following numbered paragraphs:

1. A method for treating a patient infected with SARS-CoV-2 or a variant thereof and having pyroptotic activity comprising (a) determining if the patient is infected with SARS-CoV-2 or a variant thereof, (b) optionally determining if the patient has pyroptotic activity or a comorbidity associated with upregulation of an inflammasome/caspase/pyroptosis axis, and (c) administering an effective amount of a compound having the formula

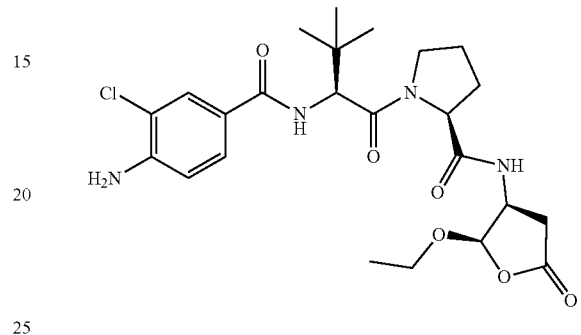

to the patient infected with SARS-CoV-2 or a variant thereof.

2. The method of numbered paragraph 1, wherein step (b) comprises screening a marker indicative of pyroptotic activity, wherein the marker has increased activity if pyroptotic activity is present.

3. The method of numbered paragraph 2, wherein the marker is NOD-, LRR- and pyrin domain-containing protein 3 (NLRP3), IL-1 receptor antagonist (IL-1RA), interleukin-1β (IL-1β), interleukin-18 (IL-18), gasdermin D (GSDMD), caspase 1, lymphopenia, a high neutrophil count, elevated LDH, ferritin or CRP levels.

4. The method of any one of numbered paragraphs 1-3, wherein the effective amount in step (c) is about 10 mg/kg to about 100 mg/kg.

5. The method of numbered paragraph 4, wherein the effective amount is 300 mg to about 900 mg per dose.

6. The method of numbered paragraph 5, wherein the effective dose is about 600 mg to about 900 mg per dose.

7. The method of any one of numbered paragraphs 4-6, wherein the effective dose is about 300 mg to about 3600 mg per day.

8. The method of any one of numbered paragraphs 5-7, wherein the 300 mg to about 900 mg is administered three or four times a day.

9. The method of numbered paragraph 8, wherein the administering is about every six to about eight hours.

10. The method of any one of numbered paragraphs 1-9, wherein the administering in step (c) is oral.

11. The method of numbered paragraph 10, wherein the oral administering is a tablet.

12. The method of numbered paragraph 10, wherein the tablet comprises a 300 mg dose.

13. The method of numbered paragraph 12, wherein the administering comprises one tablet, two tablets or three tablets.

14. The method of any one of numbered paragraphs 1-13, wherein the administering in step (c) further comprises administering an effective amount of a caspase 1, GSDMD, IL-1R IL-1β, IL-6, IL-18, NLRP3, pan-caspase or TNF-α inhibitor.

REFERENCES

[1] Huang C, Wang Y, Li X, Ren L, Zhao J, Hu Y, et al. Clinical features of patients infected with 2019 novel coronavirus in Wuhan, China. Lancet 2020; 395:497-506.

[2] JHU. Coronavirus Resource Center. 2020 [cited; Available from: https://coronavirus.jhu.edu/us-map

[3] Chen G, Wu D, Guo W, Cao Y, Huang D, Wang H, et al. Clinical and immunological features of severe and moderate coronavirus disease 2019. J Clin Invest 2020; 130: 2620-2629.

[4] Richardson S, Hirsch J S, Narasimhan M, Crawford J M, McGinn T, Davidson K W, et al. Presenting Characteristics, Comorbidities, and Outcomes Among 5700 Patients Hospitalized With COVID-19 in the New York City Area. JAMA 2020.

[5] Moon A M, Webb G J, Aloman C, Armstrong M J, Cargill T, Dhanasekaran R, et al. High Mortality Rates for SARS-CoV-2 Infection in Patients with Pre-existing Chronic Liver Disease and Cirrhosis: Preliminary Results from an International Registry. J Hepatol 2020.

[6] Kroemer A, Khan K, Plassmeyer M, Alpan O, Haseeb M A, Gupta R, et al. Inflammasome activation and pyroptosis in lymphopenic liver patients with COVID-19. J Hepatol 2020; 73:1258-1262.

[7] Beigel J H, Tomashek K M, Dodd L E, Mehta A K, Zingman B S, Kalil A C, et al. Remdesivir for the Treatment of Covid-19—Preliminary Report. N Engl J Med 2020.

[8] Cohen M S. Monoclonal Antibodies to Disrupt Progression of Early Covid-19 Infection. N Engl J Med 2021; 384:289-291.

[9] Group R C, Horby P, Lim W S, Emberson J R, Mafham M, Bell J L, et al. Dexamethasone in Hospitalized Patients with Covid-19—Preliminary Report. N Engl J Med 2020.

[10] Rubin E J, Longo D L. SARS-CoV-2 Vaccination—An Ounce (Actually, Much Less) of Prevention. N Engl J Med 2020; 383:2677-2678.

[11] Boyarsky B J, Werbel W A, Avery R K, Tobian AAR, Massie A B, Segev D L, et al. Immunogenicity of a Single Dose of SARS-CoV-2 Messenger RNA Vaccine in Solid Organ Transplant Recipients. JAMA 2021.

[12] Grupper A, Rabinowich L, Schwartz D, Schwartz I F, Ben-Yehoyada M, Shashar M, et al. Reduced humoral response to mRNA SARS-Cov-2 BNT162b2 vaccine in kidney transplant recipients without prior exposure to the virus. Am J Transplant 2021.

[13] Hie B, Zhong E D, Berger B, Bryson B. Learning the language of viral evolution and escape. Science 2021; 371:284-288.

[14] Callaway E. Fast-spreading COVID variant can elude immune responses. Nature 2021; 589:500-501.

[15] Karim S S A. Vaccines and SARS-CoV-2 variants: the urgent need for a correlate of protection. Lancet 2021; 397:1263-1264.

[16] Vabret N, Britton G J, Gruber C, Hegde S, Kim J, Kuksin M, et al. Immunology of COVID-19: Current State of the Science. Immunity 2020; 52:910-941.

[17] Rodrigues T S, de Sa K S G, Ishimoto A Y, Becerra A, Oliveira S, Almeida L, et al. Inflammasomes are activated in response to SARS-CoV-2 infection and are associated with COVID-19 severity in patients. J Exp Med 2021; 218.

[18] Bryant C. COVID-19 stokes inflammasomes. J Exp Med 2021; 218.

[19] Toldo S, Bussani R, Nuzzi V, Bonaventura A, Mauro A G, Cannata A, et al. Inflammasome formation in the lungs of patients with fatal COVID-19. Inflamm Res 2021; 70:7-10.

[20] Paul O, Tao J Q, Litzky L, Feldman M, Montone K, Rajapakse C, et al. Vascular Inflammation in Lungs of Patients with Fatal Coronavirus Disease 2019 (COVID-19) Infection: Possible role for the NLRP3 inflammasome. medRxiv 2021.

[21] Ferreira A C, Soares V C, de Azevedo-Quintanilha I G, Dias S, Fintelman-Rodrigues N, Sacramento C Q, et al. SARS-CoV-2 engages inflammasome and pyroptosis in human primary monocytes. Cell Death Discov 2021; 7:43.

[22] Junqueira C, Crespo A, Ranjbar S, Ingber J, Parry B, Ravid S, et al. SARS-CoV-2 infects blood monocytes to activate NLRP3 and AIM2 inflammasomes, pyroptosis and cytokine release. medRxiv 2021.

[23] Xu H, Chitre S A, Akinyemi I A, Loeb J C, Lednicky J A, McIntosh M T, et al. SARS-CoV-2 viroporin triggers the NLRP3 inflammatory pathway. bioRxiv 2020: 2020.2010.2027.357731.

[24] Lucas C, Wong P, Klein J, Castro T B R, Silva J, Sundaram M, et al. Longitudinal analyses reveal immunological misfiring in severe COVID-19. Nature 2020.

[25] Freeman T L, Swartz T H. Targeting the NLRP3 Inflammasome in Severe COVID-19. Front Immunol 2020; 11:1518.

[26] Shah A. Novel Coronavirus-Induced NLRP3 Inflammasome Activation: A Potential Drug Target in the Treatment of COVID-19. Front Immunol 2020; 11:1021.

[27] van den Berg D F, Te Velde A A. Severe COVID-19: NLRP3 Inflammasome Dysregulated. Front Immunol 2020; 11:1580.

[28] Yap J K Y, Moriyama M, Iwasaki A. Inflammasomes and Pyroptosis as Therapeutic Targets for COVID-19. J Immunol 2020; 205:307-312.

[29] de Rivero Vaccari J C, Dietrich W D, Keane R W, de Rivero Vaccari J P. The Inflammasome in Times of COVID-19. Front Immunol 2020; 11:583373.

[30] Lee S, Channappanavar R, Kanneganti T D. Coronaviruses: Innate Immunity, Inflammasome Activation, Inflammatory Cell Death, and Cytokines. Trends Immunol 2020; 41:1083-1099.

[31] Hoel H, Heggelund L, Reikvam D H, Stiksrud B, Ueland T, Michelsen A E, et al. Elevated markers of gut leakage and inflammasome activation in COVID-19 patients with cardiac involvement. J Intern Med 2020.

[32] Moccia F, Gerbino A, Lionetti V, Miragoli M, Munaron L M, Pagliaro P, et al. COVID-19-associated cardiovascular morbidity in older adults: a position paper from the Italian Society of Cardiovascular Researches. Geroscience 2020; 42:1021-1049.

[33] Guo H, Callaway J B, Ting J P. Inflammasomes: mechanism of action, role in disease, and therapeutics. Nat Med 2015; 21:677-687.

[34] Lopez-Reyes A, Martinez-Armenta C, Espinosa-Velazquez R, Vazquez-Cardenas P, Cruz-Ramos M, Palacios-Gonzalez B, et al. NLRP3 Inflammasome: The Stormy Link Between Obesity and COVID-19. Front Immunol 2020; 11:570251.

[35] Marchetti C, Mould K, Tengesdal I W, Janssen W J, Dinarello C A. Targeting of the NLRP3 Inflammasome for early COVID-19. bioRxiv 2021:2021.2002.2024.432734.

[36] Lambadiari V, Kousathana F, Raptis A, Katogiannis K, Kokkinos A, Ikonomidis I. Pre-Existing Cytokine and NLRP3 Inflammasome Activation and Increased Vascular Permeability in Diabetes: A Possible Fatal Link With Worst COVID-19 Infection Outcomes? Front Immunol 2020; 11:557235.

Having thus described in detail preferred embodiments of the present invention, it is to be understood that the invention defined by the above paragraphs is not to be limited to particular details set forth in the above description as many apparent variations thereof are possible without departing from the spirit or scope of the present invention.

What is claimed is:

1. A method for treating a patient infected with SARS-CoV-2 or a variant thereof, wherein the SARS-CoV-2 and the variant thereof have pyroptotic activity, said comprising
    (a) determining if the patient is infected with SARS-CoV-2 or the variant thereof,
    (b) optionally determining if the patient has pyroptotic activity or a comorbidity associated with upregulation of an inflammasome/caspase/pyroptosis axis, and
    (c) administering to the patient infected with SARS-CoV-2 or a variant thereof an effective amount of a compound comprising about 10 mg of compound/kg bodyweight of patient to about 100 mg of compound/kg bodyweight of patient per day for up to 15 days or up to 28 days, in an amount comprising about 600 mg to about 900 mg of the compound per dose, wherein the about 600 mg to about 900 mg of the compound per dose is administered three to four times each day, or every six to eight hours each day, or comprises the patient receiving a first dose of about 900 mg of the compound per dose, and thereafter receiving a second dose of about 900 mg of the compound per dose 8-12 hours after the first dose, and wherein the compound has the formula or is a derivative, prodrug or salt of the formula

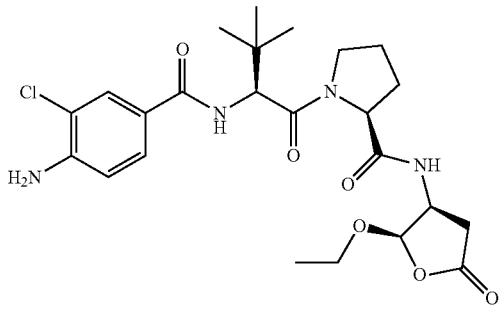 [SMILES: CCO[C@@H]1OC(=O)C[C@@H]1NC(=O)[C@@H]1CCCN1C(=O)[C@@H](NC(=O)c1ccc(N)c(Cl)c1)C(C)(C)C]

wherein the administering comprises administering a composition comprising the effective amount of the compound of the formula, or the derivative of the compound of the formula, or the prodrug of the compound of the formula or the salt of the compound of the formula, and a pharmaceutically acceptable carrier.

2. The method of claim 1, wherein step (b) is performed and comprises screening a marker indicative of pyroptotic activity, wherein the marker has increased activity if pyroptotic activity is present.

3. The method of claim 2, wherein the marker is D-Dimer, NOD-, LRR- and pyrin domain-containing protein 3 (NLRP3), IL-1 receptor antagonist (IL-1RA), interleukin-1β (IL-1β), interleukin-18 (IL-18), gasdermin D (GSDMD), caspase 1, lymphopenia, a high neutrophil count, elevated LDH, ferritin or CRP levels.

4. The method of claim 1, wherein the administering comprises the patient receiving a first dose of about 900 mg of the compound of the formula or salt thereof, and thereafter receiving a second dose of the compound of the formula or salt thereof 8-12 hours after the first dose.

5. The method of claim 4, wherein the administering comprises orally administering the compound of the formula or salt thereof in tablet form, wherein each tablet comprises a 300 mg dose of the compound of the formula or a salt thereof.

6. The method of claim 1, wherein the administering comprises orally administering the compound of the formula or salt thereof in tablet form, wherein each tablet comprises a 300 mg dose of the compound of the formula or a salt thereof.

7. The method of claim 1, wherein the administering comprises administering 600 mg to about 900 mg per dose of the compound of the formula or a salt thereof three or four times a day.

8. The method of claim 7, wherein the administering comprises administering 600 mg to about 900 mg per dose of the compound of the formula or a salt thereof about every six to about eight hours within the day.

9. The method of claim 1, wherein the administering in step (c) is orally.

10. The method of claim 2, wherein the administering in step (c) is orally.

11. The method of claim 3, wherein the administering in step (c) is orally.

12. The method of claim 4, wherein the administering in step (c) is orally.

13. The method of claim 7, wherein the administering in step (c) is orally.

14. The method of claim 8, wherein the administering in step (c) is orally.

15. The method of claim 9, wherein the composition is in tablet form.

16. The method of claim 10, wherein the composition is in tablet form.

17. The method of claim 11, wherein the composition is in tablet form.

18. The method of claim 13, wherein the composition is in tablet form.

19. The method of claim 14, wherein the composition is in tablet form.

20. The method of claim 15, wherein the tablet form comprises each tablet comprising a 300 mg dose of the compound of the formula or a salt thereof.

21. The method of claim 1, wherein the administering comprises administering the compound of the formula or a salt thereof.

22. The method of claim 9, wherein the administering comprises administering the compound of the formula or a salt thereof.

23. The method of claim 15, wherein the administering comprises administering the compound of the formula or a salt thereof.

24. The method of claim 1, wherein the administering in step (c) further comprises administering an effective amount of a caspase 1, GSDMD, IL-1R, IL-1β, IL-6, IL-18, NLRP3, pan-caspase, TNF-α inhibitor, or an antiviral medication.

25. The method of claim 16, wherein the tablet form comprises each tablet comprising a 300 mg dose of the compound of the formula or a salt thereof.

26. The method of claim 17, wherein the tablet form comprises each tablet comprising a 300 mg dose of the compound of the formula or a salt thereof.

27. The method of claim 18, wherein the tablet form comprises each tablet comprising a 300 mg dose of the compound of the formula or a salt thereof.

28. The method of claim 19, wherein the tablet form comprises each tablet comprising a 300 mg dose of the compound of the formula or a salt thereof.

29. The method of claim 24, wherein the administering comprises orally administering the compound or salt thereof in tablet form, wherein the tablet form comprises each tablet comprising a 300 mg dose of the compound of the formula or a salt thereof.

* * * * *